United States Patent
Yabunouchi et al.

(10) Patent No.: US 7,998,596 B2
(45) Date of Patent: Aug. 16, 2011

(54) AROMATIC AMINE DERIVATIVE AND ORGANIC ELECTROLUMINESCENCE DEVICE USING THE SAME

(75) Inventors: Nobuhiro Yabunouchi, Chiba (JP); Masahiro Kawamura, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 293 days.

(21) Appl. No.: 12/187,013

(22) Filed: Aug. 6, 2008

(65) Prior Publication Data
US 2009/0066235 A1     Mar. 12, 2009

(30) Foreign Application Priority Data
Aug. 6, 2007 (JP) .................. 2007-204407

(51) Int. Cl.
H01L 51/54 (2006.01)
H01J 1/63 (2006.01)
C07D 409/14 (2006.01)
C07D 411/14 (2006.01)

(52) U.S. Cl. ........ 428/690; 428/917; 313/504; 313/506; 548/440; 549/60

(58) Field of Classification Search ................. None
See application file for complete search history.

(56) References Cited

U.S. PATENT DOCUMENTS

| | | | |
|---|---|---|---|
| 7,153,980 B2 | 12/2006 | Ohba et al. | |
| 2004/0115475 A1 | 6/2004 | Hashimoto | |
| 2007/0045618 A1 | 3/2007 | Li et al. | |
| 2007/0167654 A1 | 7/2007 | Yabunouchi et al. | |
| 2008/0312453 A1* | 12/2008 | Hirose et al. | 548/444 |
| 2009/0066235 A1 | 3/2009 | Yabunouchi et al. | |

FOREIGN PATENT DOCUMENTS

| | | |
|---|---|---|
| EP | 1 661 888 A1 | 5/2006 |
| EP | 1 752 458 A2 | 2/2007 |
| EP | 1 767 608 A1 | 3/2007 |
| GB | 2 230 191 A | 4/2003 |
| JP | 11-329737 | 11/1999 |
| JP | 2003-176282 | 6/2003 |
| JP | 2003-201472 | 7/2003 |
| JP | 2003-267972 | 9/2003 |
| JP | 2004-091342 | 3/2004 |
| JP | 2005-082655 | 3/2005 |
| JP | 2006-151979 | 6/2006 |
| JP | 2007-045817 | 2/2007 |
| JP | 2007-77094 | 3/2007 |
| JP | 2007-088431 | 4/2007 |
| JP | 2007-091714 | 4/2007 |
| JP | 2007-126403 | 5/2007 |
| JP | 2007-126439 | 5/2007 |
| WO | WO 2007/043484 A1 | 4/2007 |
| WO | WO 2007/058172 A1 | 5/2007 |
| WO | WO 2007/080704 A1 | 7/2007 |

OTHER PUBLICATIONS

Lin et al., Proceedings of SPIE, Organic Light-Emitting Materials and Devices, vol. 4464, (2002), pp. 307-316.*
Machine-generated translation for JP 2003-201472 A, which was published Jul. 2003.*
U.S. Appl. No. 12/428,554, filed Apr. 23, 2009, Yabunouchi.
Iuan-Yuan Wu, et al. "Diphenylthienylamine-Based Star-Shaped Molecules for Electroluminescence Applications" American Chemical Society, Chem. Mater. vol. 13, No. 8, Jun. 29, 2001, pp. 2626-2631.

* cited by examiner

Primary Examiner — Dawn Garrett
(74) Attorney, Agent, or Firm — Oblon, Spivak, McClelland, Maier & Neustadt, L.L.P.

(57) ABSTRACT

Provided are an organic electroluminescent device including an aromatic amine derivative formed of a specific structure having a thiophene structure and an organic thin film layer interposed between a cathode and an anode and formed of one layer or a plurality of layers including at least a light emitting layer, in which at least one layer of the organic thin film contains the aromatic amine derivative alone or as a component of a mixture, the organic electroluminescent device in which molecules hardly crystallize, and which decreases a driving voltage, can be produced with improved yields upon the production of the organic electroluminescent device, and has a long lifetime, and an aromatic amine derivative realizing the organic electroluminescent device.

33 Claims, No Drawings

AROMATIC AMINE DERIVATIVE AND ORGANIC ELECTROLUMINESCENCE DEVICE USING THE SAME

TECHNICAL FIELD

The present invention relates to an aromatic amine derivative and an organic electroluminescent (EL) device using the same, and more particularly, to an aromatic amine derivative capable of decreasing a driving voltage and suppressing crystallization of a molecule at the same time, thereby improving a lifetime of the organic EL device and enhancing yields upon production of the organic EL device.

BACKGROUND ART

An organic EL device is a spontaneous light emitting device which utilizes such a principle that a fluorescent substance emits light by virtue of recombination energy of holes injected from an anode and electrons injected from a cathode by an application of an electric field. Since an organic EL device of the laminate type capable of being driven under low electric voltage has been reported by C. W. Tang et al. of Eastman Kodak Company (C. W. Tang and S. A. Vanslyke, Applied Physics Letters, Volume 51, Page 913, 1987, or the like), many studies have been conducted for an organic EL device using an organic material as a constituent material. Tang et al. used tris(8-quinolinolato)aluminum for a light emitting layer and a triphenyldiamine derivative for a hole transporting layer. Advantages of the laminate structure reside in the followings: an efficiency of the hole injection into the light emitting layer can be increased; an efficiency of forming exciton which are formed by blocking and recombining electrons injected from the cathode can be increased; and exciton formed within the light emitting layer can be enclosed. As described above, for the structure of the organic EL device, a two-layered structure having a hole transporting (injecting) layer and an electron transporting light emitting layer and a three-layered structure having a hole transporting (injecting) layer, a light emitting layer, an electron transporting (injecting) layer, and the like are widely known. In order to increase the efficiency of recombination of injected holes and electrons in the devices of the laminate type, the device structure and the process for forming the device have been studied.

In general, when an organic EL device is driven or stored in an environment of high temperature, there occur adverse effects such as a change in the luminescent color, a decrease in current efficiency, an increase in driving voltage, and a decrease in a lifetime of light emission. In order to prevent the adverse effects, it has been necessary that the glass transition temperature (Tg) of the hole transporting material be elevated. Therefore, it is necessary that many aromatic groups be held within a molecule of the hole transporting material (for example, an aromatic diamine derivative of Patent Document 1 and a fused aromatic ring diamine derivative of Patent Document 2), and in general, a structure having 8 to 12 benzene rings are preferably used.

However, when a large number of aromatic groups are present in a molecule, crystallization is liable to occur upon production of the organic EL device through the formation of a thin film by using those hole transporting materials. As a result, there arises a problem such as clogging of an outlet of a crucible to be used in vapor deposition or a reduction in yields of the organic EL device due to generation of defects of the thin film resulting from the crystallization. In addition, a compound having a large number of aromatic groups in any one of its molecules generally has a high glass transition temperature (Tg), but has a high sublimation temperature. Accordingly, there arises a problem in that the lifetime of the compound is short, because a phenomenon such as decomposition at the time of the vapor deposition or the formation of a nonuniform deposition is expected to occur.

On the other hand, there is a known document disclosing an asymmetric aromatic amine derivative. For example, in Patent Document 3, there is described an aromatic amine derivative having an asymmetric structure, but there is no specific example thereof, and also, there is no description of a feature of the asymmetric compound at all. Further, in Patent Document 4, an asymmetric aromatic amine derivative containing phenanthrene is described as an example, but the derivative is lumped into the same category as symmetric compounds and there is no description of a feature of the asymmetric compound at all. Further, although the asymmetric compound needs a special synthesis method, a description on a production method of the asymmetric compound is not clearly disclosed in those patent documents. Also, in Patent Document 5, there is a description on the production method of the aromatic amine derivative having an asymmetric structure, but there is no description of a feature of the asymmetric compound. In Patent Document 6, there is a description on an asymmetric compound which has a high glass transition temperature and is thermally stable, but only a compound containing carbazole is exemplified.

Further, Patent Documents 7 and 8 are reports on amine compounds each having thiophene. Those are compounds which each have thiophene in a central skeleton of a diamine compound. Further, in the compound of Patent Document 7, the thiophene is directly bonded to amine. Patent Documents 9 and 10 are given as reports on a compound having thiophene at a terminal of a diamine compound, and in those compounds, thiophene is directly bonded to amine. Those compounds are unstable and the purification thereof is difficult; therefore, the purity thereof does not improve. Further, when the thiophene is directly bonded to the amine, an electronic state of the amine largely changes; therefore, sufficient performance cannot be obtained in the case where each of the compounds is used as a material for the organic EL device. On the other hand, in Patent Document 11, there is a description on compounds in which the thiophene is bonded to the amine through an aryl group. However, those compounds have a structure including an unsubstituted thiophene at 2- or 5-position thereof. 2- or 5-position of thiophene has high reactivity and is electrically unstable, and when the thiophenes are present in the molecule, a high voltage is required in the case where the compounds are each used as a device; therefore, those compounds are not preferred. Patent Document 12 is given as the description of amine polymers, but there is only specific examples and is no description on the amine compound in which the thiophene is bonded to nitrogen through the aryl group at all. A polymer is described in Patent Documents 13 to 22, but cannot be subjected to vapor deposition. Further, a polar group required for polymerization decreases the lifetime as a device; thus, the polar group is not preferred.

As described above, it is generally known that the compound having a thiophene structure has a high mobility, but a sufficient performance cannot be obtained, when used as a material of the organic EL device, by merely combining the compound with an amine structure. Therefore, development of a material for an organic EL device having further improved performance has been strongly desired.

[Patent Document 1] U.S. Pat. No. 4,720,432
[Patent Document 2] U.S. Pat. No. 5,061,569
[Patent Document 3] JP 08-48656 A

[Patent Document 4] JP 11-135261 A
[Patent Document 5] JP 2003-171366 A
[Patent Document 6] U.S. Pat. No. 6,242,115
[Patent Document 7] WO 2004-058740
[Patent Document 8] JP 04-304466 A
[Patent Document 9] WO 2001-053286
[Patent Document 10] JP 07-287408 A
[Patent Document 11] JP 2003-267972 A
[Patent Document 12] JP 2004-155705 A
[Patent Document 13] JP 2005-042004 A
[Patent Document 14] JP 2005-259441 A
[Patent Document 15] JP 2005-259442 A
[Patent Document 16] JP 2005-235645 A
[Patent Document 17] JP 2005-235646 A
[Patent Document 18] JP 2005-082655 A
[Patent Document 19] JP 2004-288531 A
[Patent Document 20] JP 2004-199935 A
[Patent Document 21] JP 2004-111134 A
[Patent Document 22] JP 2002-313574 A

DISCLOSURE OF THE INVENTION

Problems to be Solved by the Invention

The present invention has been made with a view to solving the above-mentioned problems, and an object of the present invention is to provide an organic EL device in which a molecule hardly crystallizes, and which decreases a driving voltage, can be produced with improved yields upon the production of the organic EL device, and has a long lifetime, and an aromatic amine derivative realizing the organic EL device.

Means for Solving the Problems

The inventors of the present invention have made extensive studies with a view toward achieving the above-mentioned object. As a result, the inventors have found that the above-mentioned problems can be solved by using a novel aromatic amine derivative having a specific substituent including thiophene, which is represented by the following general formula (1), as a material for an organic EL device, and particularly as a hole transporting material. Thus, the present invention has been completed.

Further, the inventors of the present invention have found that each of amino groups substituted by an aryl group having a thiophene structure represented by the general formulae (2) and (13) is suitable as an amine unit having a specific substituent. The inventors have found that the amine unit has an effect of decreasing a driving voltage from the following reasons: the injection of charge becomes easy because an interaction between the amine unit and an electrode is possible owing to the fact that the amine unit has a polar group; and the mobility is high because the amine unit has a thiophene structure. Also, it has been found that, because an interaction between molecules of the amine unit is small owing to its steric hindrance, the amine unit has such effects that crystallization is suppressed, yield in which an organic EL device is produced is improved, an organic EL device having a long lifetime can be provided, and a remarkably low driving voltage and long lifetime can be attained by combining the amine unit with a blue light emitting device in particular. In addition, among compounds having large molecular weight, the compound having an asymmetric structure suppresses decomposition at the time of the vapor deposition because the compound can lower the vapor deposition temperature, and is capable of realizing the longer lifetime.

That is, the present invention provides an aromatic amine derivative represented by the following general formula (1):

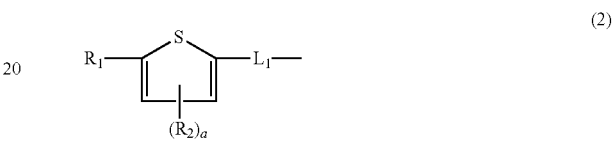
(1)

where: at least one of $Ar_1$ to $Ar_3$ is represented by the following general formula (2); and at least one of $Ar_1$ to $Ar_3$ is represented by any one of the following general formulae (3) to (7):

(2)

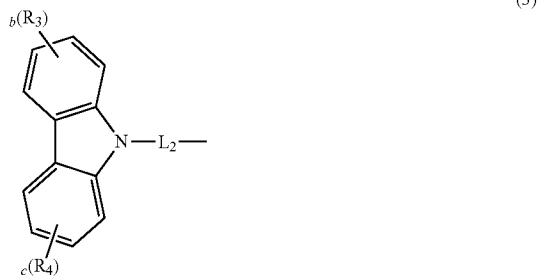
(3)

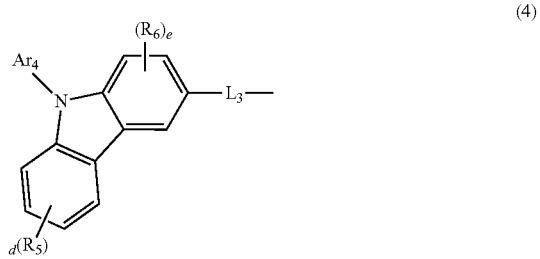
(4)

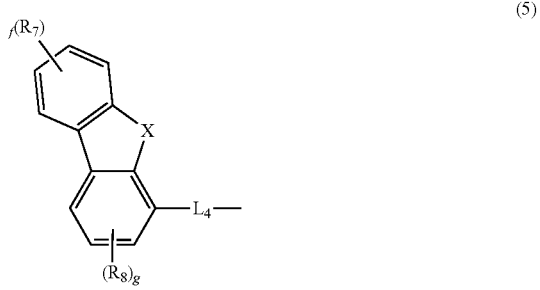
(5)

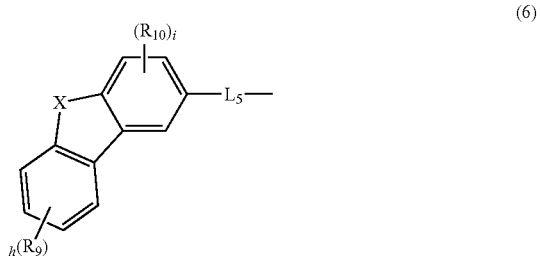
(6)

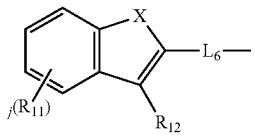
(7)

where: $R_2$ to $R_{11}$ each independently represent a substituted or unsubstituted aryl group having 6 to 50 ring atoms, a substituted or unsubstituted and linear or branched alkyl group having 1 to 50 carbon atoms, a halogen atom, or a cyano group; and $R_1$ and $R_{12}$ each independently represent a hydrogen atom, a substituted or unsubstituted aryl group having 6 to 50 ring atoms, a substituted or unsubstituted and linear or branched alkyl group having 1 to 50 carbon atoms, a halogen atom, or a cyano group;

a represents an integer of 0 to 2; b, c, d, f, h, and j each represent an integer of 0 to 4; and e, g, and i each represent an integer of 0 to 3;

X represents sulfur or oxygen; and $L_1$ and $L_4$ to $L_6$ each independently represent a substituted or unsubstituted arylene group having 6 to 50 ring atoms; and $L_2$ and $L_3$ each independently represent a single bond or a substituted or unsubstituted arylene group having 6 to 50 ring atoms; and where, in the general formula (1), $Ar_1$ to $Ar_3$ which are the groups other than the groups represented by the general formulae (2) to (7) each independently represent a substituted or unsubstituted aryl group having 6 to 50 ring atoms, in which a substituent of the aryl group includes an aryl group having 6 to 50 ring atoms, a linear or branched alkyl group having 1 to 50 carbon atoms, a halogen atom, a cyano group, or a group represented by the following general formula (8):

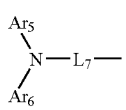
(8)

where: $L_7$ represents a substituted or unsubstituted arylene group having 6 to 50 ring atoms; and $Ar_5$ and $Ar_6$ each independently represent a substituted or unsubstituted aryl group having 6 to 50 ring atoms or a substituted or unsubstituted heteroaryl group having 6 to 50 ring atoms.

Further, the present invention provides an aromatic amine derivative represented by the following general formulae (9) to (12):

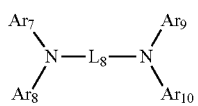
(9)

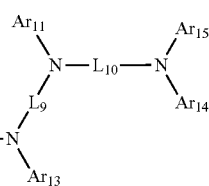
(10)

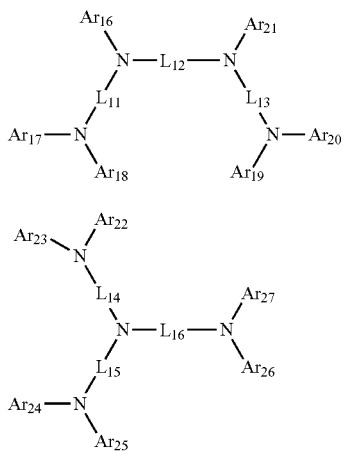
(11)

(12)

where, in the general formula (9): at least one of $Ar_7$ to $Ar_{10}$ is represented by the following general formula (13); and at least one of $Ar_7$ to $Ar_{10}$ is represented by any one of the following general formulae (14) to (18), where, in the general formula (10): at least one of $Ar_{11}$ to $Ar_{15}$ is represented by the following general formula (13); and at least one of $Ar_{11}$ to $Ar_{15}$ is represented by any one of the following general formulae (14) to (18), where, in the general formula (11): at least one of $Ar_{16}$ to $Ar_{21}$ is represented by the following general formula (13); and at least one of $Ar_{16}$ to $Ar_{21}$ is represented by any one of the following general formulae (14) to (18), where, in the general formula (12): at least one of $Ar_{22}$ to $Ar_{27}$ is represented by the following general formula (13); and at least one of $Ar_{22}$ to $Ar_{27}$ is represented by any one of the following general formulae (14) to (18):

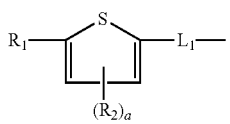
(13)

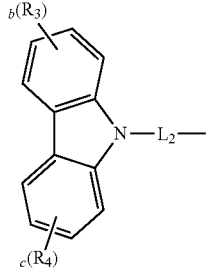
(14)

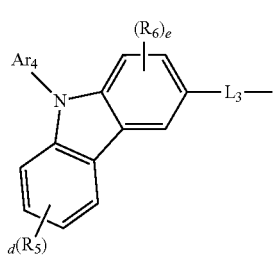
(15)

-continued (16)

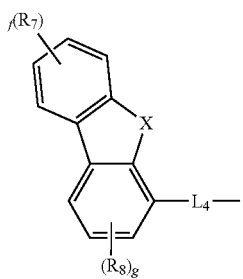

(17)

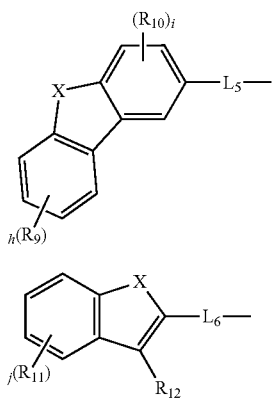

(18)

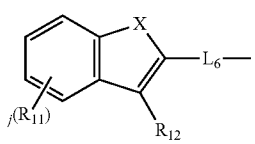

where: $R_2$ to $R_{11}$ each independently represent a substituted or unsubstituted aryl group having 6 to 50 ring atoms, a substituted or unsubstituted and linear or branched alkyl group having 1 to 50 carbon atoms, a halogen atom, or a cyano group; and $R_1$ and $R_{12}$ each independently represent a hydrogen atom, a substituted or unsubstituted aryl group having 6 to 50 ring atoms, a substituted or unsubstituted and linear or branched alkyl group having 1 to 50 carbon atoms, a halogen atom, or a cyano group;

a represents an integer of 0 to 2; b, c, d, f, h, and j each represent an integer of 0 to 4; and e, g, and i each represent an integer of 0 to 3;

X represents sulfur or oxygen; and $L_1$ and $L_4$ to $L_6$ each independently represent a substituted or unsubstituted arylene group having 6 to 50 ring atoms; and $L_2$ and $L_3$ each independently represent a single bond or a substituted or unsubstituted arylene group having 6 to 50 ring atoms; and where, in the general formulae (9) to (12): $Ar_7$ to $Ar_{27}$ which are the groups other than the groups represented by the general formulae (14) to (18) each independently represent a substituted or unsubstituted aryl group having 6 to 50 ring atoms; and $L_8$ to $L_{16}$ each independently represent a substituted or unsubstituted arylene group having 6 to 50 ring carbon atoms.

Further, the present invention provides an organic EL device including an organic thin film layer interposed between a cathode and an anode and formed of one layer or a plurality of layers including at least a light emitting layer, in which at least one layer of the organic thin film layers contains the aromatic amine derivative alone or as a component of a mixture.

Effects of the Invention

An aromatic amine derivative of the present invention provides an organic EL device in which a molecule hardly crystallizes, and which decreases a driving voltage when used as a material for the organic EL device, has a long lifetime, and can be produced with improved yields upon the production of the organic EL device.

BEST MODE FOR CARRYING OUT THE INVENTION

An aromatic amine derivative of the present invention is represented by the following general formula (1):

(1)

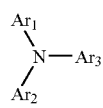

where: at least one of $Ar_1$ to $Ar_3$ is represented by the following general formula (2); and at least one of $Ar_1$ to $Ar_3$ is represented by any one of the following general formulae (3) to (7):

(2)

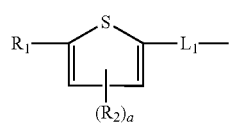

(3)

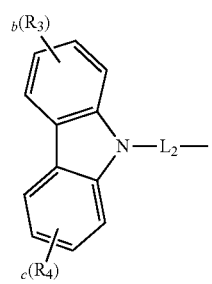

(4)

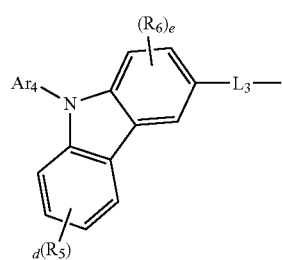

(5)

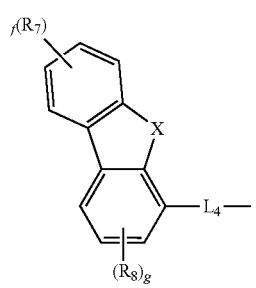

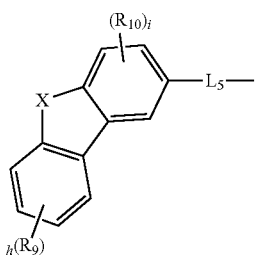
(6)

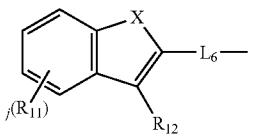
(7)

where: $R_2$ to $R_{11}$ each independently represent a substituted or unsubstituted aryl group having 6 to 50 ring atoms, a substituted or unsubstituted and linear or branched alkyl group having 1 to 50 carbon atoms, a halogen atom, or a cyano group; and $R_1$ and $R_{12}$ each independently represent a hydrogen atom, a substituted or unsubstituted aryl group having 6 to 50 ring atoms, a substituted or unsubstituted and linear or branched alkyl group having 1 to 50 carbon atoms, a halogen atom, or a cyano group;

a represents an integer of 0 to 2; b, c, d, f, h, and j each represent an integer of 0 to 4; and e, g, and i each represent an integer of 0 to 3;

X represents sulfur or oxygen; and $L_1$ and $L_4$ to $L_6$ each independently represent a substituted or unsubstituted arylene group having 6 to 50 ring atoms; and $L_2$ and $L_3$ each independently represent a single bond or a substituted or unsubstituted arylene group having 6 to 50 ring atoms; and where, in the general formula (1), $Ar_1$ to $Ar_3$ which are the groups other than the groups represented by the general formulae (2) to (7) each independently represent a substituted or unsubstituted aryl group having 6 to 50 ring atoms, in which a substituent of the aryl group includes an aryl group having 6 to 50 ring atoms, a linear or branched alkyl group having 1 to 50 carbon atoms, a halogen atom, a cyano group, or a group represented by the following general formula (8):

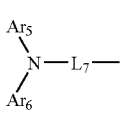
(8)

where: $L_7$ represents a substituted or unsubstituted arylene group having 6 to 50 ring atoms; and $Ar_5$ and $Ar_6$ each independently represent a substituted or unsubstituted aryl group having 6 to 50 ring atoms or a substituted or unsubstituted heteroaryl group having 6 to 50 ring atoms.

In the aromatic amine derivative of the present invention represented by the general formula (1), it is preferred that $Ar_1$ be represented by the general formula (2) and $Ar_2$ and $Ar_3$ be each represented by any one of the general formulae (2) to (7).

In the aromatic amine derivative of the present invention represented by the general formula (1), it is preferred that, in the general formula (1), $Ar_1$ and $Ar_2$ be each represented by the general formula (2) and $Ar_3$ be represented by any one of the general formulae (2) to (7).

In the aromatic amine derivative of the present invention represented by the general formula (1), it is preferred that, in the general formula (2): $L_1$ represent a phenylene group, a biphenylene group, or a fluorenylene group; $R_1$ represent a phenyl group, a naphthyl group, or a phenanthrenyl group; and a represent 0.

Further, the aromatic amine derivative of the present invention is represented by the following general formulae (9) to (12):

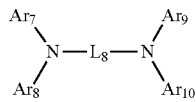
(9)

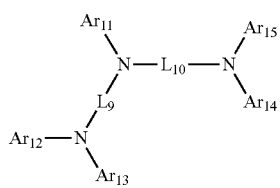
(10)

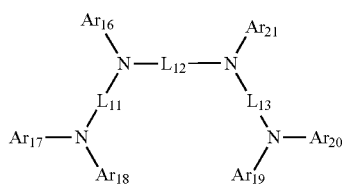
(11)

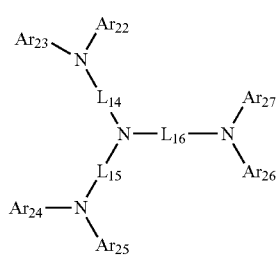
(12)

where, in the general formula (9): at least one of $Ar_7$ to $Ar_{10}$ is represented by the following general formula (13); and at least one of $Ar_7$ to $Ar_{10}$ is represented by any one of the following general formulae (14) to (18), where, in the general formula (10): at least one of $Ar_{11}$ to $Ar_{15}$ is represented by the following general formula (13); and at least one of $Ar_{11}$ to $Ar_{15}$ is represented by any one of the following general formulae (14) to (18), where, in the general formula (11): at least one of $Ar_{16}$ to $Ar_{21}$ is represented by the following general formula (13); and at least one of $Ar_{16}$ to $Ar_{21}$ is represented by any one of the following general formulae (14) to (18), where, in the general formula (12): at least one of $Ar_{22}$ to $Ar_{27}$ is represented by the following general formula (13); and at least one of $Ar_{22}$ to $Ar_{27}$ is represented by any one of the following general formulae (14) to (18):

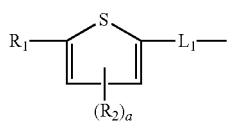
(13)

-continued

(14)
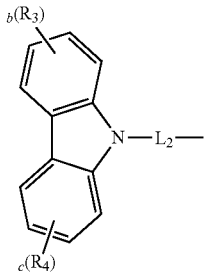

(15)
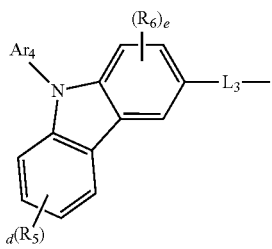

(16)
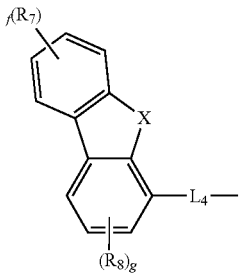

(17)
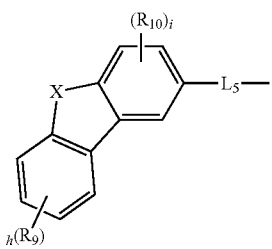

(18)
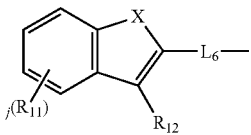

where: $R_2$ to $R_{11}$ each independently represent a substituted or unsubstituted aryl group having 6 to 50 ring atoms, a substituted or unsubstituted and linear or branched alkyl group having 1 to 50 carbon atoms, a halogen atom, or a cyano group; and $R_1$ and $R_{12}$ each independently represent a hydrogen atom, a substituted or unsubstituted aryl group having 6 to 50 ring atoms, a substituted or unsubstituted and linear or branched alkyl group having 1 to 50 carbon atoms, a halogen atom, or a cyano group;

a represents an integer of 0 to 2; b, c, d, f, h, and j each represent an integer of 0 to 4; and e, g, and i each represent an integer of 0 to 3;

X represents sulfur or oxygen; and $L_1$ and $L_4$ to $L_6$ each independently represent a substituted or unsubstituted arylene group having 6 to 50 ring atoms; and $L_2$ and $L_3$ each independently represent a single bond or a substituted or unsubstituted arylene group having 6 to 50 ring atoms; and where, in the general formulae (9) to (12): $Ar_7$ to $Ar_{27}$ which are the groups other than the groups represented by the general formulae (14) to (18) each independently represent a substituted or unsubstituted aryl group having 6 to 50 ring atoms; and $L_8$ to $L_{16}$ each independently represent a substituted or unsubstituted arylene group having 6 to 50 ring carbon atoms.

In the aromatic amine derivative of the present invention represented by the general formula (9), it is preferred that $Ar_7$ and $Ar_8$ be each represented by the general formula (13) and $Ar_9$ and $Ar_{10}$ be each represented by any one of the general formulae (14) to (18). Further, it is preferred that $Ar_7$ and $Ar_9$ be each represented by the general formula (13) and $Ar_8$ and $Ar_{10}$ be each represented by any one of the general formulae (14) to (18).

In the aromatic amine derivative of the present invention represented by the general formula (10), it is preferred that $Ar_{11}$ be represented by the general formula (13) and $Ar_{13}$ and $Ar_{14}$ be each represented by anyone of the general formulae (14) to (18). Further, it is preferred that $Ar_{13}$ and $Ar_{14}$ be each represented by the general formula (13) and $Ar_{11}$ be represented by any one of the general formulae (14) to (18).

In the aromatic amine derivative of the present invention represented by the general formula (11), it is preferred that $Ar_{16}$ and $Ar_{21}$ be each represented by the general formula (13) and $Ar_{18}$ and $Ar_{19}$ be each represented by any one of the general formulae (14) to (18). Further, it is preferred that $Ar_{18}$ and $Ar_{19}$ be each represented by the general formula (13) and $Ar_{16}$ and $Ar_{21}$ be each represented by any one of the general formulae (14) to (18).

In the aromatic amine derivative of the present invention represented by the general formula (12), it is preferred that $Ar_{22}$, $Ar_{24}$, and $Ar_{26}$ be each represented by the general formula (13) and $Ar_{23}$, $Ar_{25}$, and $Ar_{27}$ be each represented by any one of the general formulae (14) to (18).

In the aromatic amine derivative of the present invention represented by the general formulae (9) to (12), it is preferred that, in the general formula (13): $L_1$ represent a phenylene group, a biphenylene group, or a fluorenylene group; $R_1$ represent a phenyl group, a naphthyl group, or a phenanthrenyl group; and a represent 0.

In the aromatic amine derivative of the present invention represented by the general formulae (9) to (12), it is preferred that $Ar_7$ to $Ar_{27}$ each independently represent a phenyl group, a naphthyl group, a biphenyl group, a terphenyl group, or a fluorenyl group. Further, it is preferred that $L_8$ to $L_{16}$ each independently represent a phenylene group, a naphthylene group, a biphenylene group, a terphenylene group, or a fluorenylene group.

Examples of the substituted or unsubstituted aryl group having 6 to 50 ring atoms represented by $Ar_1$ to $Ar_{27}$ and $R_1$ to $R_{12}$ in the general formulae (1) to (18) include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group, a fluoranthenyl group, and a fluorenyl group.

Of those, a phenyl group, a naphthyl group, a biphenylyl group, a terphenylyl group, a fluorenyl group, and a phenanthrenyl group are preferable.

A thiophene compound has high reactivity at 2- and 5-positions thereof; thus, it is preferable to protect those substitution positions. As a known document, Macromol. Rapid Commun., 2001, 22, 266-270 is given, which reports that the polymerization proceeds under electrically unstable conditions. An alkyl group or an aryl group is preferable as a substituent, and from a viewpoint of the stability of the compound, an aryl group is preferable and an unsubstituted aryl group is further preferable.

Examples of the substituted or unsubstituted arylene group having 6 to 50 ring atoms represented by $L_1$ to $L_{16}$ in the general formulae (2) to (18) include those in which the examples of the aryl group are each made into a divalent group.

Examples of the substituted or unsubstituted heteroaryl group having 6 to 50 represented by $Ar_5$ and $Ar_6$ in the general formula (8) include a 1-pyrrolyl group, a 2-pyrrolyl group, a 3-pyrrolyl group, a pyradinyl group, a 2-pyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenadinyl group, a 2-phenadinyl group, a 1-phenothiazinyl group, a 2-phenothiazinyl group, a 3-phenothiazinyl group, a 4-phenothiazinyl group, a 10-phenothiazinyl group, a 1-phenoxazinyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, a 4-t-butyl-3-indolyl group, a thiophenyl group, a 1-phenylthiophenyl group, a 1,4-diphenylthiophenyl group, a benzothiophenyl group, a 1-phenylbenzothiophenyl group, a 1-phenyldibenzothiophenyl group, a dibenzofuranyl group, a 1-phenyldibenzofuranyl group, and a benzothiazolyl group.

Of those, 1-phenylthiophenylyl group, a 1-phenylbenzothiophenylyl group, a 1-phenyldibenzofuranyl group, and a benzothiazolyl group are preferable.

Examples of the substituted or unsubstituted alkyl group having 1 to 50 carbon atoms represented by $R_1$ to $R_{12}$ in the general formulae (1) to (18) include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a trifluoromethyl group, a cyclopropyl group, a cyclobutyl group, a cyclopentyl group, a cyclohexyl group, a 4-methylcyclohexyl group, a 1-adamantyl group, a 2-adamantyl group, a 1-norbornyl group, and a 2-norbornyl group. Preferred is a saturated and linear, branched, or cyclic alkyl group, and specific examples thereof include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a cyclopropyl group, a cyclobutyl group, a cyclopentyl group, a cyclohexyl group, a 4-methylcyclohexyl group, a 1-adamantyl group, a 2-adamantyl group, a 1-norbornyl group, and a 2-norbornyl group.

Examples of the halogen atom represented by $R_1$ to $R_{12}$ in the general formulae (2) to (7) and (13) to (18) include a fluorine atom, a chlorine atom, a bromine atom, and an iodine atom.

Examples of the aryl group having 6 to 50 ring atoms, the linear or branched alkyl group having 1 to 50 carbon atoms, and the halogen atom, each of which is a substituent of $Ar_1$ to $Ar_3$ in the general formula (1), include the same groups as exemplified for the aryl group, the alkyl group, and the halogen atom which are mentioned above, respectively.

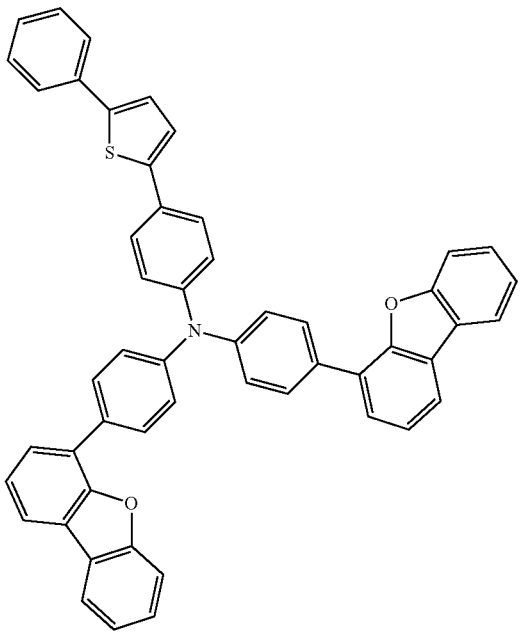

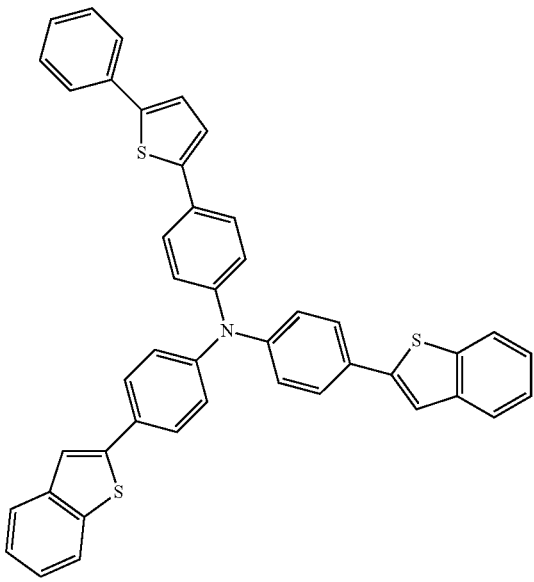

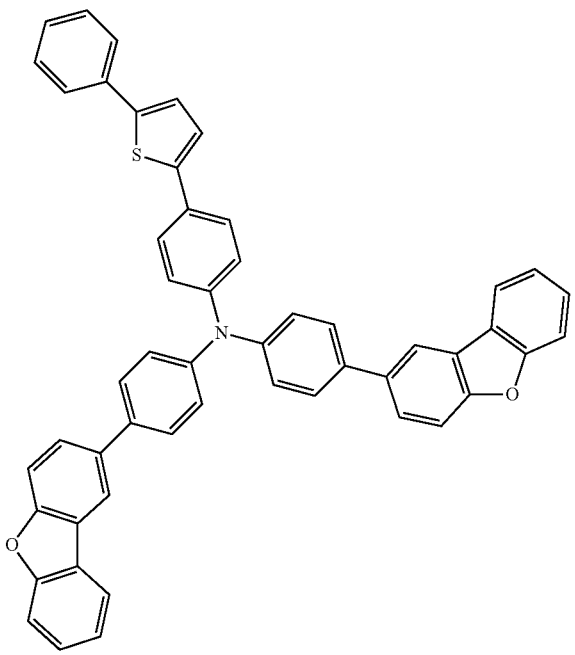

-continued
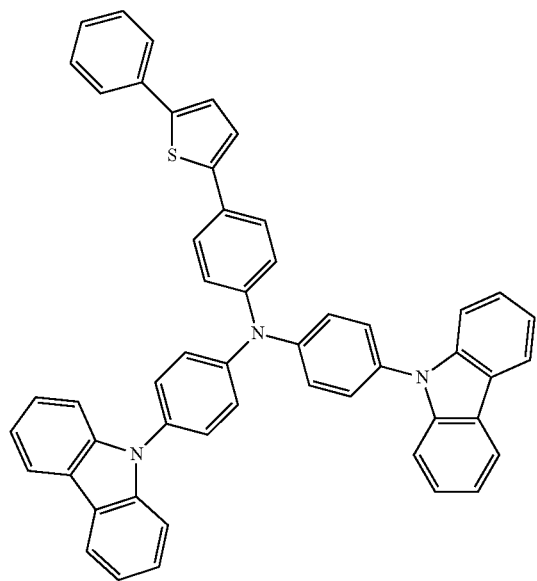
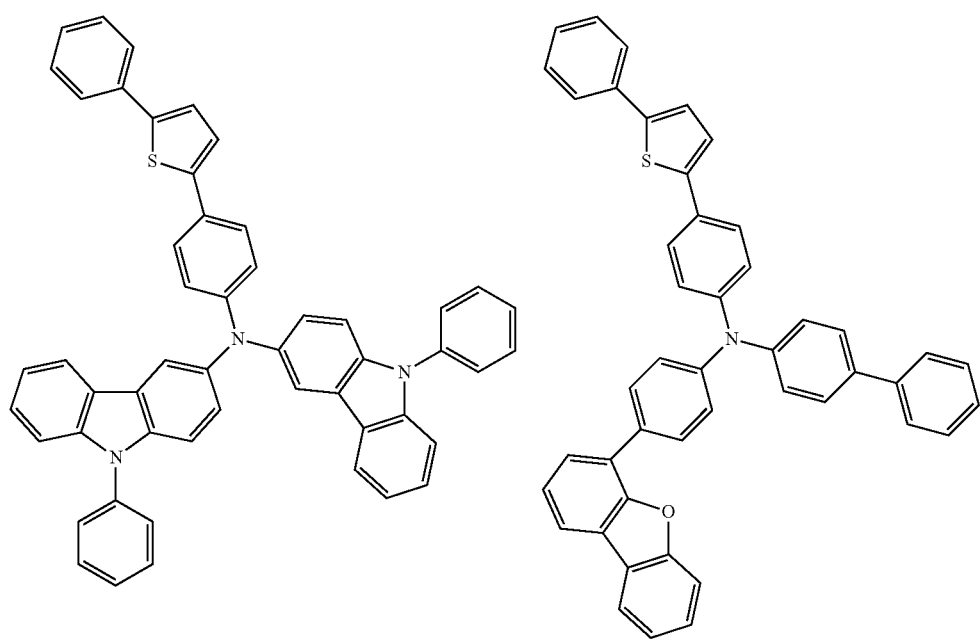

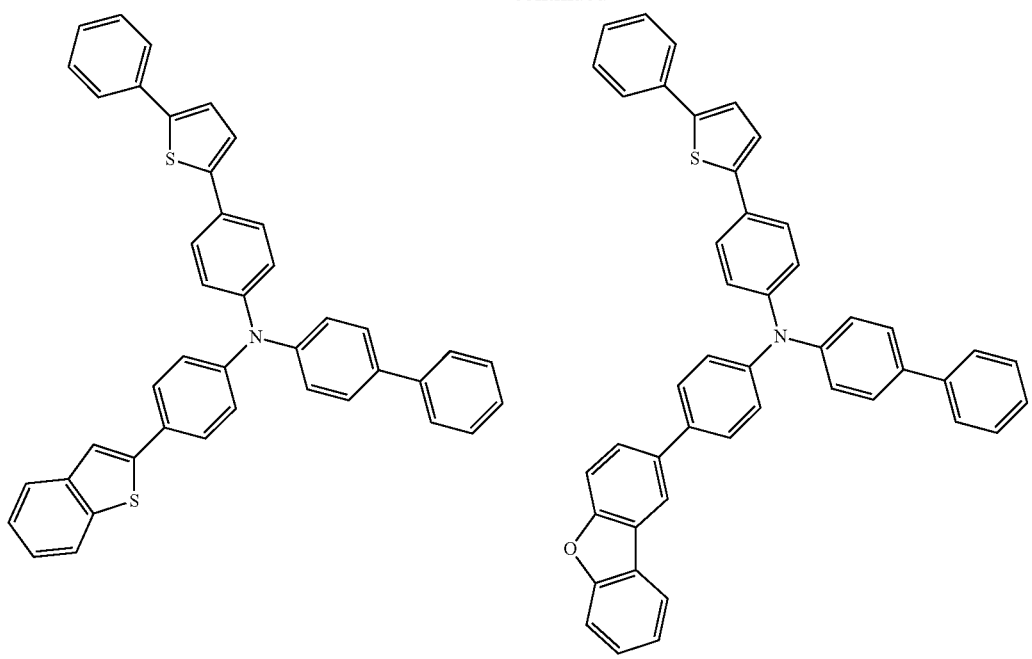
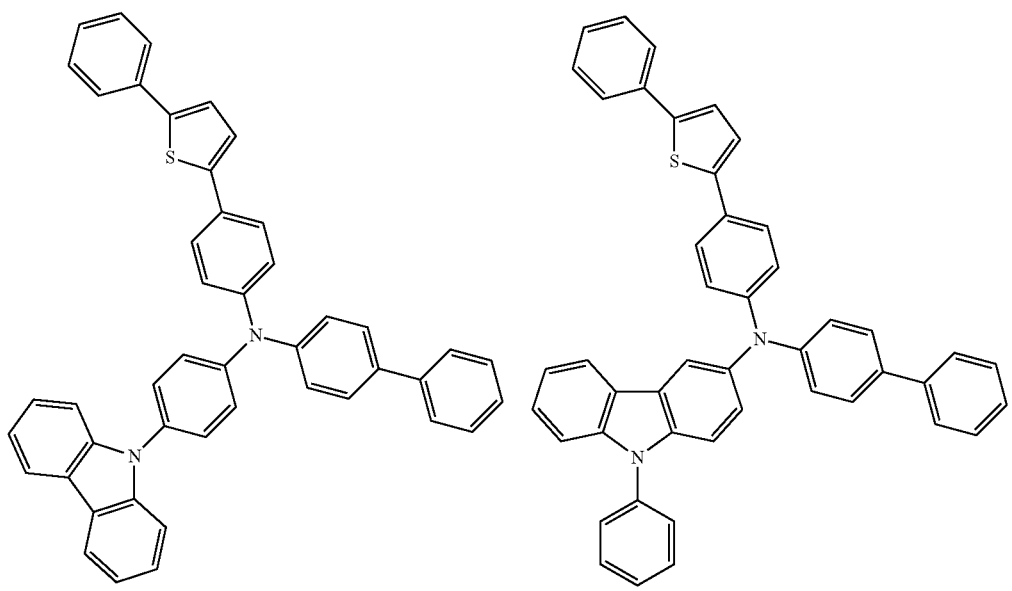

21
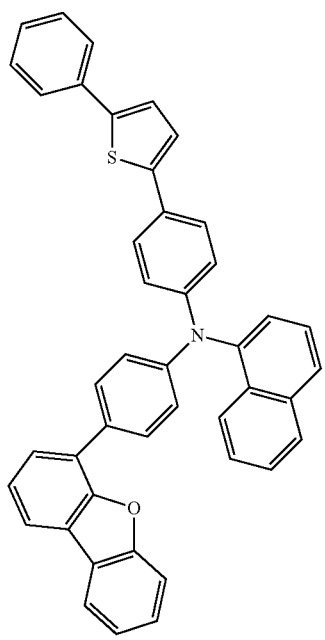
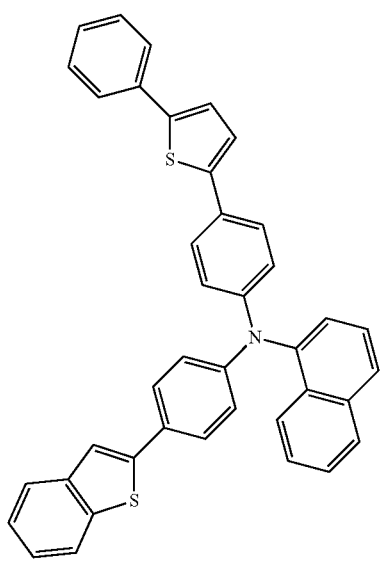
22
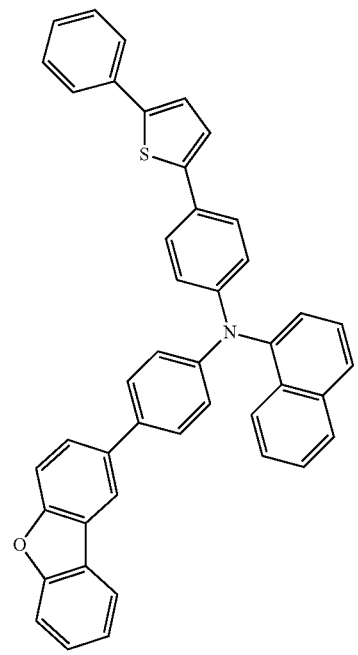
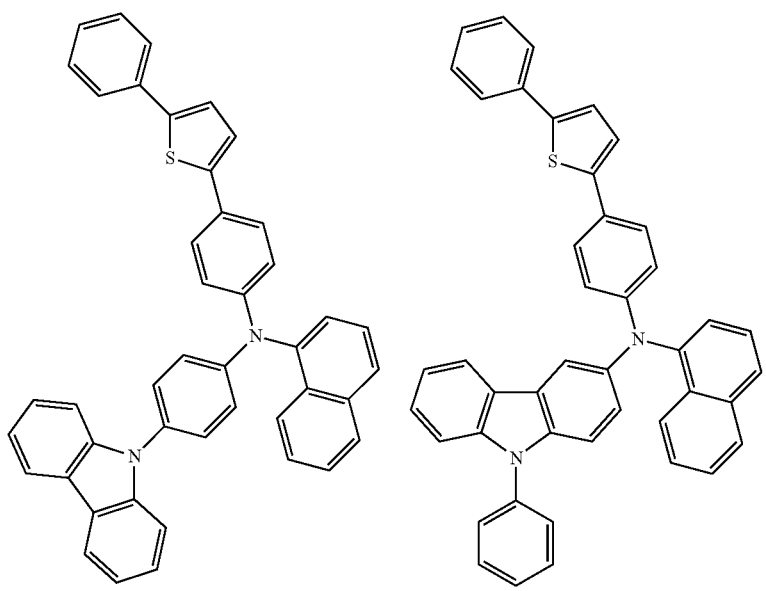

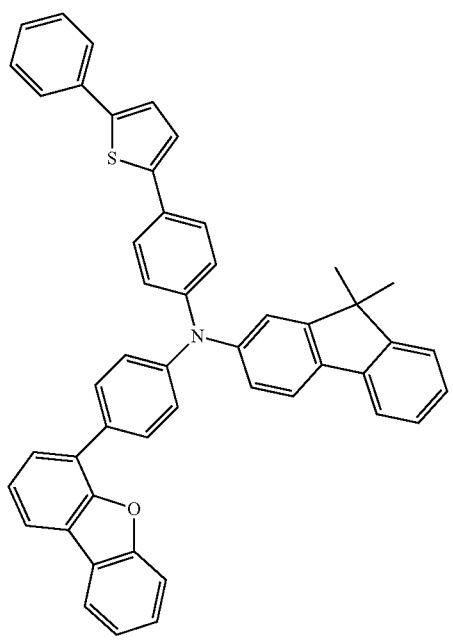
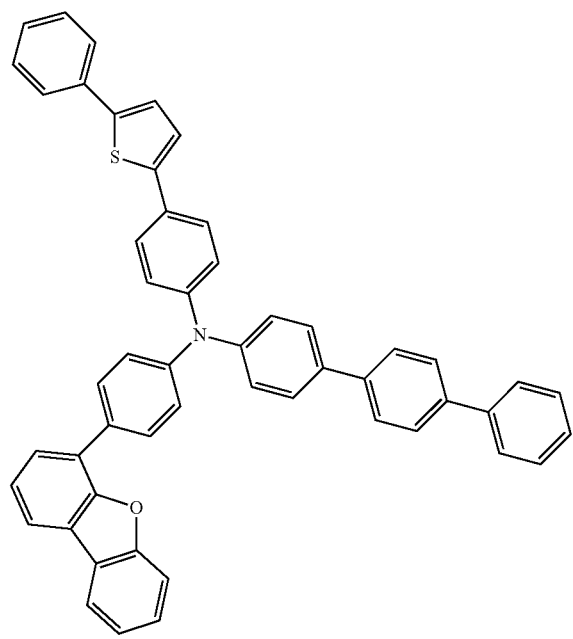
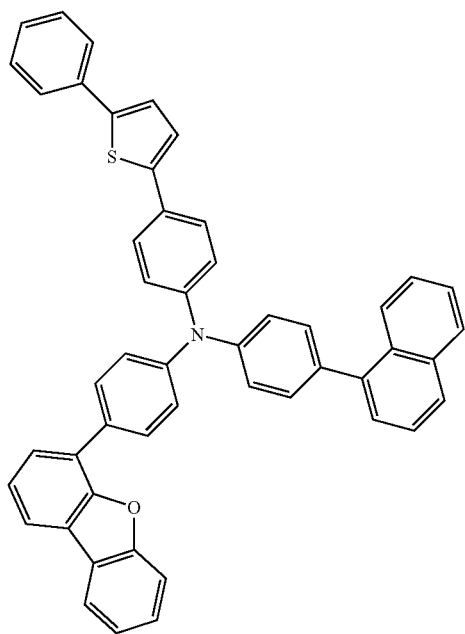
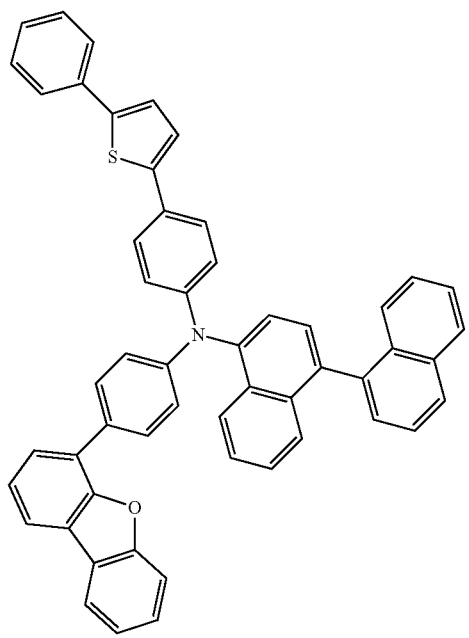

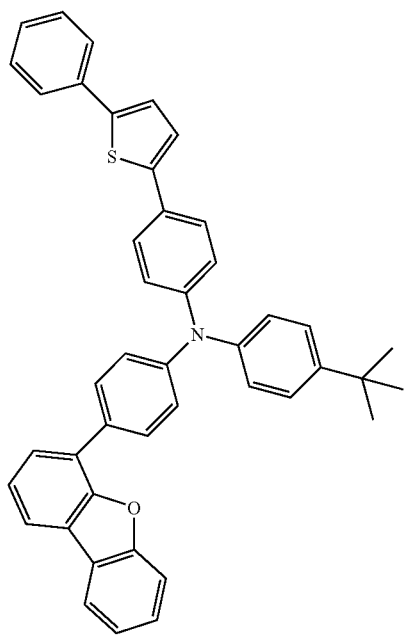
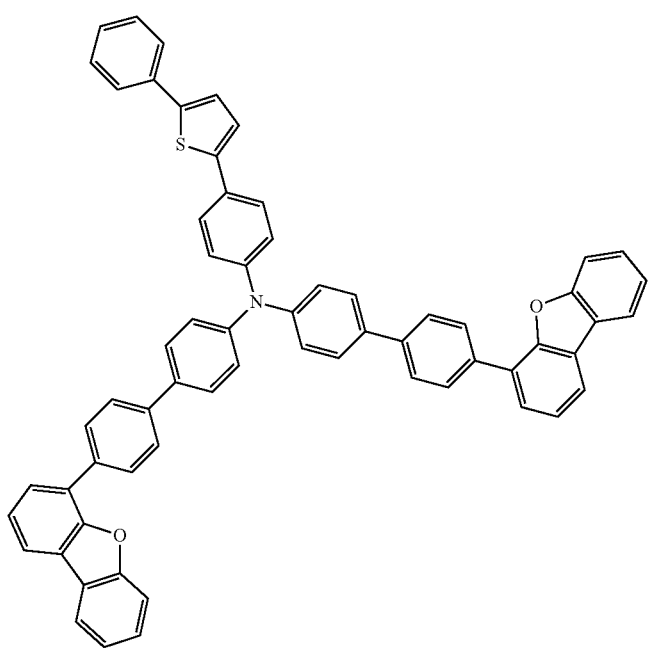

-continued
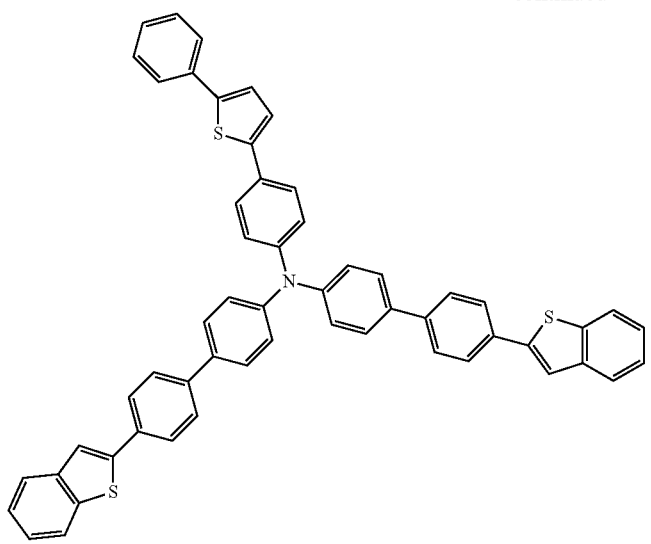
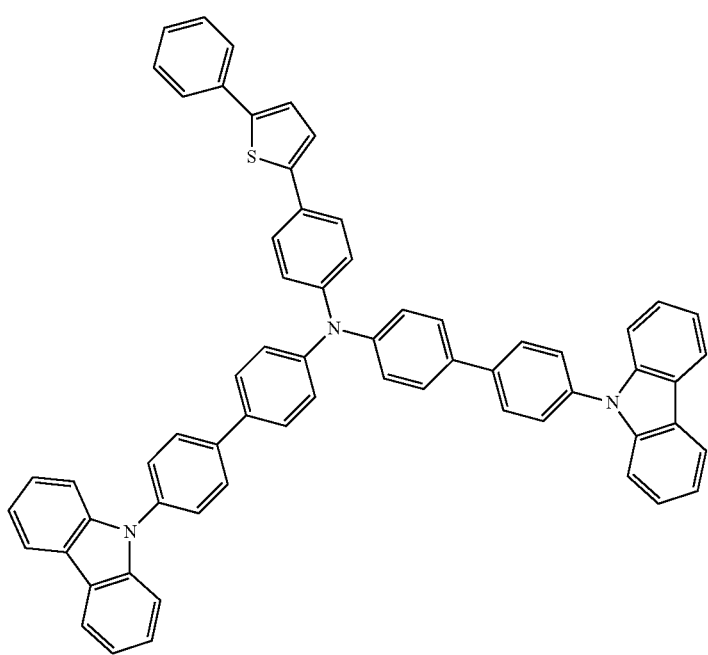

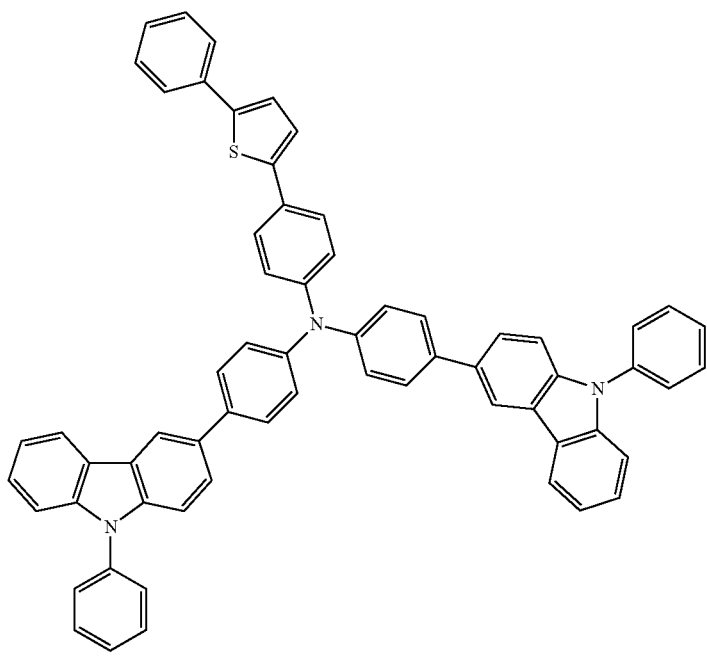
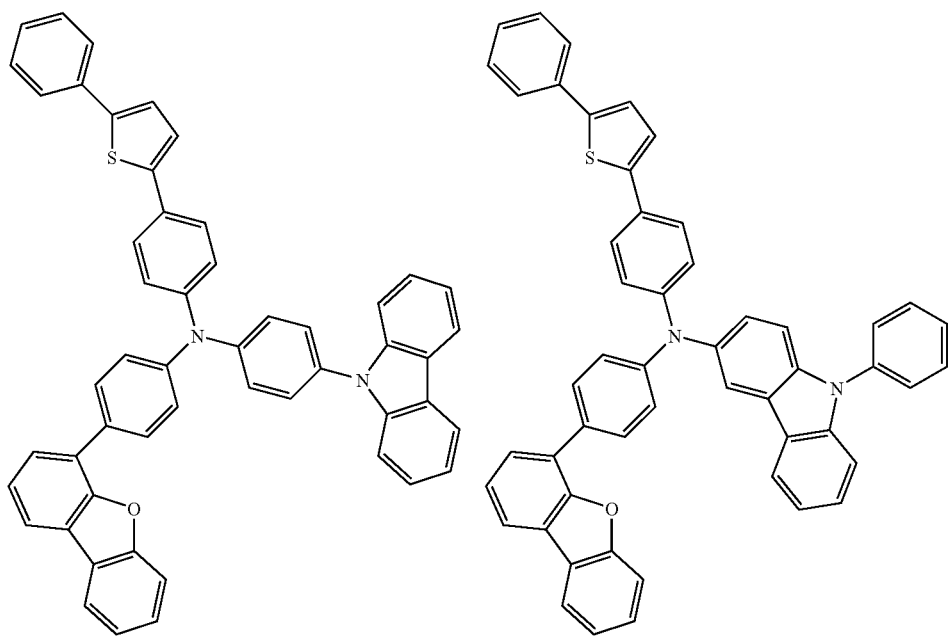

-continued
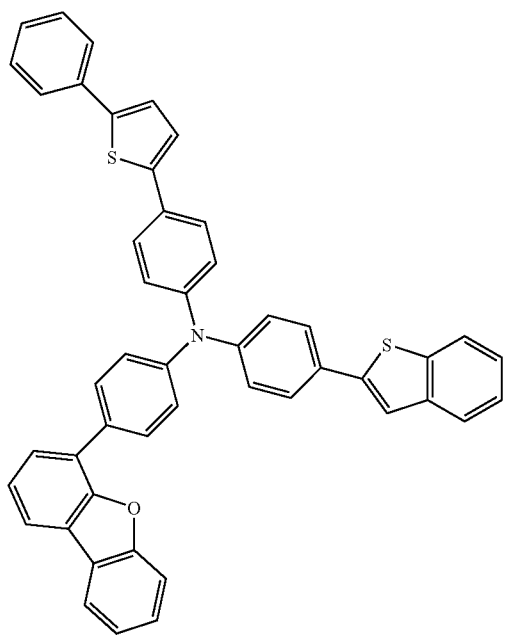
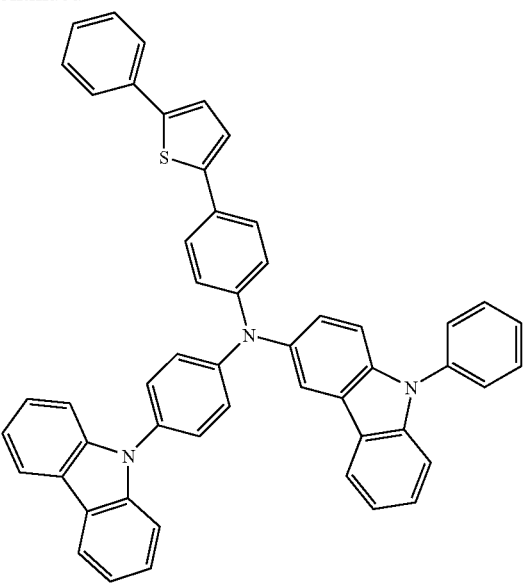
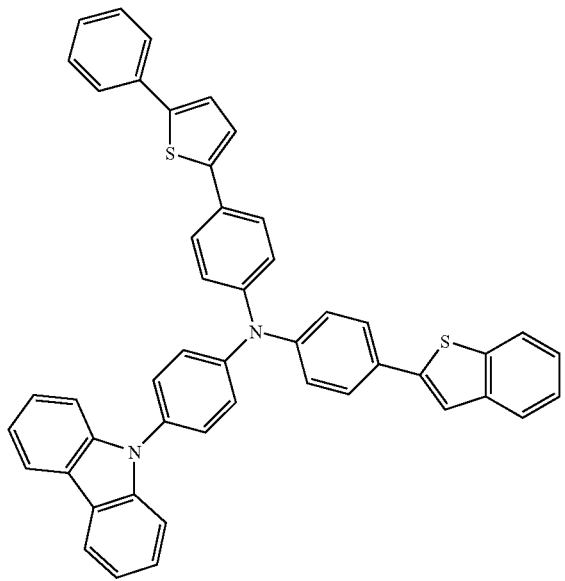
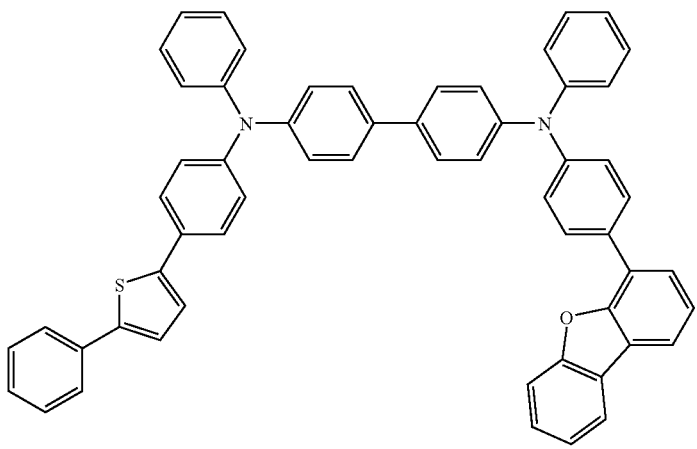

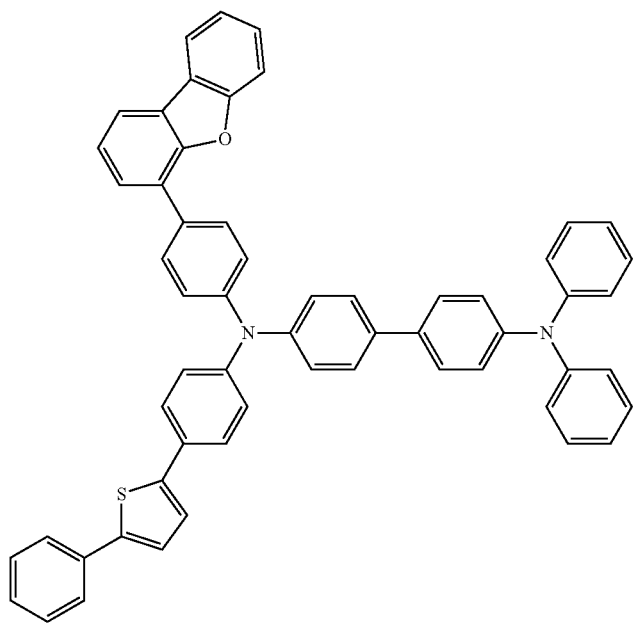
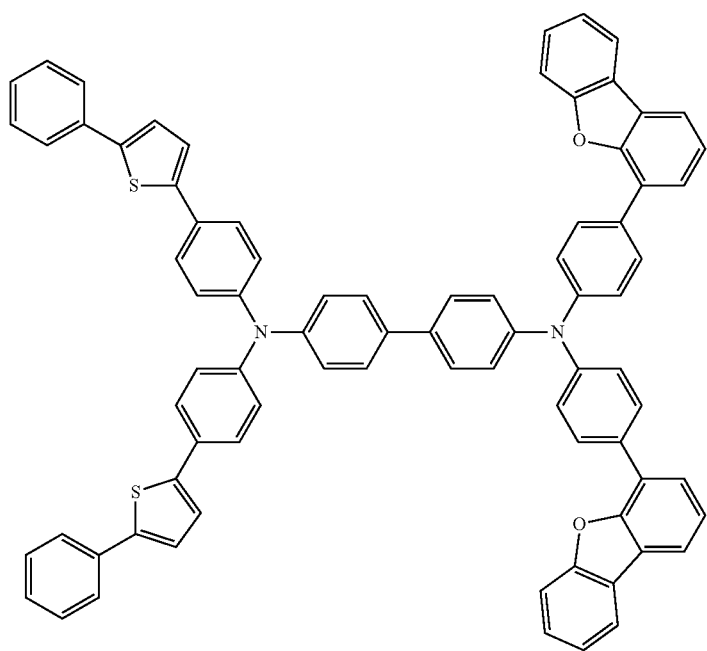

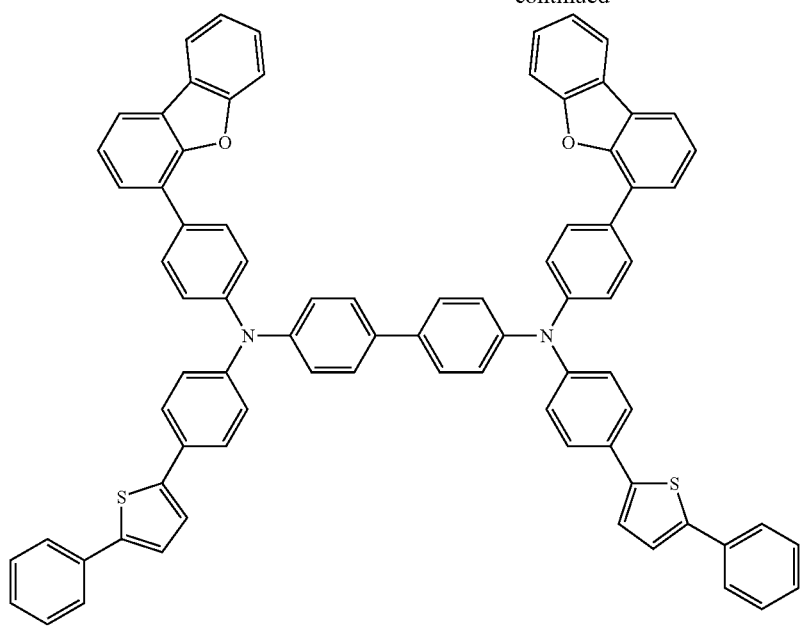
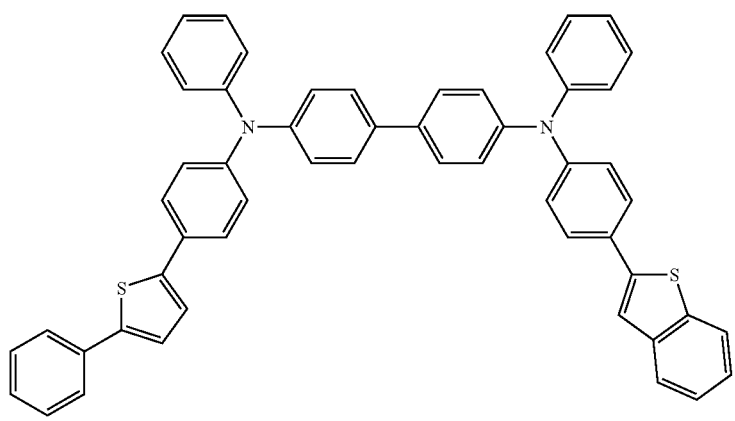
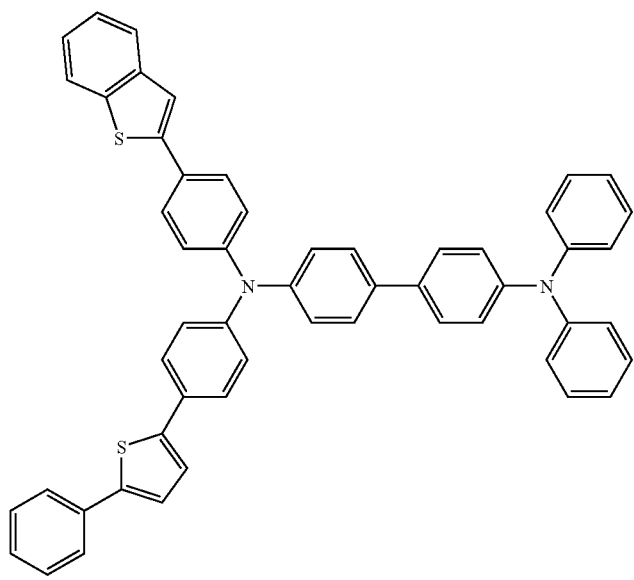

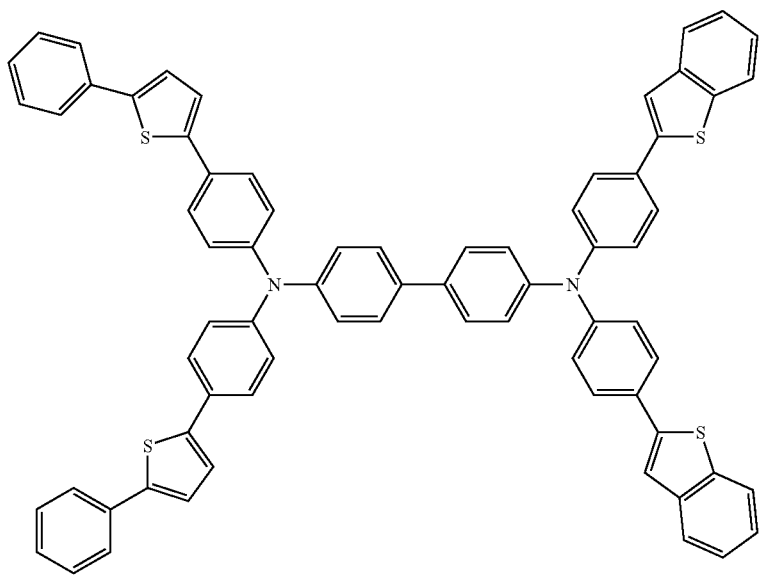
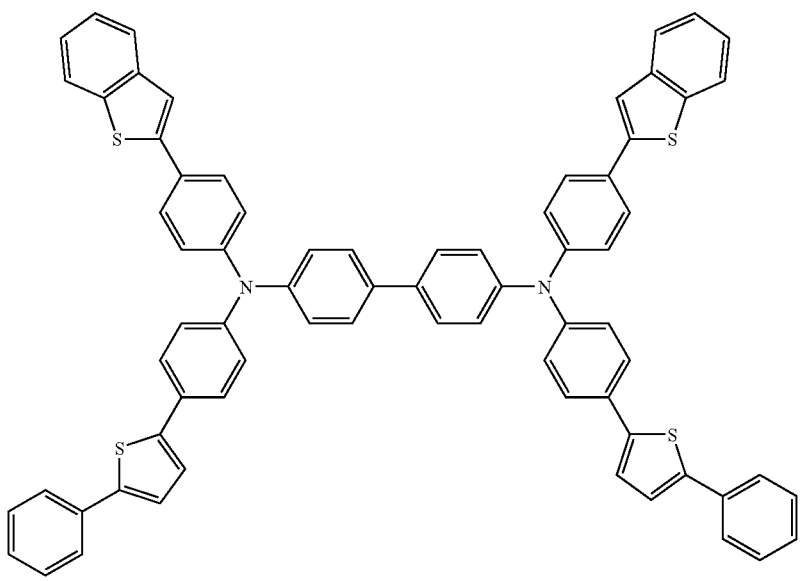
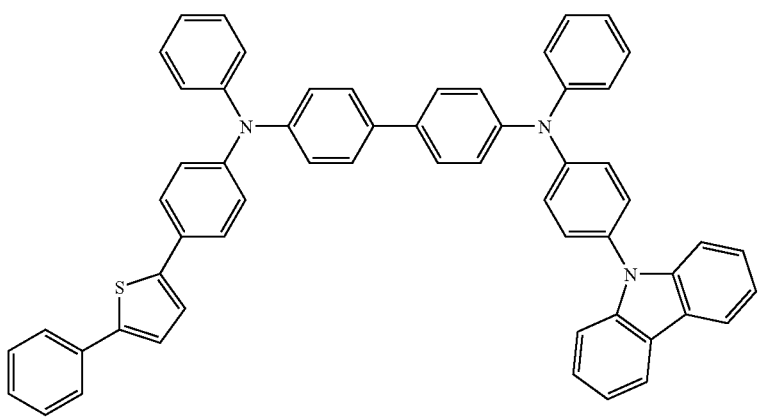

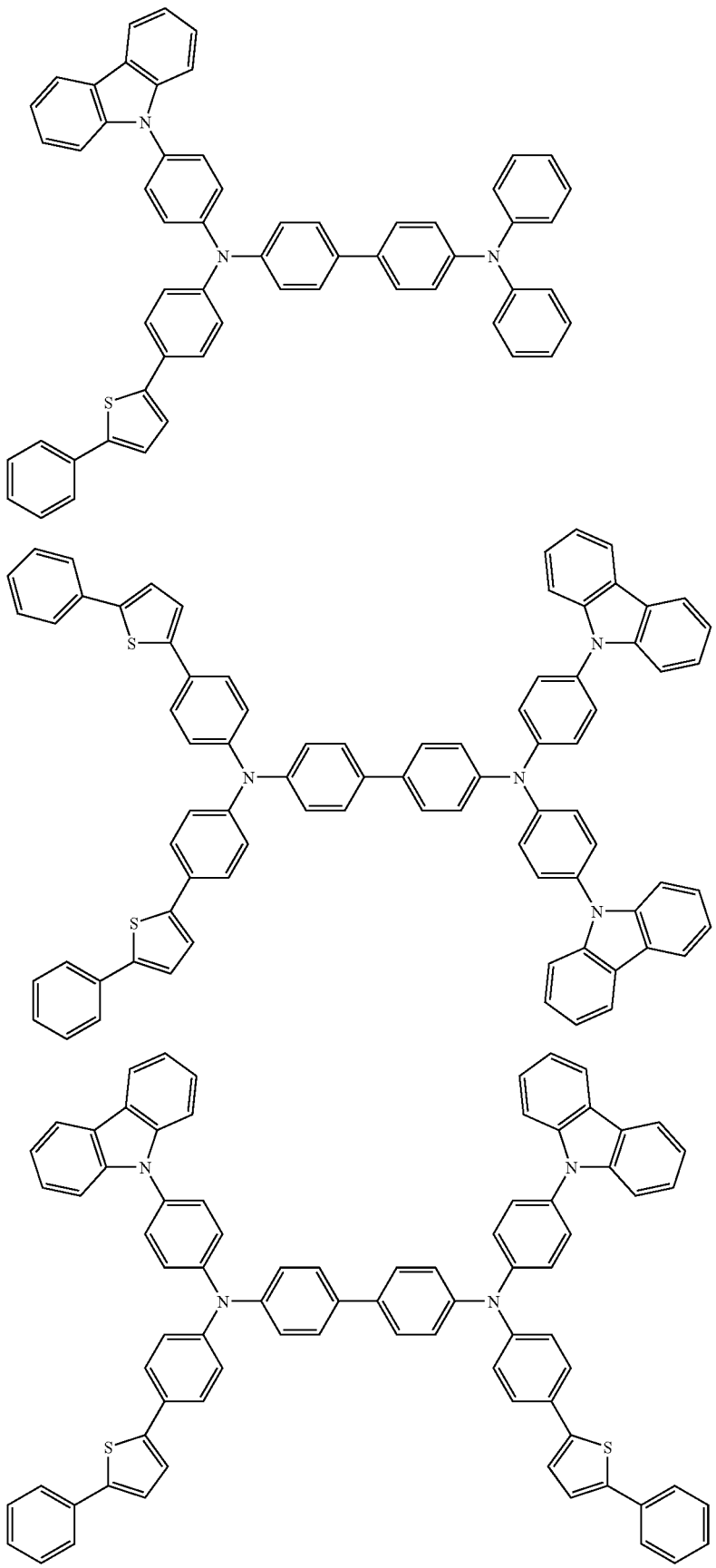

-continued
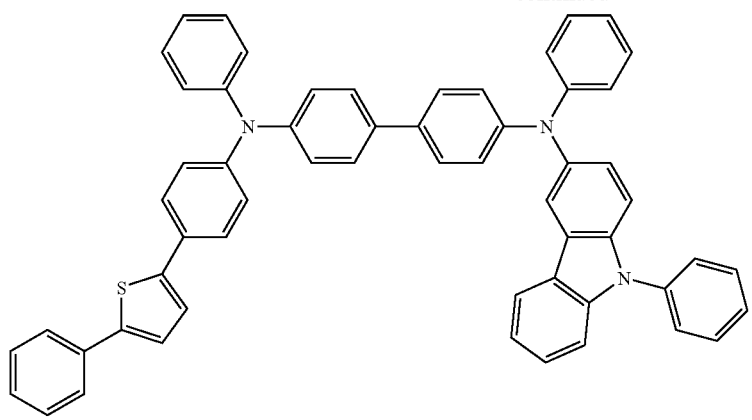
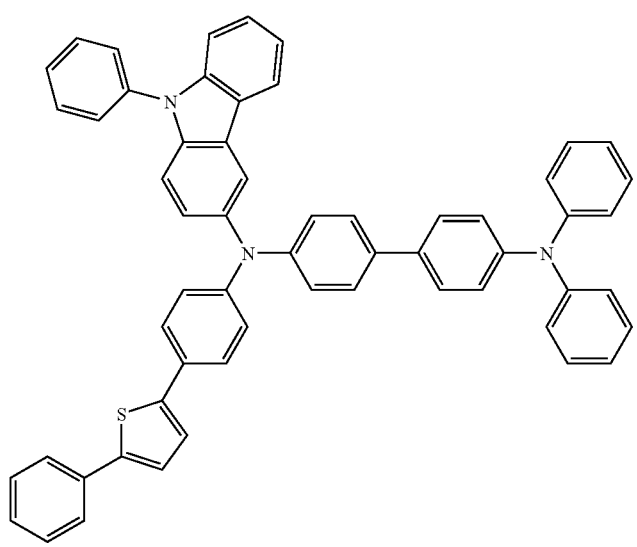
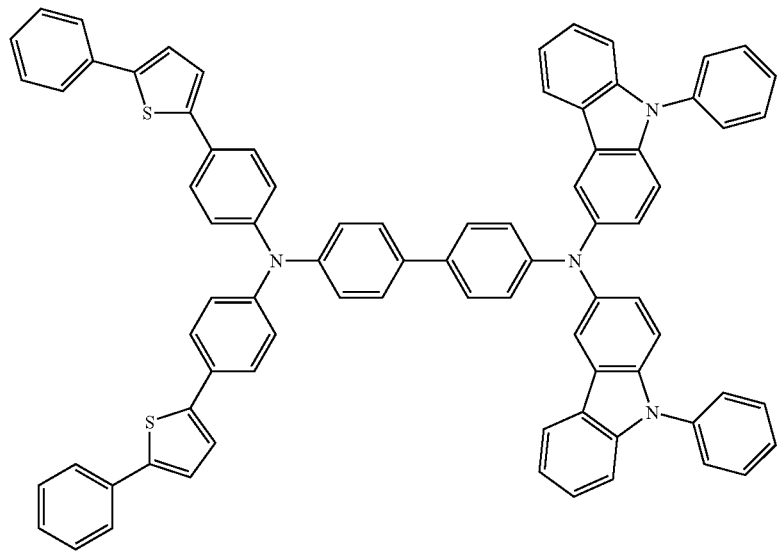

-continued
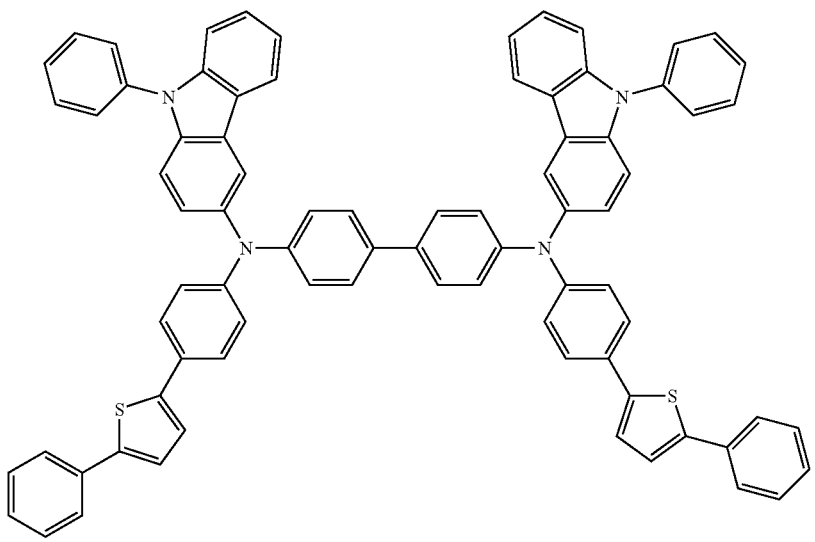
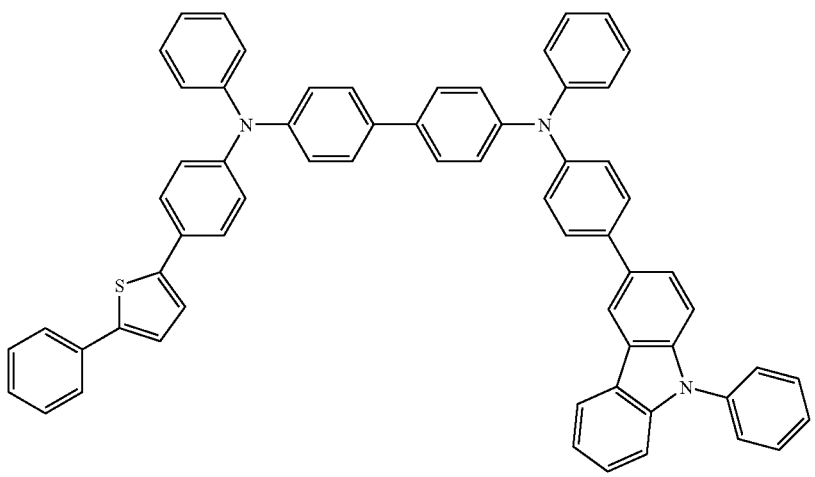
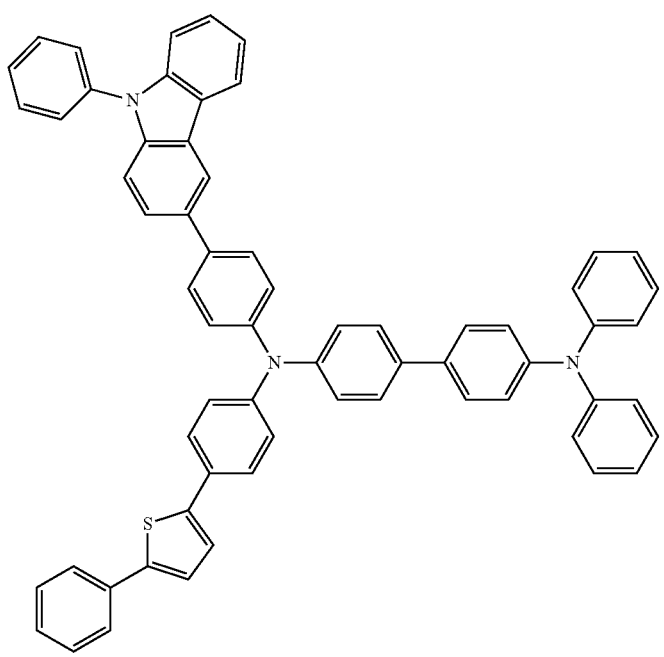

-continued
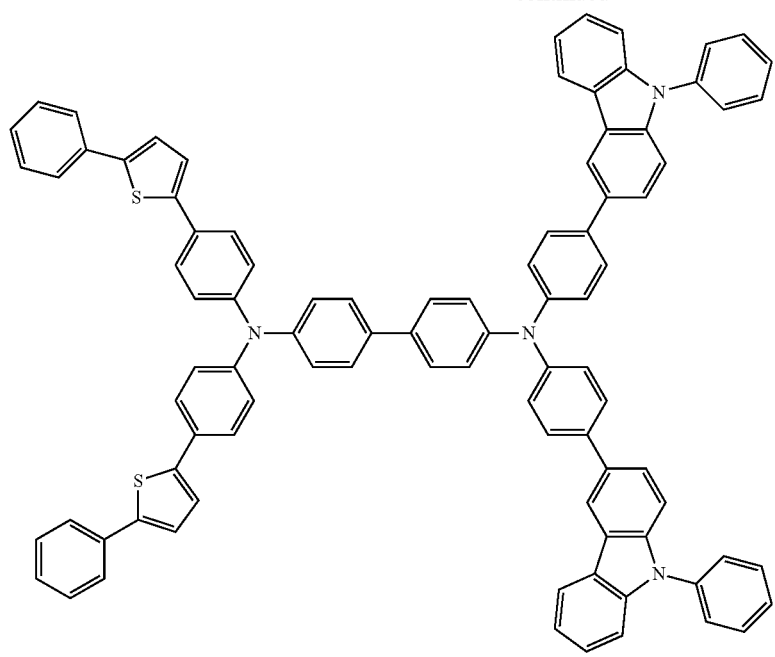
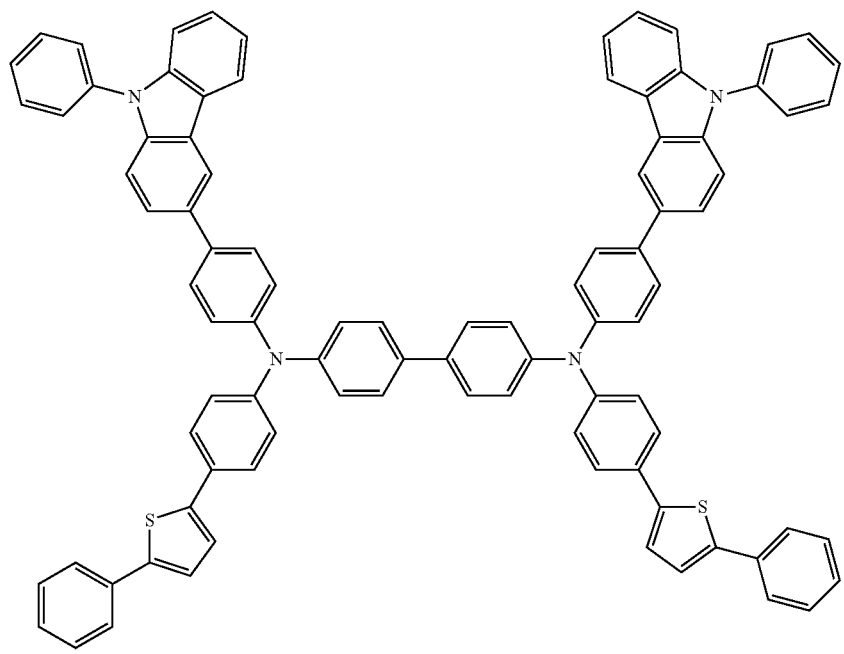

-continued
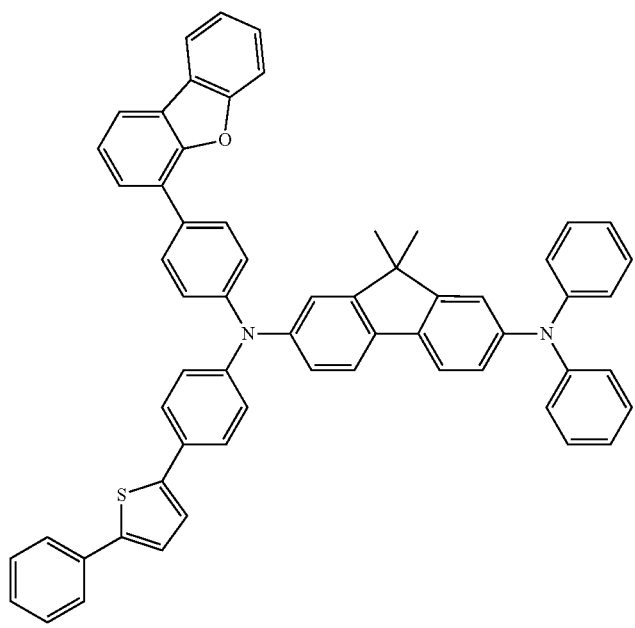
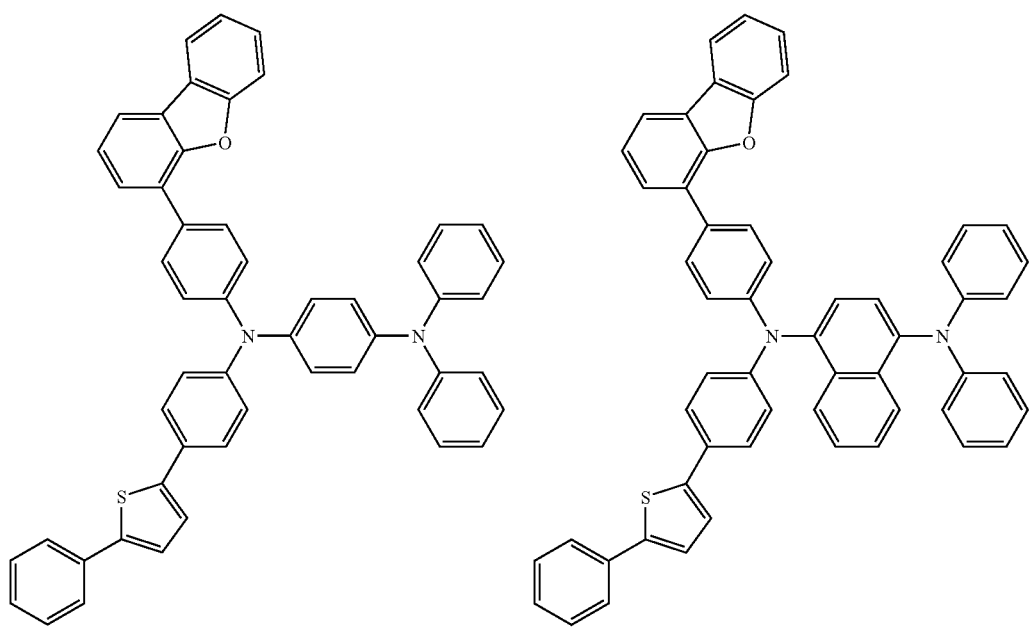

-continued
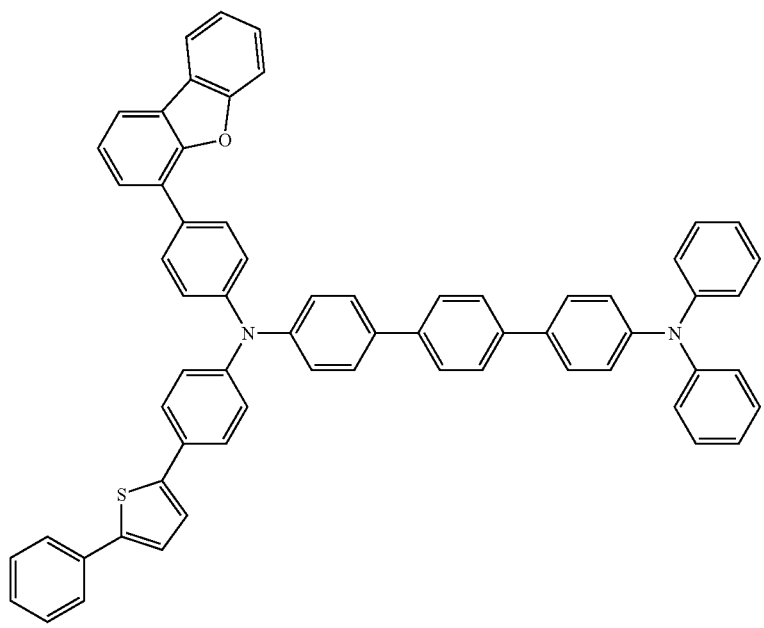
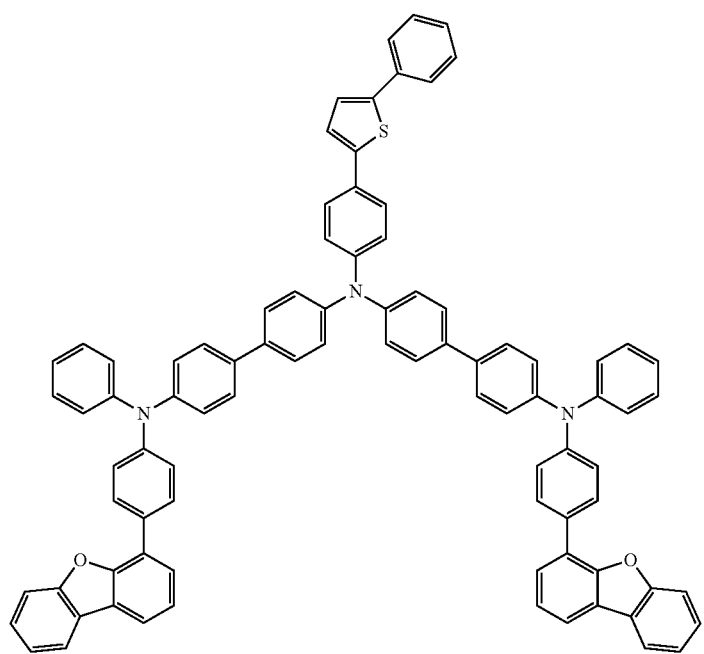

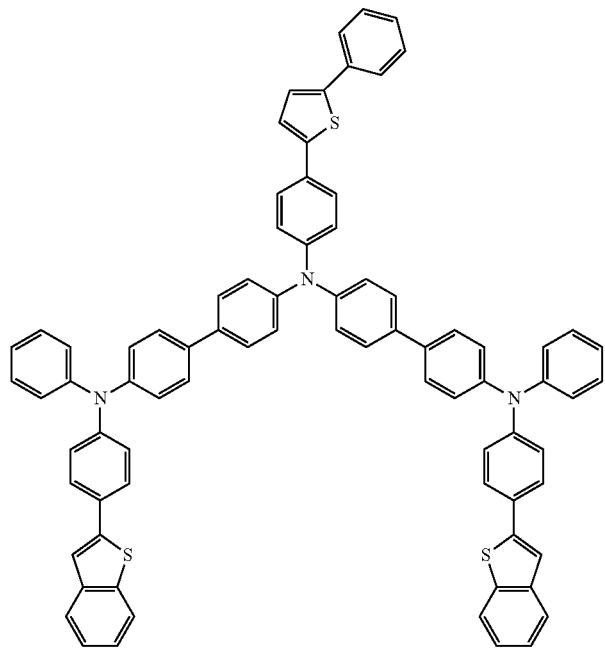
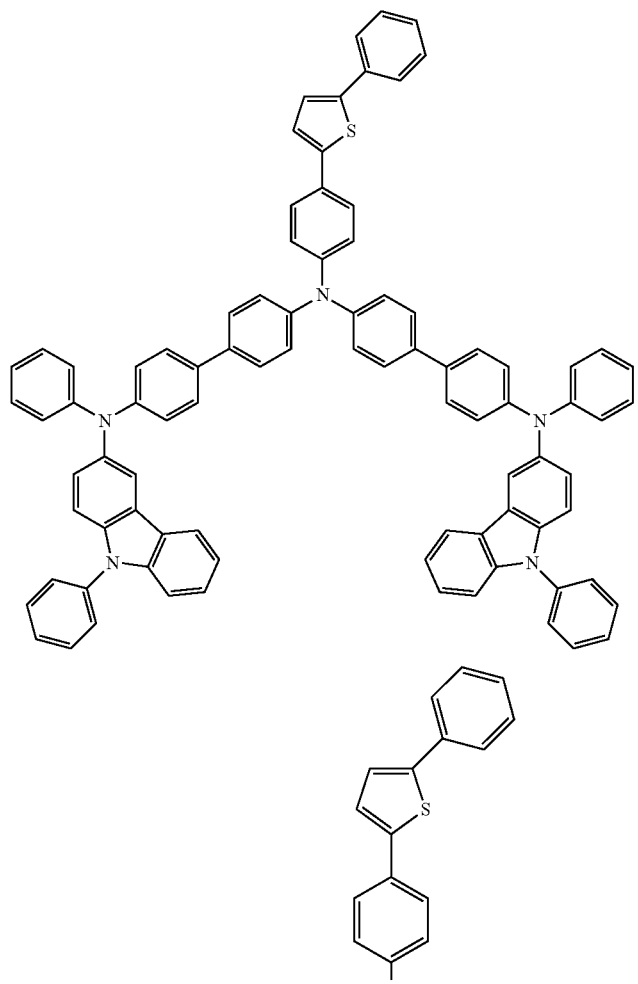

-continued
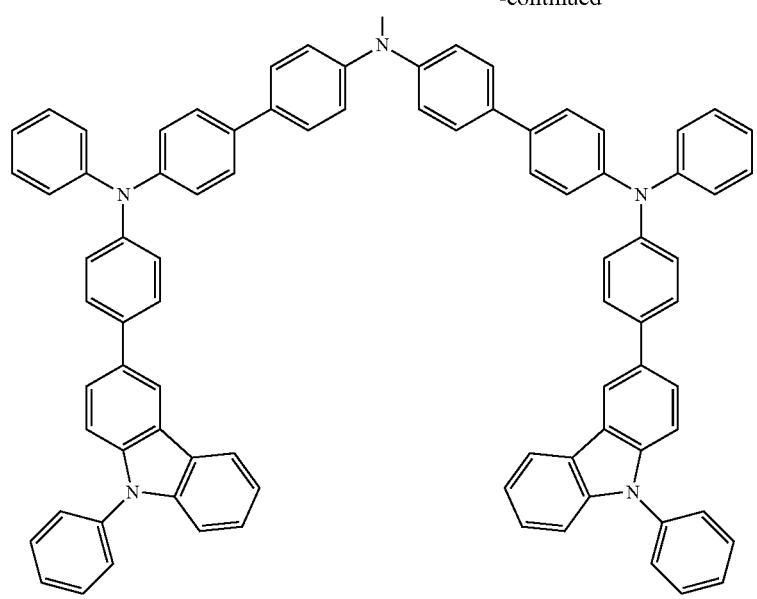
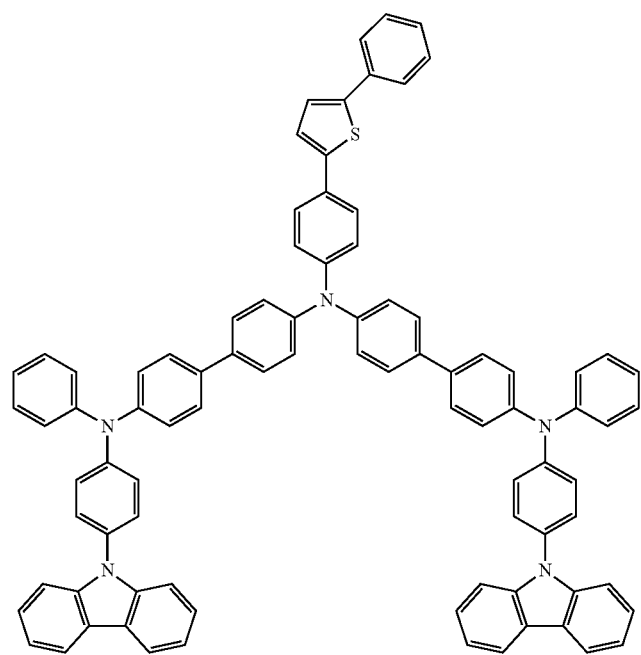

-continued
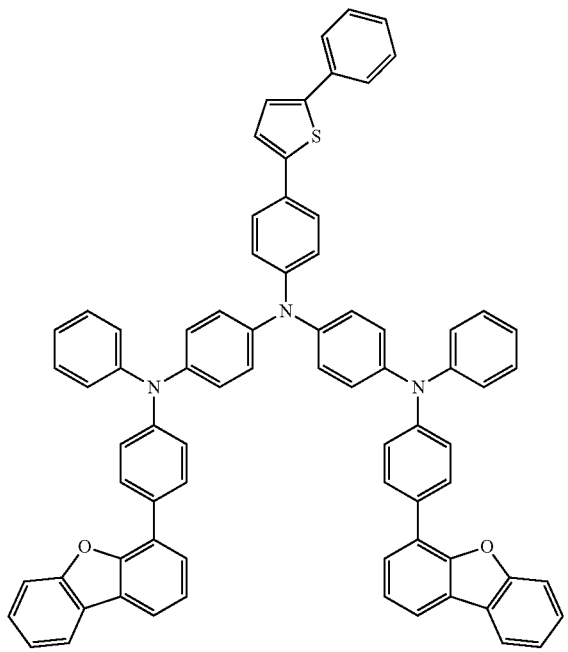
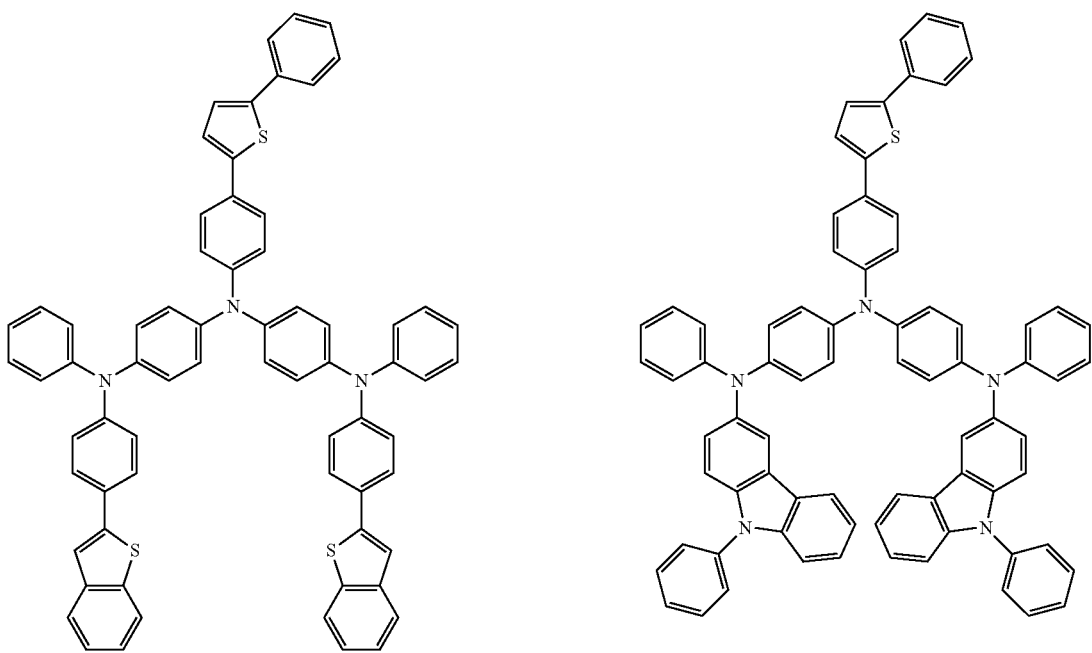

-continued
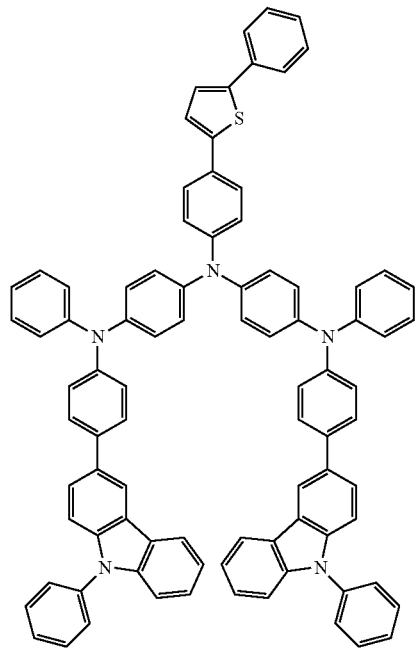 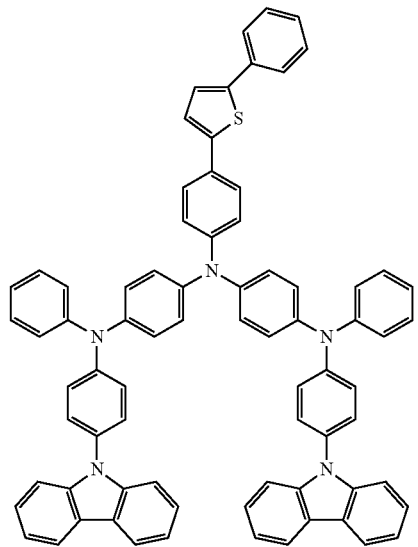
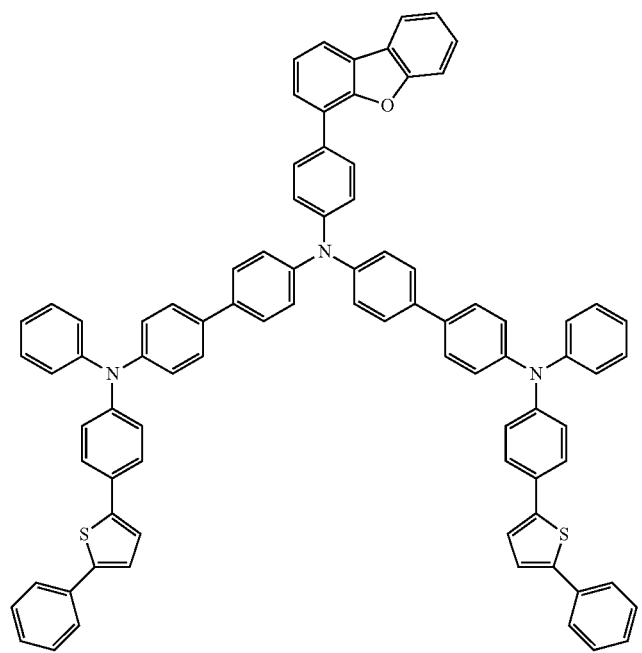

-continued
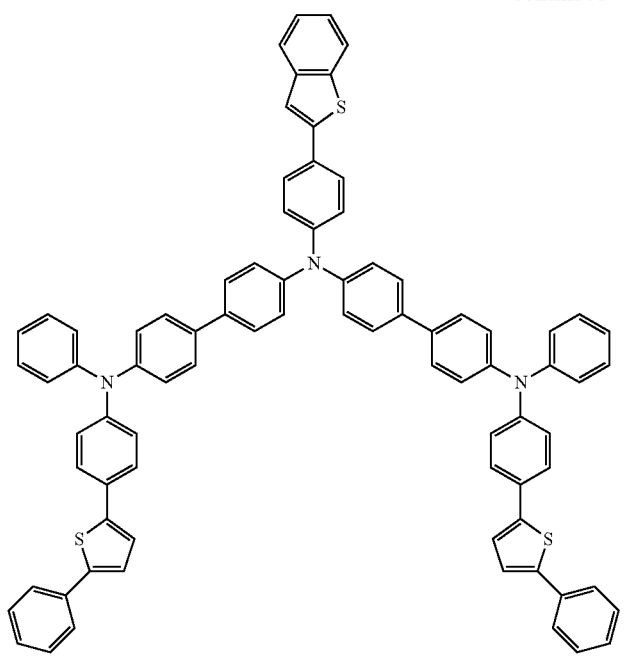
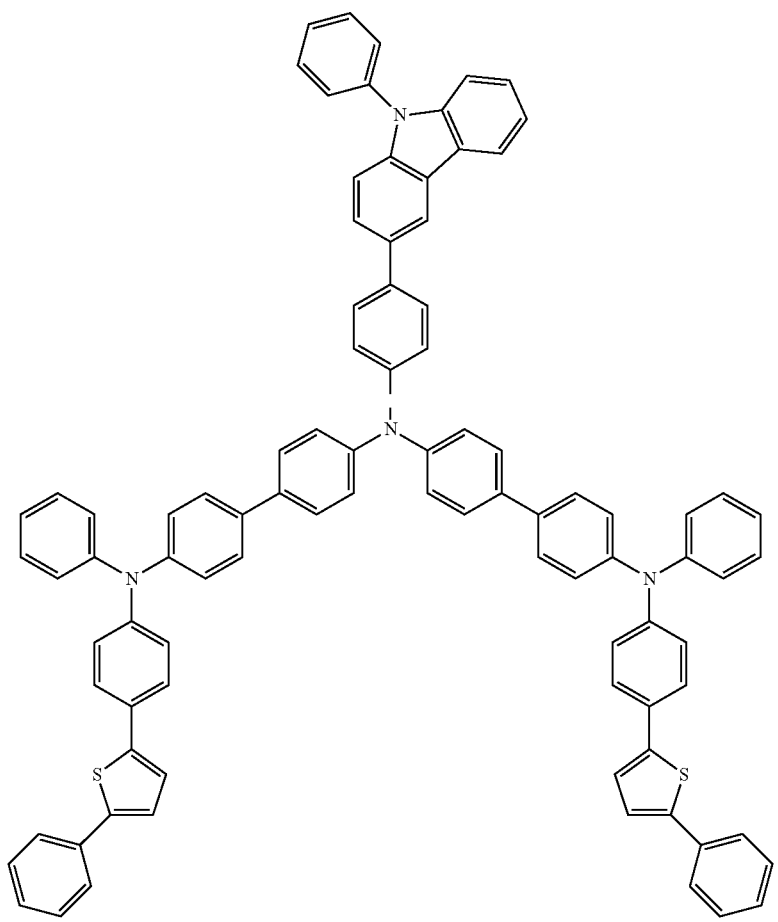

-continued
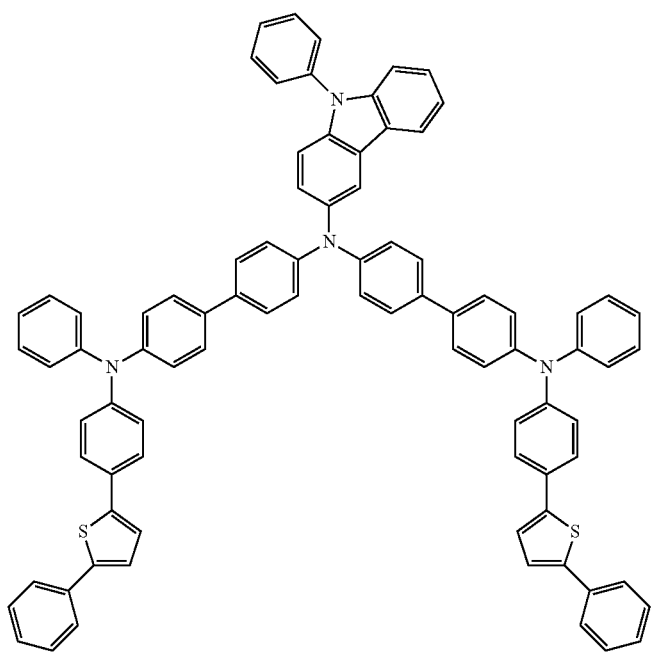
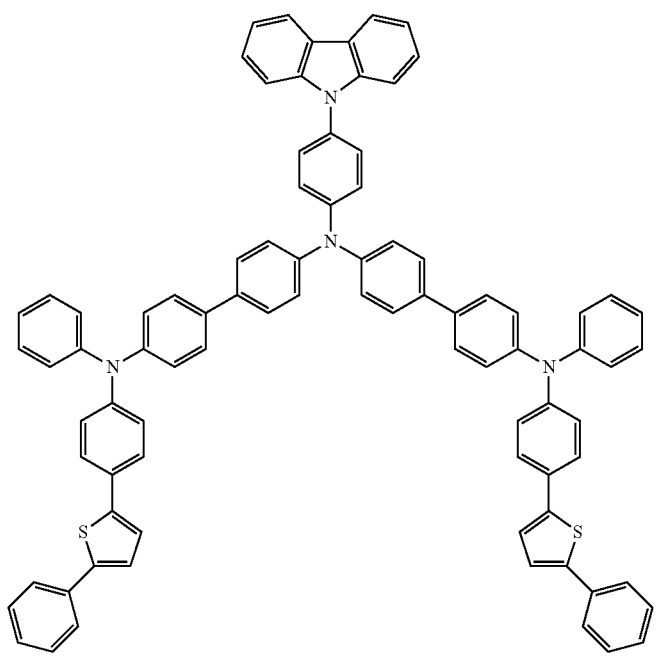

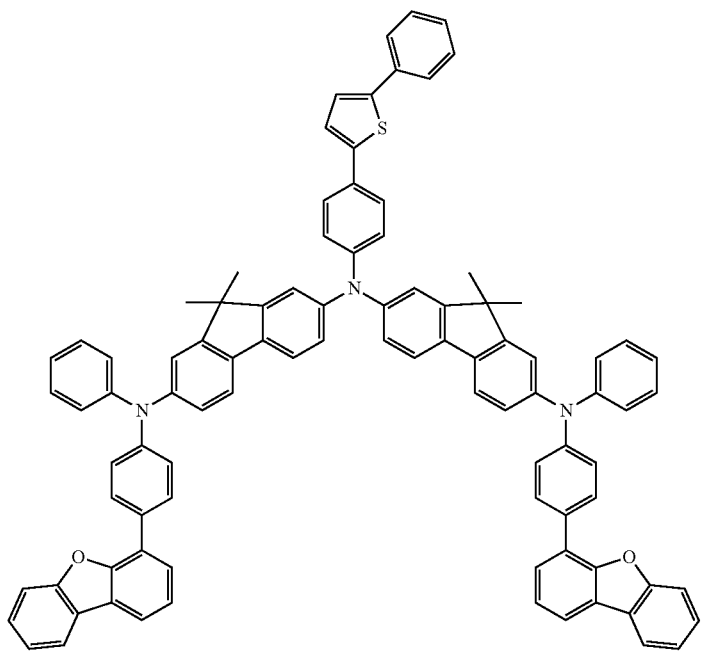
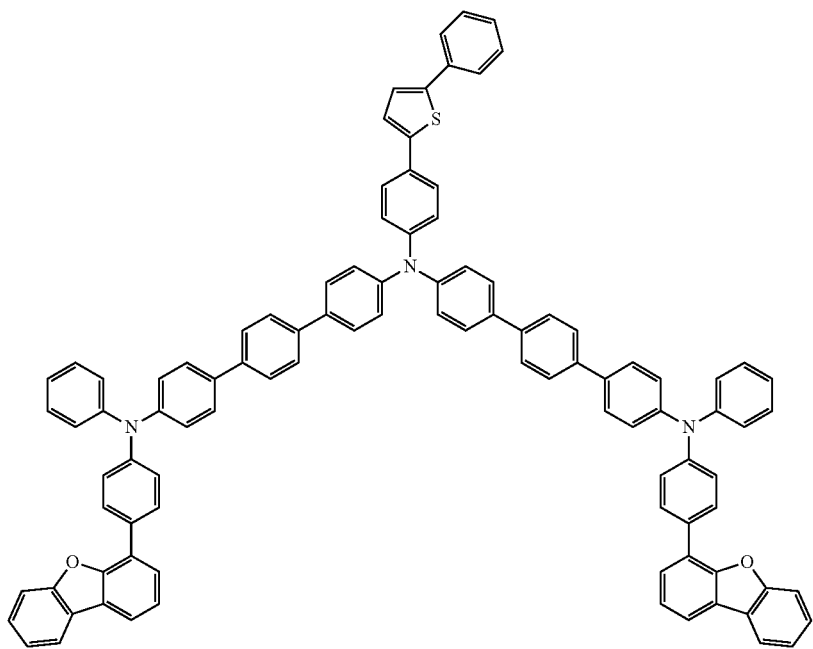

-continued
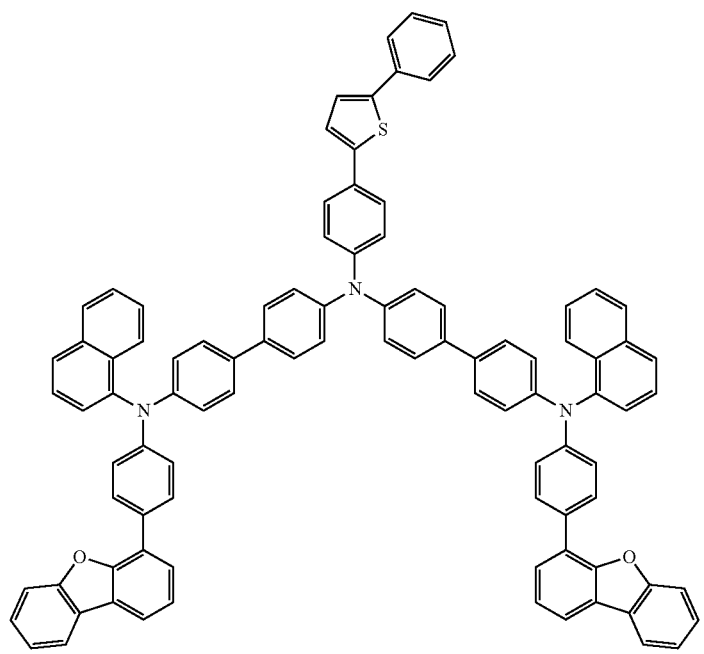
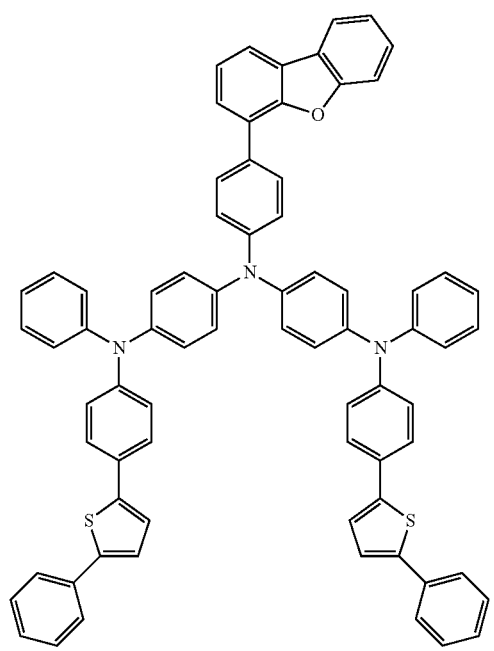

-continued
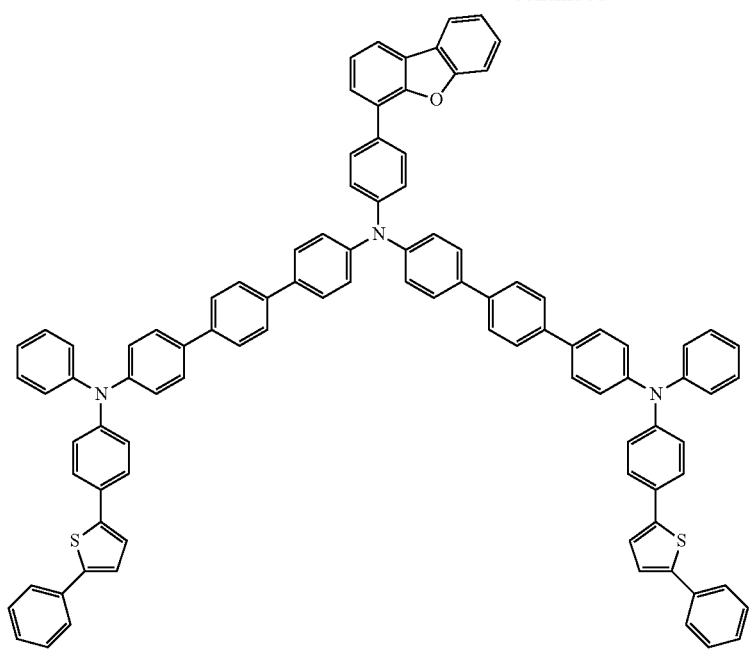
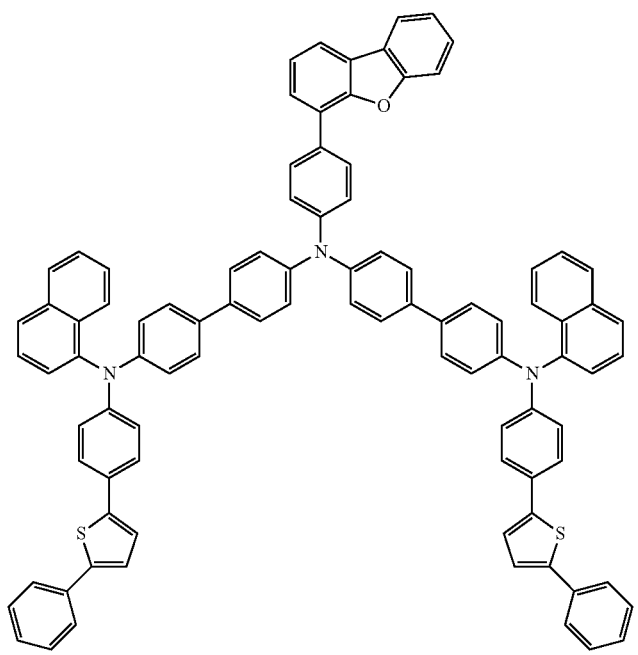

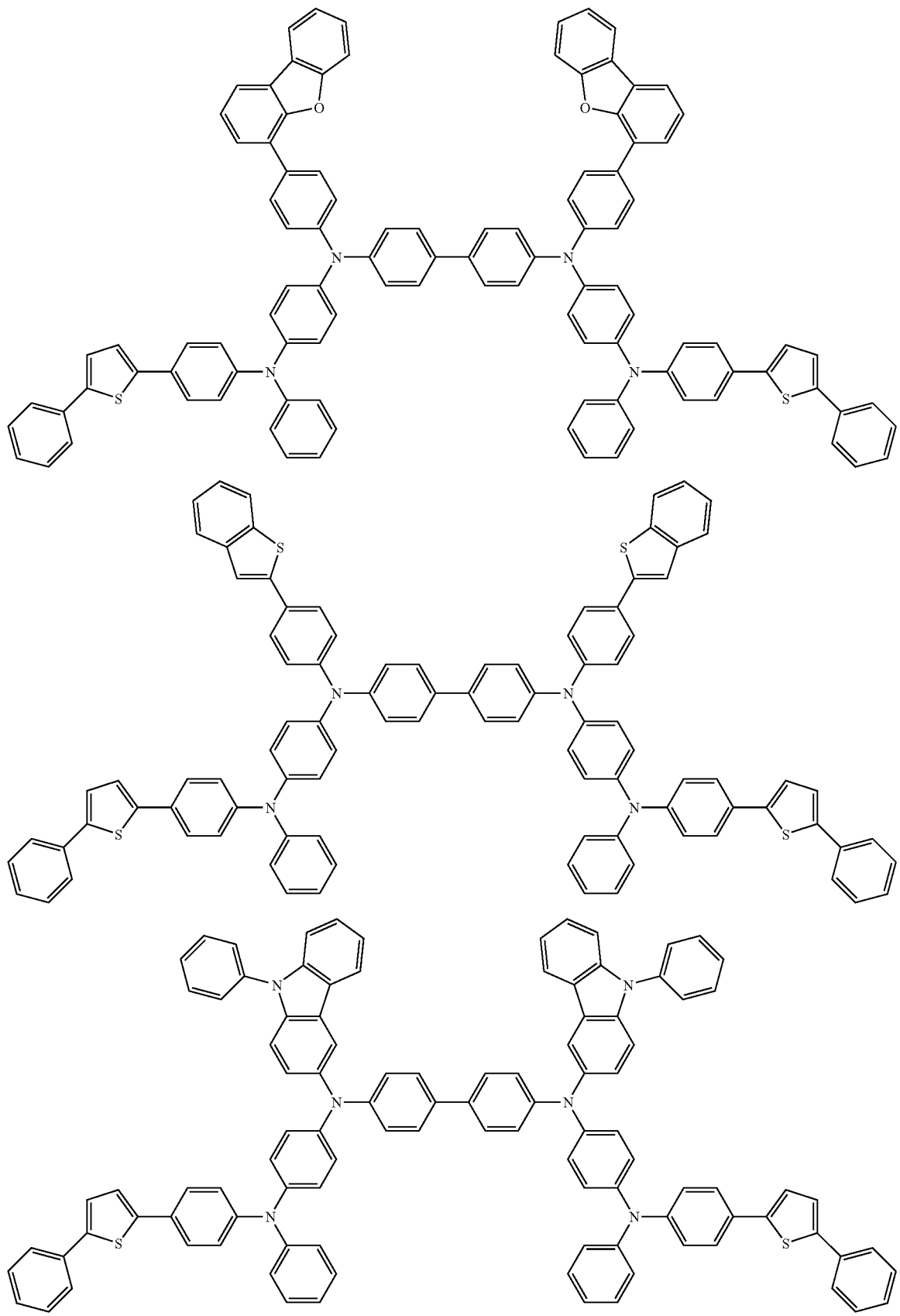

-continued
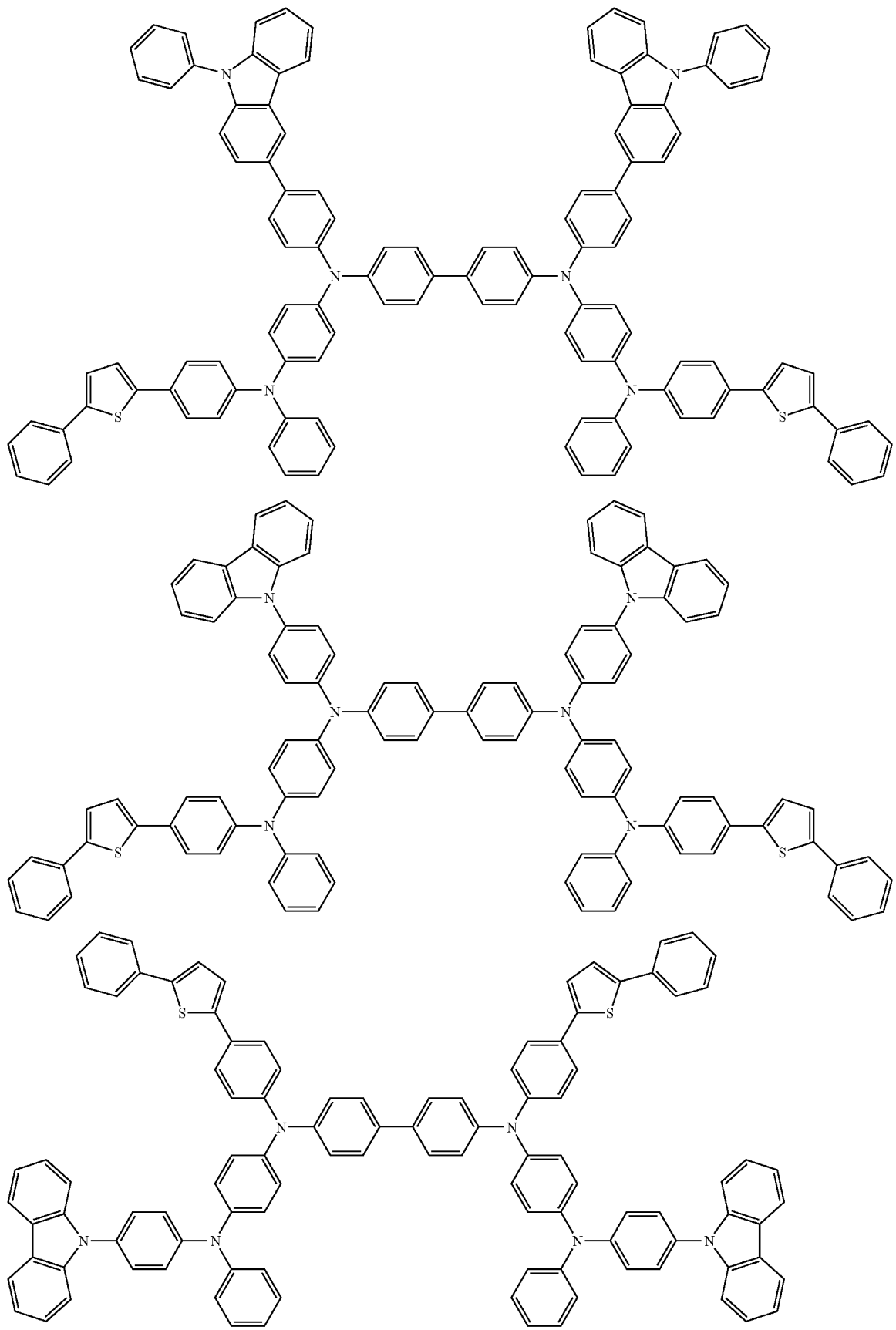

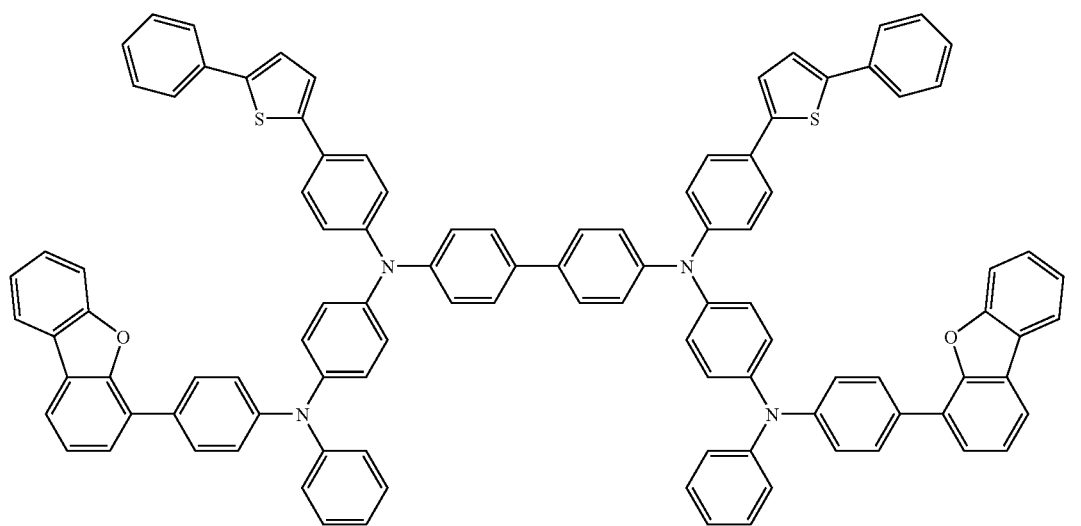
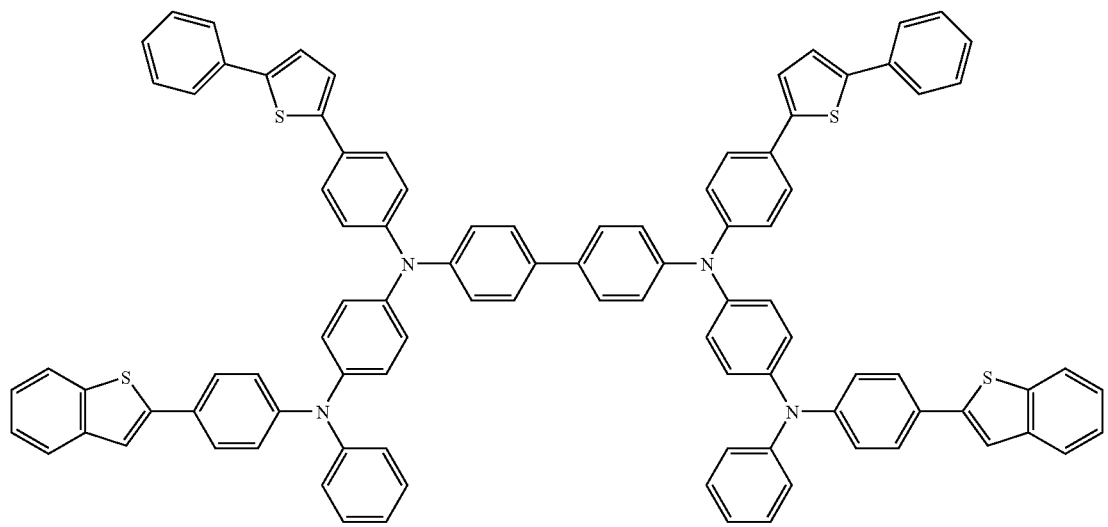
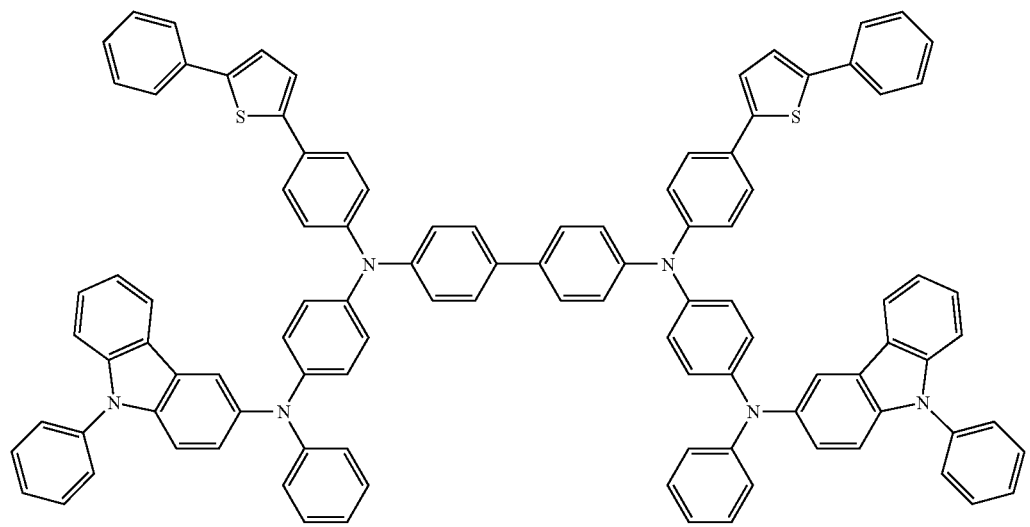

75 76
-continued
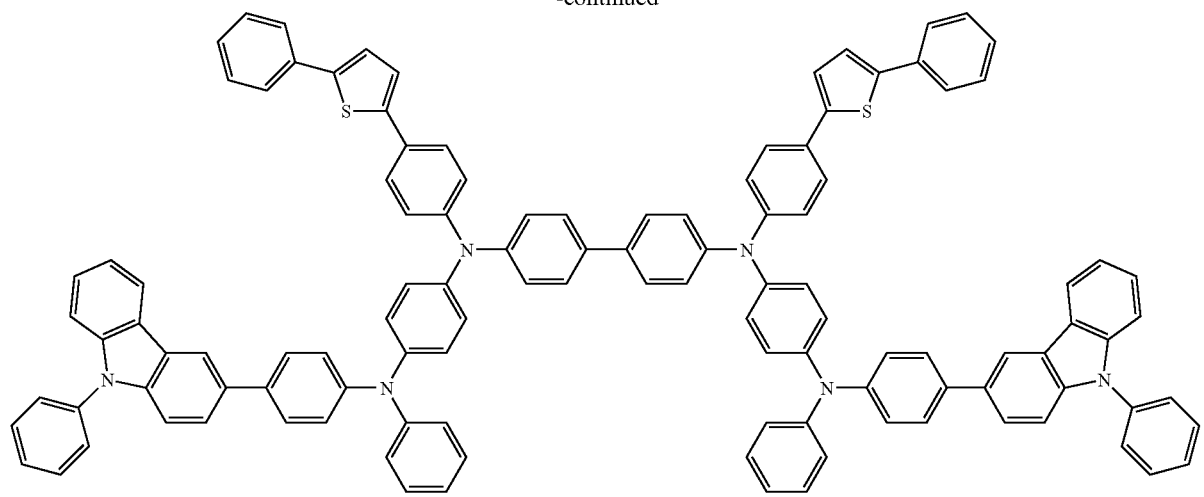
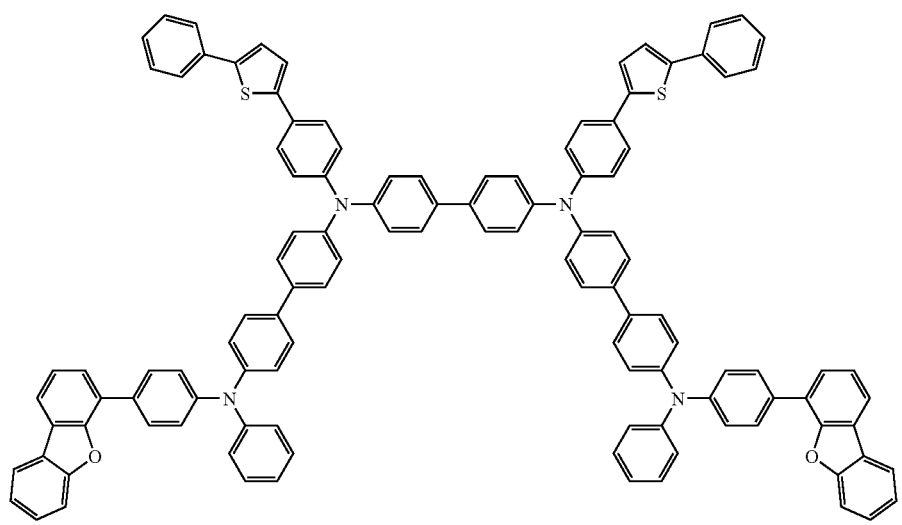
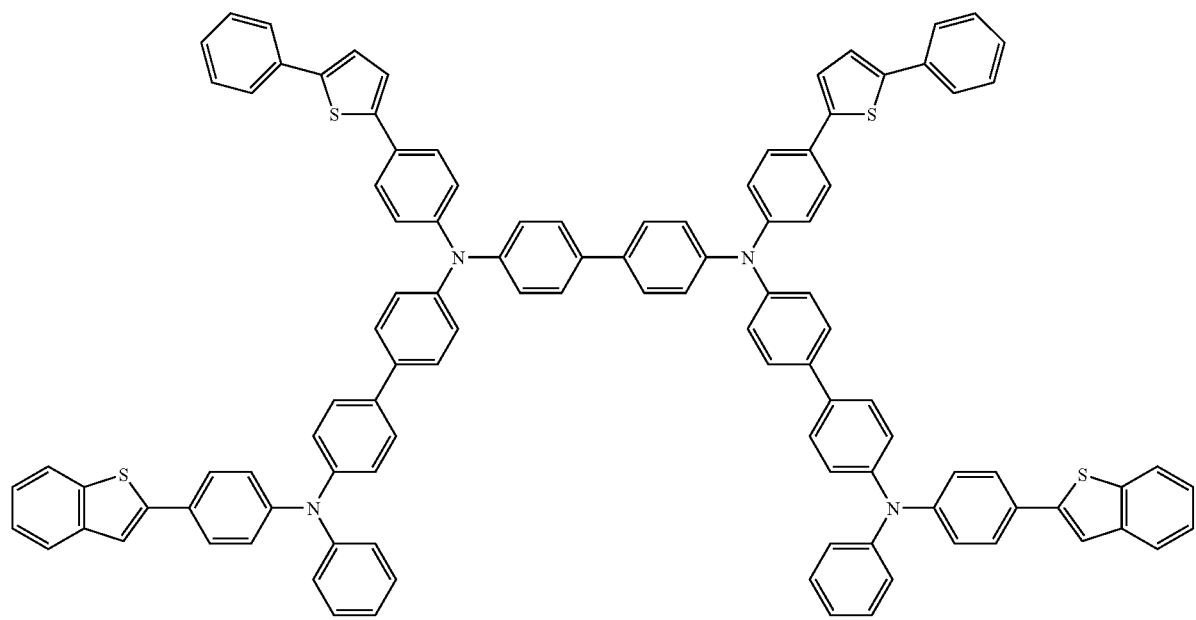

-continued
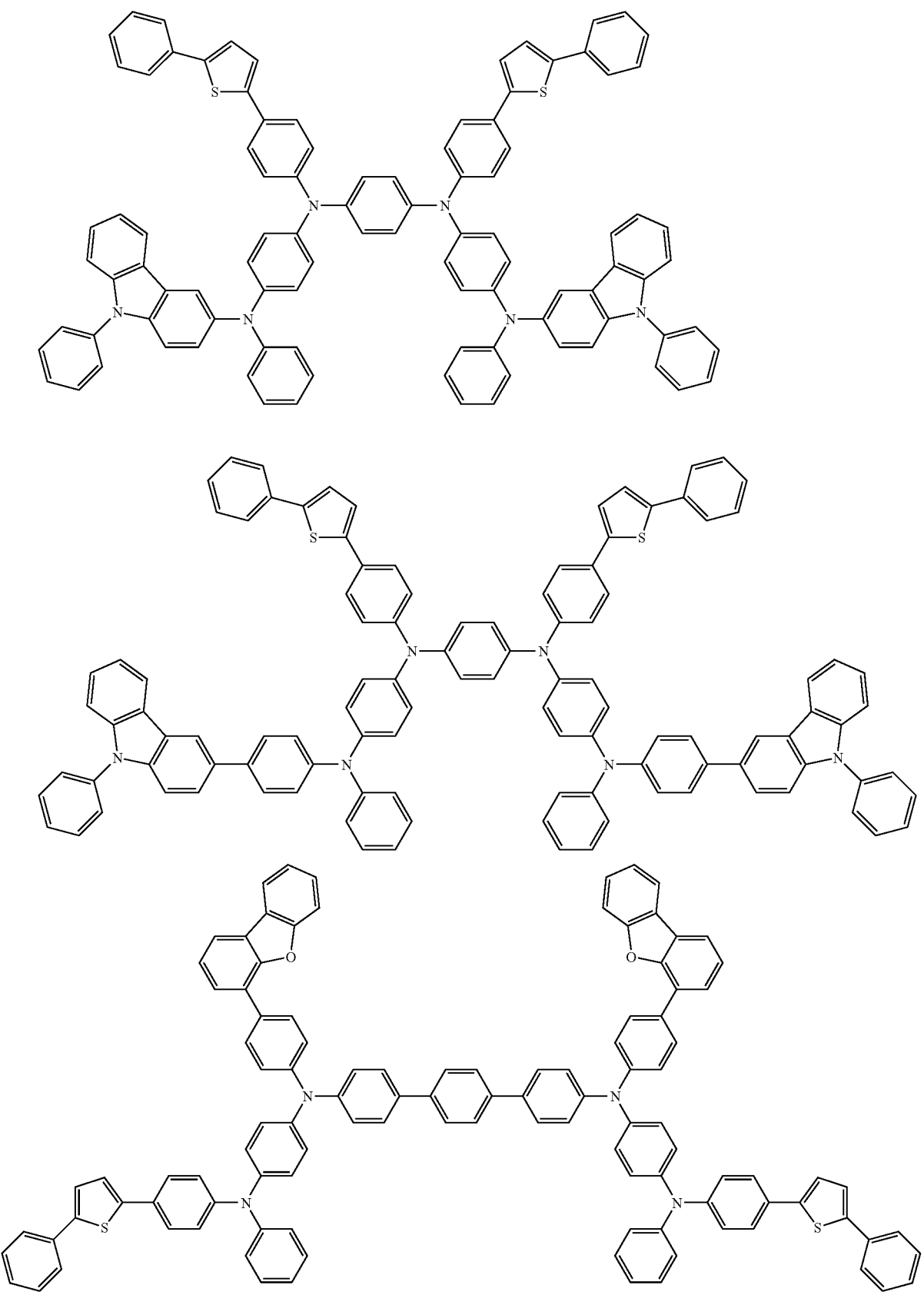

-continued
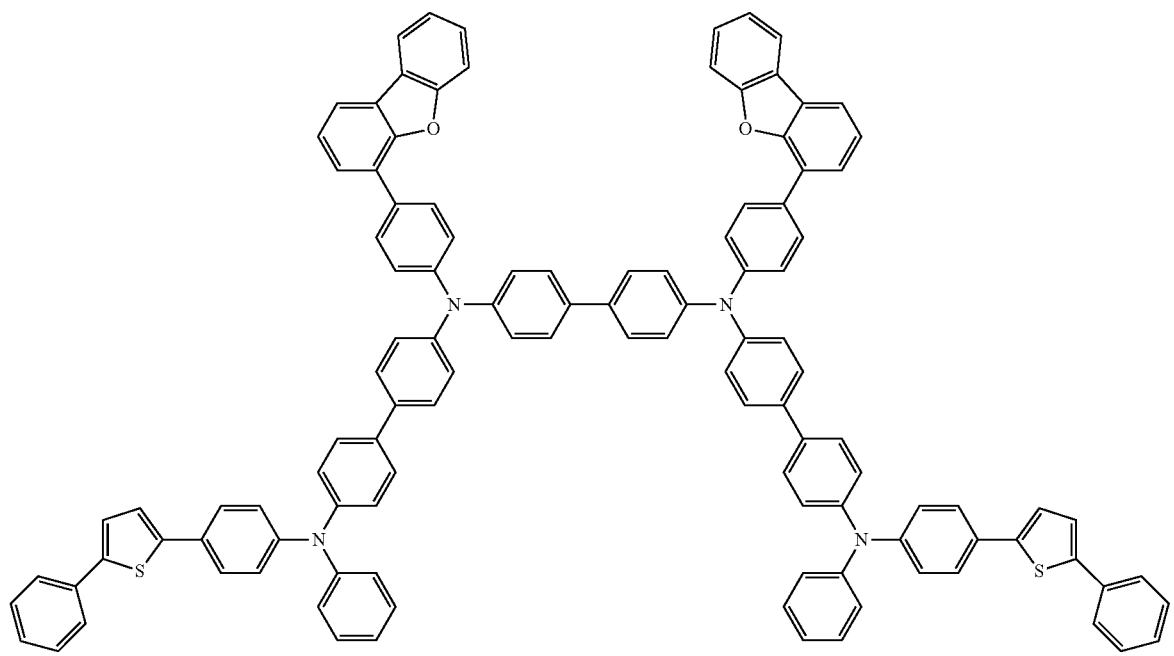
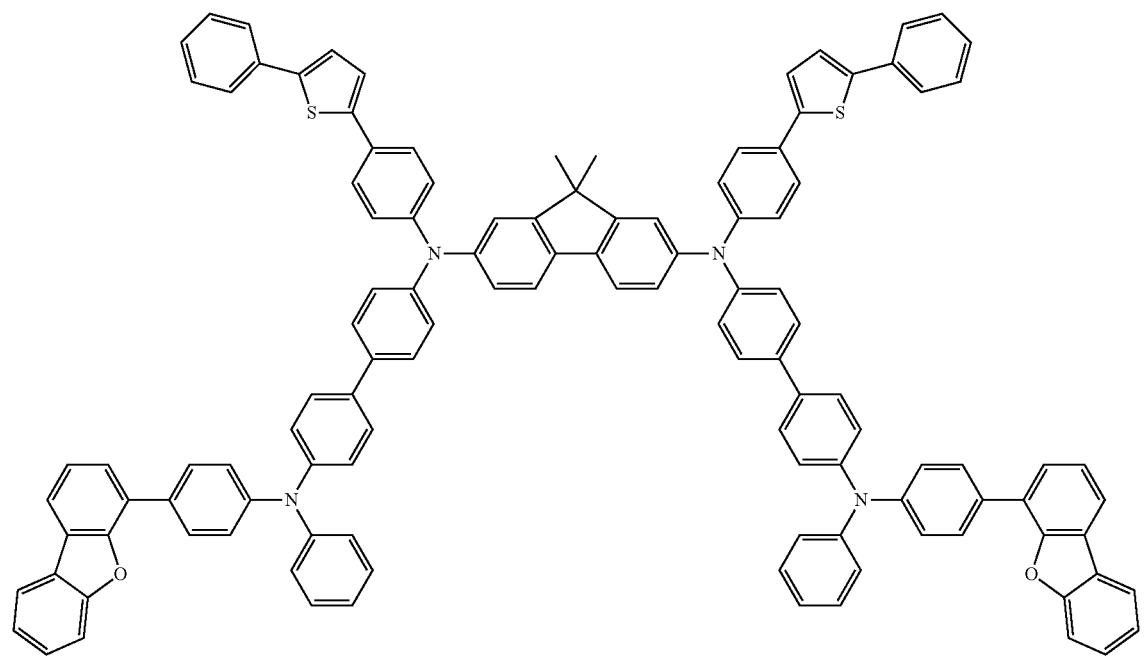

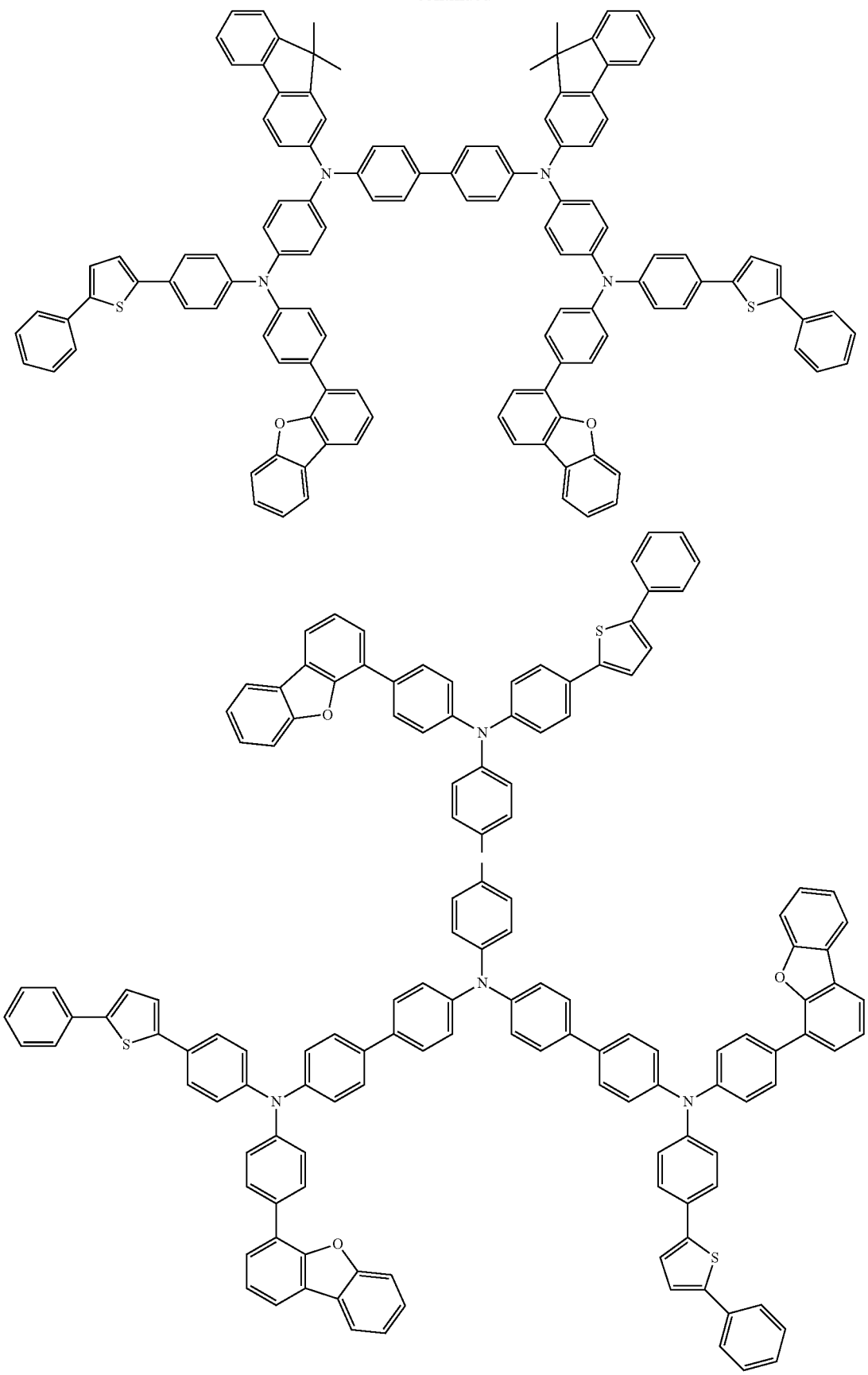

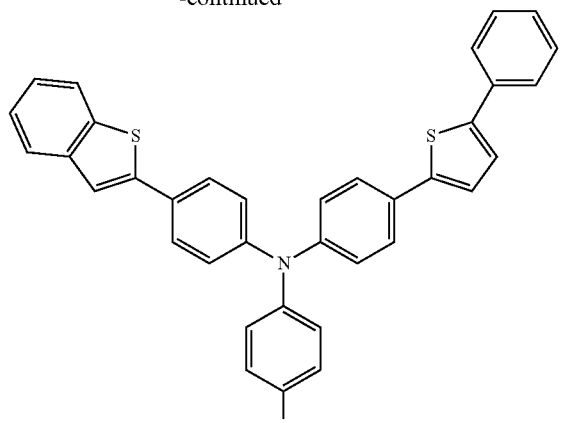
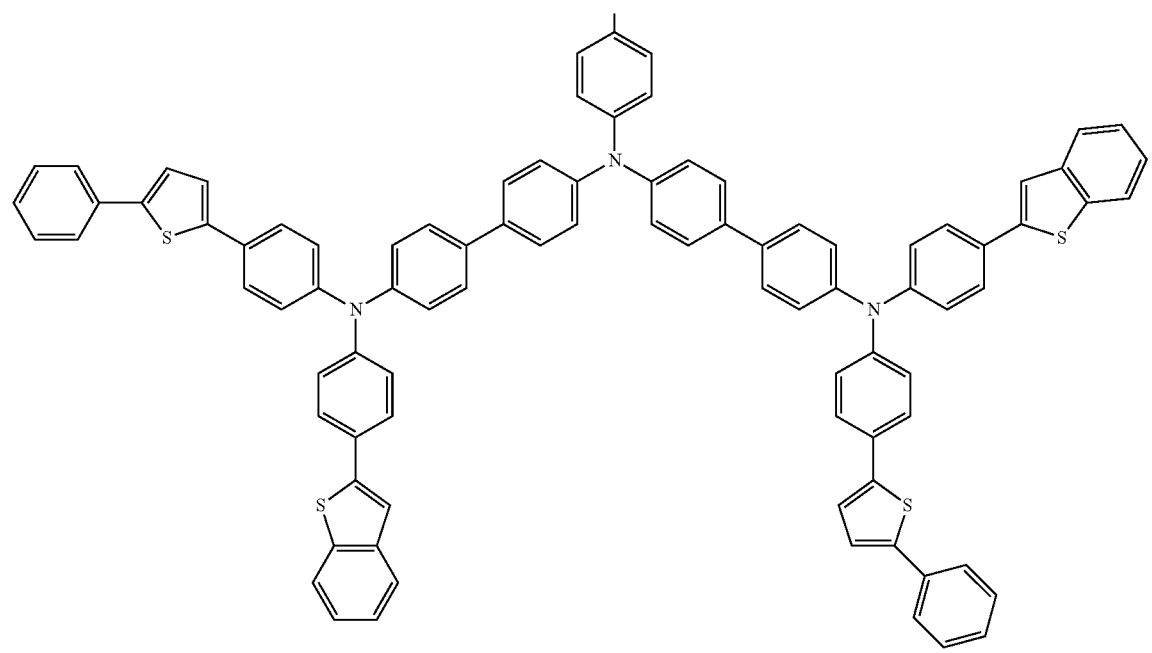
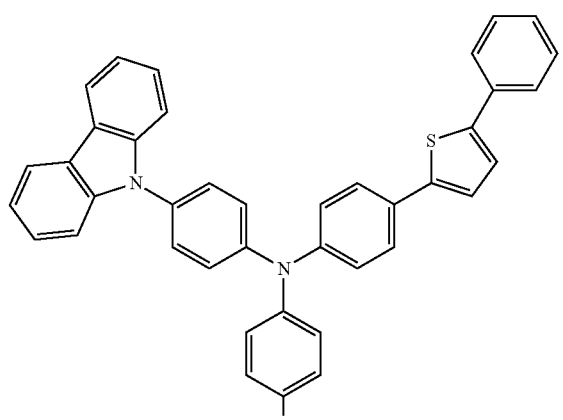

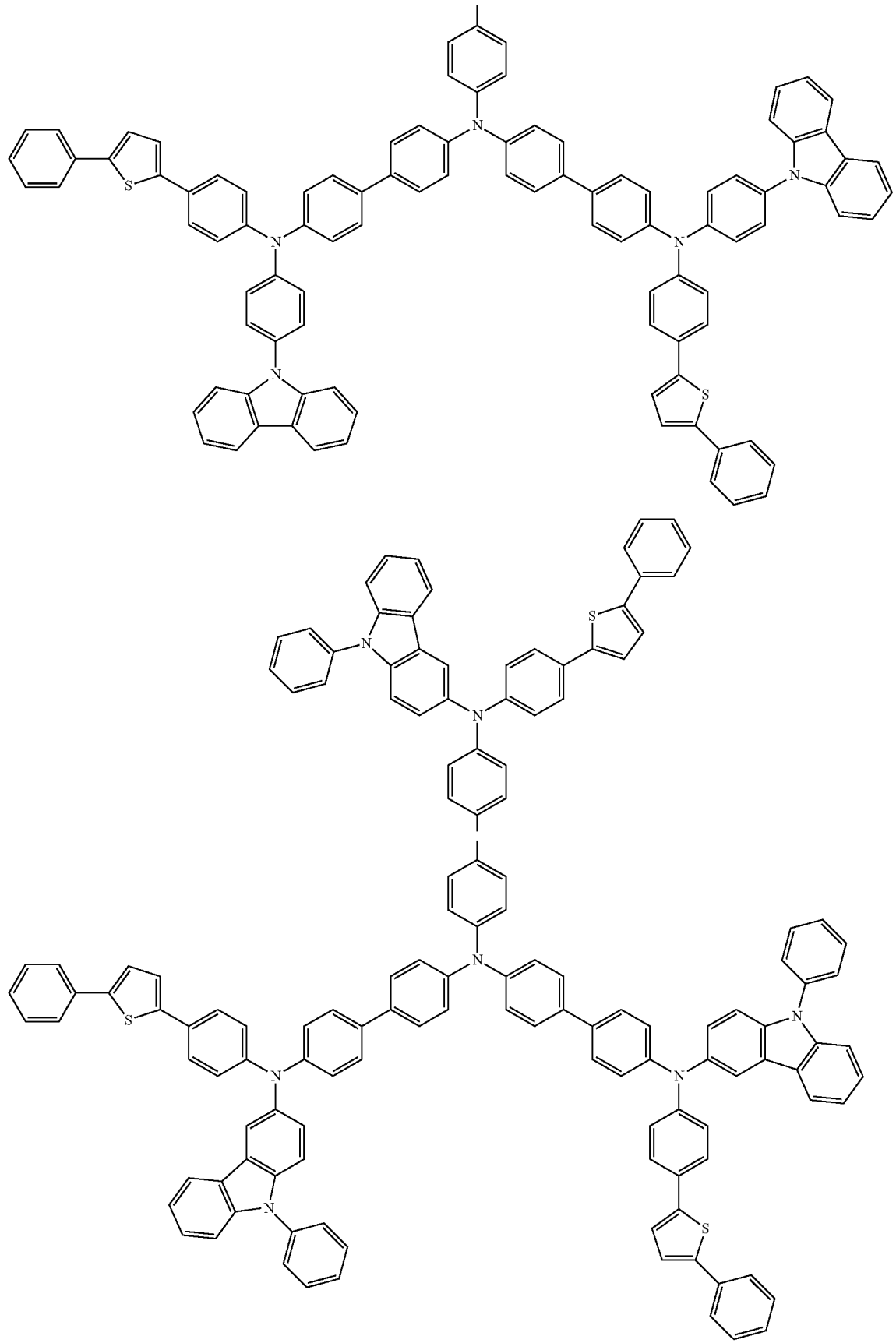

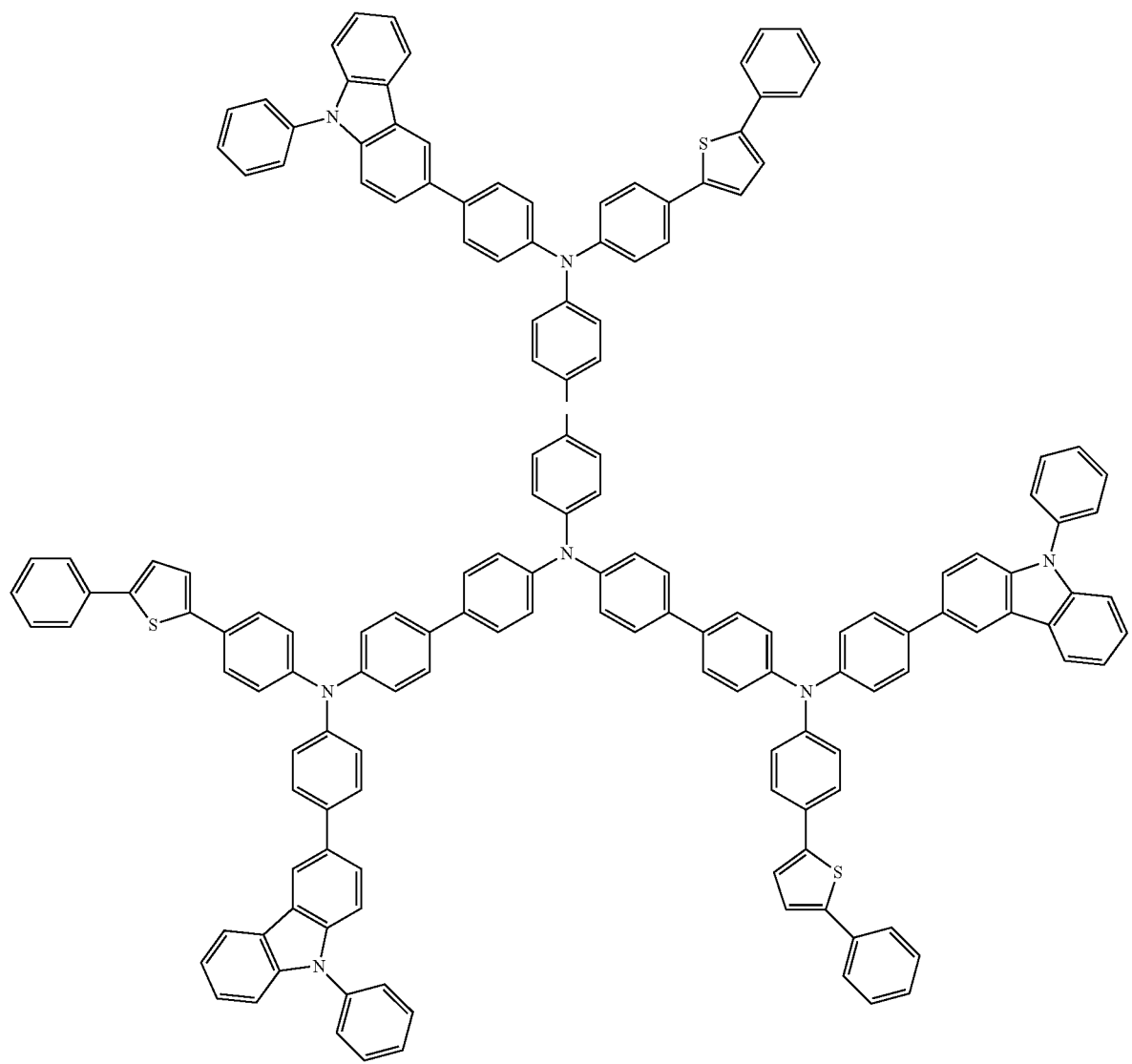
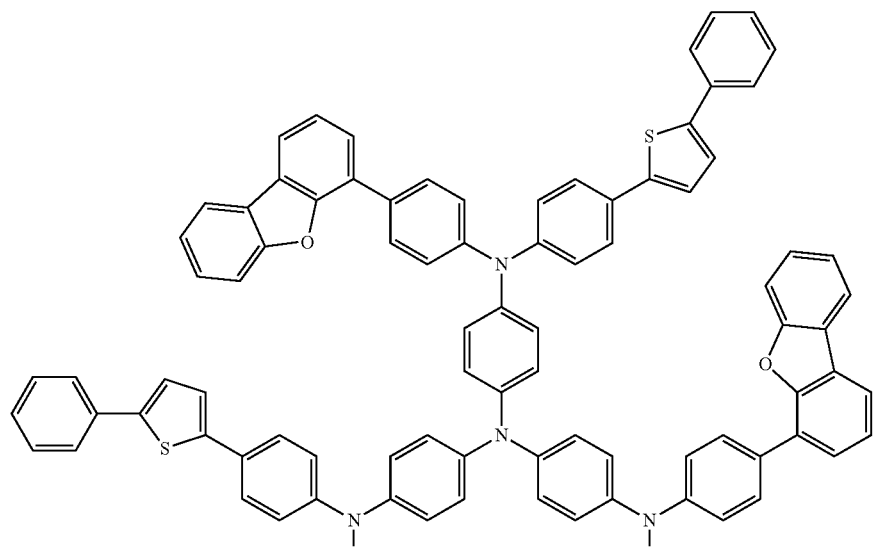

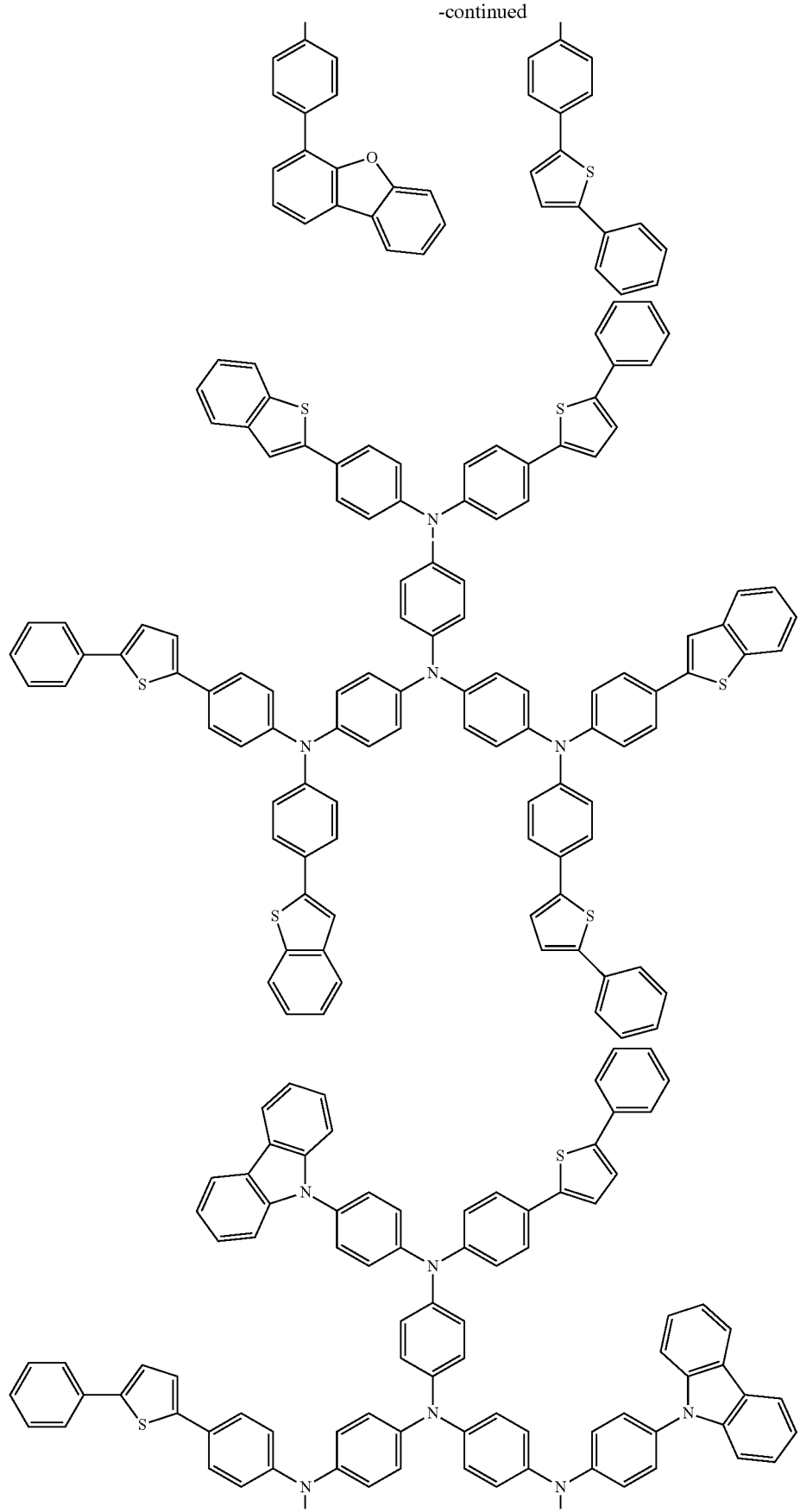

-continued
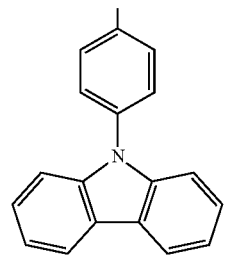
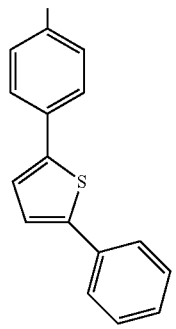
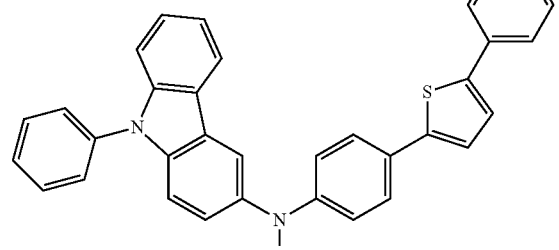
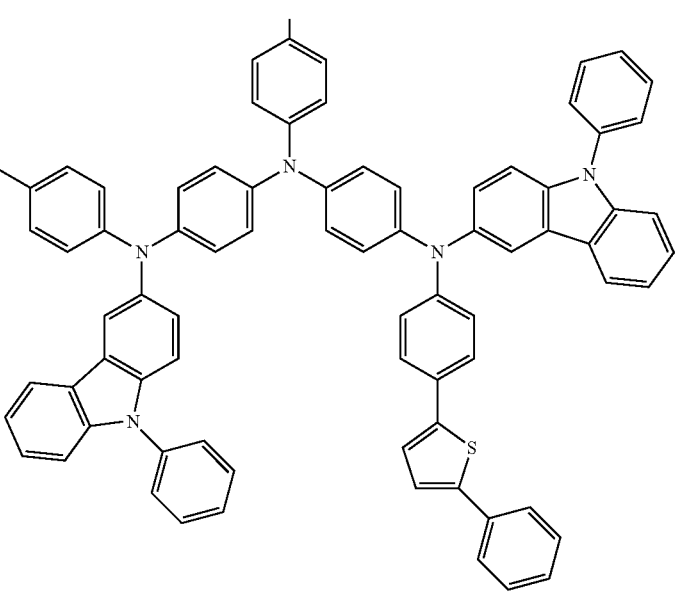

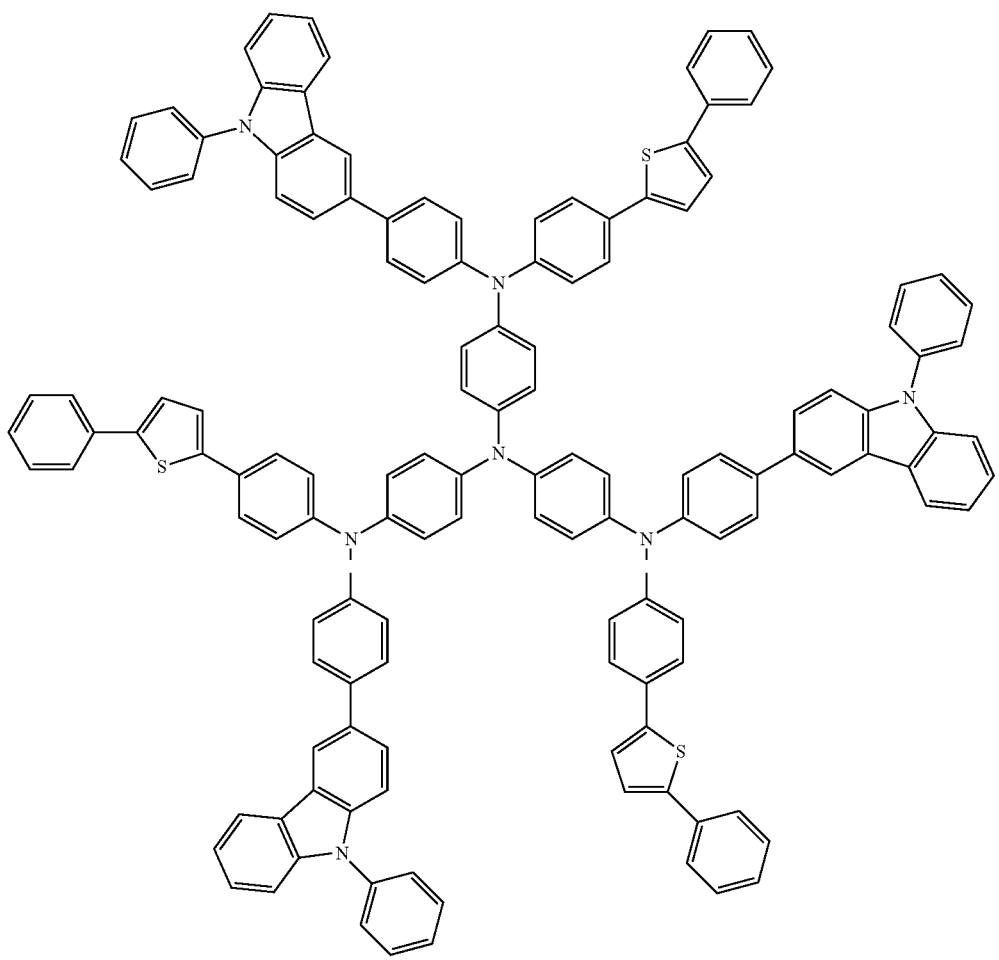
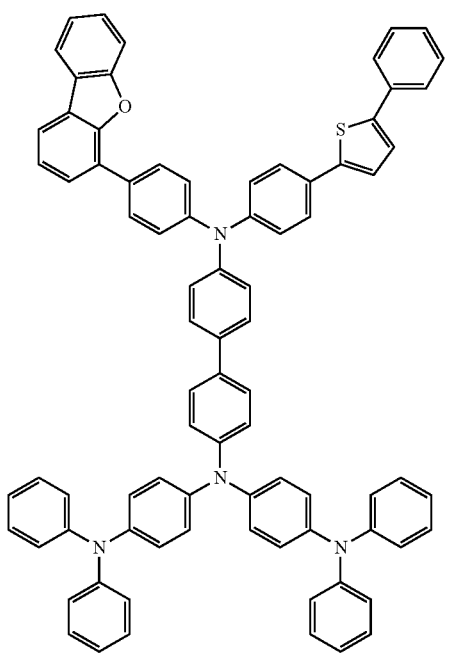

-continued

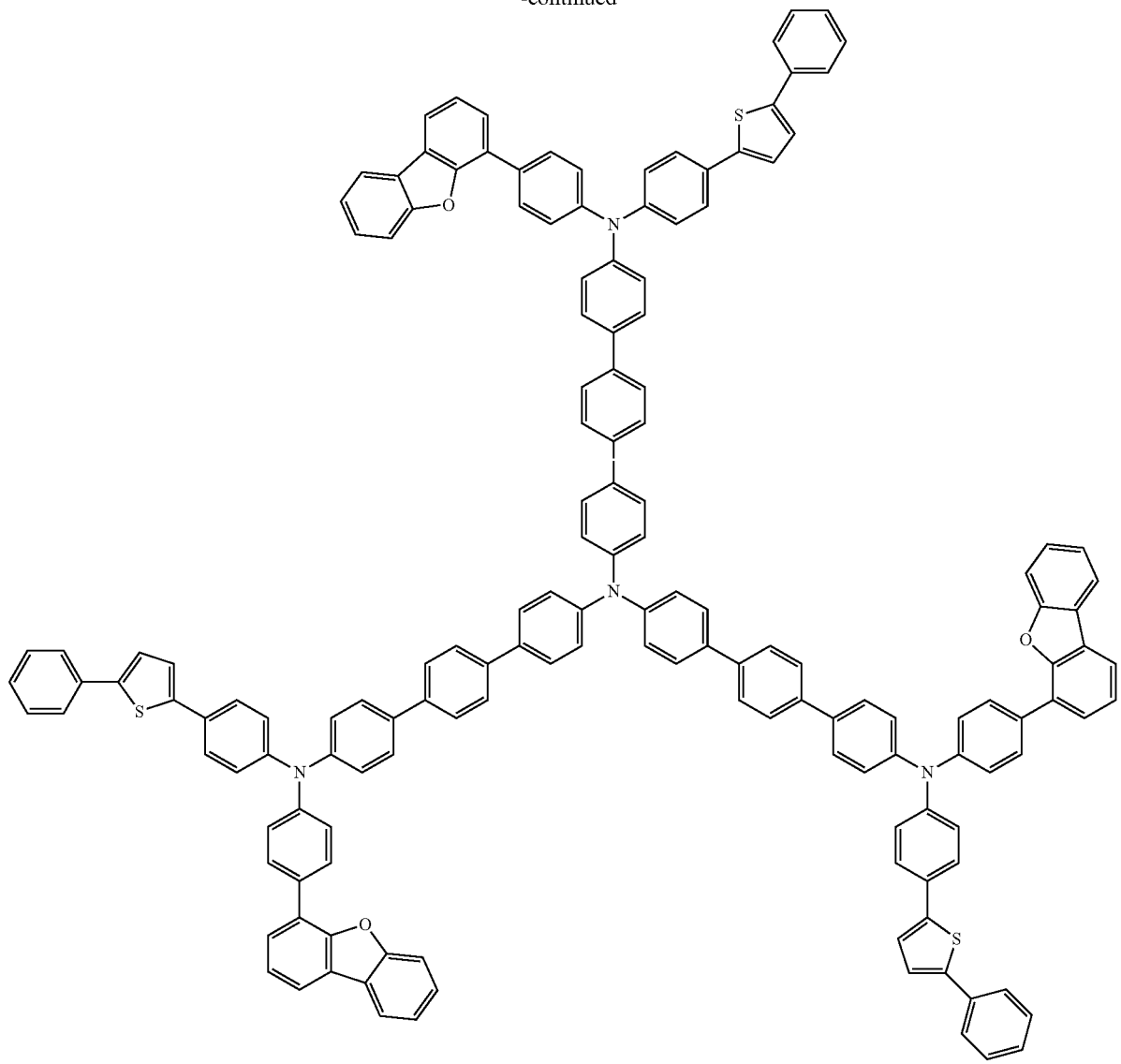

The aromatic amine derivative of the present invention preferably includes a material for an organic electroluminescent device.

The aromatic amine derivative of the present invention preferably includes a hole transporting material for an organic electroluminescent device.

The organic EL device of the present invention includes an organic thin film layer interposed between a cathode and an anode and formed of one layer or a plurality of layers including at least a light emitting layer, in which at least one layer of the organic thin film layer contains the aromatic amine derivative alone or as a component of a mixture.

In the organic EL device of the present invention, it is preferred that the organic thin film layer include a hole transporting layer and/or a hole injecting layer, and the aromatic amine derivative of the present invention be contained in the hole transporting layer and/or the hole injecting layer.

Further, it is preferred that the organic thin film layer include a hole transporting zone including at least a hole transporting layer and a hole injecting layer, and the aromatic amine derivative of the present invention be contained in a layer which is in the hole transporting zone and is other than a layer directly attached to a light emitting layer.

Further, it is preferred that the aromatic amine derivative be contained in a hole transporting layer and/or a hole injecting layer as a main component.

Further, the organic electroluminescent device of the present invention preferably includes a fluorescent dopant. The fluorescent dopant is preferably a compound selected from, for example, an amine-based compound, an aromatic compound, a chelate complex such as a tris(8-quinolinolato) aluminum complex, a coumarin derivative, a tetraphenylbutadiene derivative, a bisstyrylarylene derivative, and an oxadiazole derivative in accordance with a requested luminescent color. An arylamine compound and an aryldiamine compound are particularly preferable examples of such compound; out of those compounds, a styrylamine compound, a styryldiamine compound, an aromatic amine compound, or an aromatic amine compound is more preferable, and a fused polycyclic aromatic compound (excluding amine compounds) is still more preferable. One kind of those fluorescent dopants may be used alone, or two or more kinds thereof may be used in combination.

Compounds each represented by the following general formula (A) are preferable as such styrylamine compound and styryldiamine compound as described above:

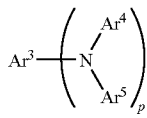
(A)

where: $Ar^3$ represents a group selected from a phenyl group, a naphthyl group, a biphenyl group, a terphenyl group, a stilbene group, and a distyrylaryl group, $Ar^4$ and $Ar^5$ each represent an aromatic hydrocarbon group having 6 to 20 carbon atoms, and each of $Ar^3$, $Ar^4$, and $Ar^5$ may be substituted; p represents an integer of 1 to 4, or preferably 1 or 2; one of $Ar^3$ to $Ar^5$ represents a group containing a styryl group; and at least one of $Ar^4$ and $Ar^5$ is more preferably substituted by a styryl group.

Here, examples of the aromatic hydrocarbon group having 6 to 20 carbon atoms include a phenyl group, a naphthyl group, an anthranyl group, a phenanthryl group, and a terphenyl group.

Compounds each represented by the following general formula (B) are preferable as the aromatic amine compound and the aromatic diamine compound:

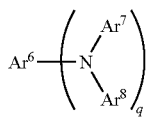
(B)

where: $Ar^6$ to $Ar^8$ each represent a substituted or unsubstituted aryl group having 5 to 40 ring carbon atoms; and q represents an integer of 1 to 4, or preferably 1 or 2.

Here, examples of the aryl group having 5 to 40 ring carbon atoms include a phenyl group, a naphthyl group, an anthranyl group, a phenanthryl group, a pyrenyl group, a coronyl group, a biphenyl group, a terphenyl group, a pyrrolyl group, a furanyl group, a thiophenyl group, a benzothiophenyl group, an oxadiazolyl group, a diphenylanthranyl group, an indolyl group, a carbazolyl group, a pyridyl group, a benzoquinolyl group, a fluoranthenyl group, an acenaphtho fluoranthenyl group, a stilbene group, a perylenyl group, a chrysenyl group, a picenyl group, a triphenylenyl group, a rubicenyl group, a benzoanthracenyl group, a phenylanthracenyl group, a bis anthracenyl group, and aryl groups represented by the following general formulae (C) and (D). Preferred are a naphthyl group, an anthranyl group, a chrysenyl group, a pyrenyl group, and aryl groups represented by the general formula (D):

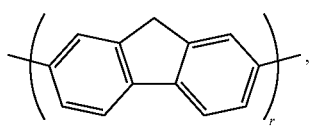
(C)

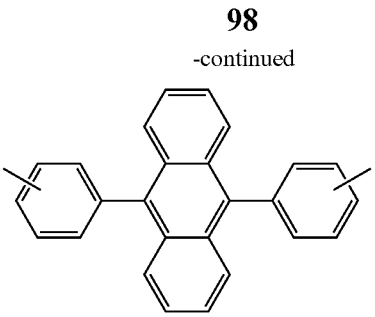
(D)

where r represents an integer of 1 to 3.

Note that examples of preferred substituent which is substituted with substances on the aryl group include alkyl groups each having 1 to 6 carbon atoms (such as an ethyl group, a methyl group, an i-propyl group, an n-propyl group, an s-butyl group, a t-butyl group, a pentyl group, a hexyl group, a cyclopentyl group, and a cyclohexyl group), alkoxy groups having 1 to 6 carbon atoms (such as an ethoxy group, a methoxy group, an i-propoxy group, an n-propoxy group, an s-butoxy group, a t-butoxy group, a pentoxy group, a hexyloxy group, a cyclopentoxy group, and a cyclohexyloxy group), aryl groups having 5 to 40 ring carbon atoms, amino groups substituted by aryl groups having 5 to 40 ring carbon atoms, and ester groups containing an aryl group having 5 to 40 ring carbon atoms, ester groups containing an alkyl group having 1 to 6 carbon atoms, a cyano group, a nitro group, and halogen atoms.

Examples of the fused polycyclic aromatic compound (excluding amine compounds) include fused polycyclic aromatic compounds such as naphthalene, anthracene, phenanthrene, pyrene, coronene, biphenyl, terphenyl, pyrrole, furan, thiophene, benzothiophene, oxadiazole, indole, carbazole, pyridine, benzoquinoline, fluoranthenine, benzofluoranthene, acenaphtho fluoranthenine, stilbene, perylene, chrysene, picene, triphenylenine, rubicene, and benzoanthracene, and derivatives thereof.

In the organic EL device of the present invention, it is preferred that a layer which is one of respective layers constituting the hole injecting layer and/or the hole transporting layer and is in contact with an anode is a layer containing an acceptor material.

The acceptor material is an easily reducing organic compound.

The ease of reduction of the compound can be measured by a reduction potential. In the present invention, in the reduction potential using a saturated calomel electrode (SCE) as a reference electrode, the compound of −0.8 V or more is preferable, and the compound having a larger value than that of the reduction potential of tetracyanoquinodimethane (TCNQ) (about 0 V) is particularly preferable.

As the easily reducing organic compound, an organic compound having an electron-withdrawing substituent is preferably given. Specific examples thereof include quinoid derivatives, pyrazine derivatives, arylborane derivatives, and imide derivatives. The quinoid derivatives include quinodimethane derivatives, thiopyrandioxide derivatives, thioxanthenedioxide derivatives, quinone derivatives, and the like.

The aromatic amine derivative of the present invention is preferably used in an organic EL device which emits blue-based light in particular.

Hereinafter, the structure of the organic EL device of the present invention is described.

(1) Organic EL Device Structure

Typical examples of the structure of the organic EL device of the present invention include the following:

(1) an anode/light emitting layer/cathode;
(2) an anode/hole injecting layer/light emitting layer/cathode;
(3) an anode/light emitting layer/electron injecting layer/cathode;
(4) an anode/hole injecting layer/light emitting layer/electron injecting layer/cathode;
(5) an anode/organic semiconductor layer/light emitting layer/cathode;
(6) an anode/organic semiconductor layer/electron blocking layer/light emitting layer/cathode;
(7) an anode/organic semiconductor layer/light emitting layer/adhesion improving layer/cathode;
(8) an anode/hole injecting layer/hole transporting layer/light emitting layer/electron injecting layer/cathode;
(9) an anode/acceptor-containing layer/hole injecting layer/hole transporting layer/light emitting layer/electron transporting layer/electron injecting layer/cathode;
(10) an anode/insulating layer/light emitting layer/insulating layer/cathode;
(11) an anode/inorganic semiconductor layer/insulating layer/light emitting layer/insulating layer/cathode;
(12) an anode/organic semiconductor layer/insulating layer/light emitting layer/insulating layer/cathode;
(13) an anode/insulating layer/hole injecting layer/hole transporting layer/light emitting layer/insulating layer/cathode; and
(14) an anode/insulating layer/hole injecting layer/hole transporting layer/light emitting layer/electron injecting layer/cathode.

Of those, the structure (8) is preferably used in ordinary cases. However, the structure is not limited to the foregoing.

The aromatic amine derivative of the present invention may be used in any one of the organic thin film layers of the organic EL device. The derivative can be used in a light emitting zone or a hole transporting zone. The derivative is used preferably in the hole transporting zone, or particularly preferably in a hole injecting layer, thereby making a molecule hardly crystallize and improving yields upon production of the organic EL device.

The amount of the aromatic amine derivative of the present invention to be incorporated into the organic thin film layers is preferably 30 to 100 mol %.

(2) Light-Transmissive Substrate

The organic EL device of the present invention is prepared on a light-transmissive substrate. Here, the light-transmissive substrate is the substrate which supports the organic EL device. It is preferable that the light-transmissive substrate have a transmittance of light of 50% or higher in the visible region of 400 to 700 nm and be flat and smooth.

Examples of the light-transmissive substrate include glass plates and polymer plates. Specific examples of the glass plate include plates formed of soda-lime glass, glass containing barium and strontium, leadglass, aluminosilicate glass, borosilicate glass, barium borosilicate glass, and quartz. Specific examples of the polymer plate include plates formed of polycarbonate, acrylic, polyethylene terephthalate, polyether sulfide, and polysulfone.

(3) Anode

The anode of the organic EL device of the present invention has the function of injecting holes into the hole transporting layer or the light emitting layer. It is effective that the anode has a work function of 4.5 eV or higher. Specific examples of the material for the anode used in the present invention include indium tin oxide (ITO) alloys, tin oxide (NESA), indium zinc oxide (IZO), gold, silver, platinum, and copper.

The anode can be prepared by forming a thin film of the electrode material described above in accordance with a process such as the vapor deposition process and the sputtering process.

When the light emitted from the light emitting layer is obtained through the anode, it is preferable that the anode have a transmittance of higher than 10% with respect to the emitted light. It is also preferable that the sheet resistance of the anode be several hundred Ω per square or smaller. The thickness of the anode is, in general, selected in the range of 10 nm to 1 μm and preferably in the range of 10 to 200 nm although the preferable range may be different depending on the used material.

(4) Light Emitting Layer

The light emitting layer of the organic EL device has a combination of the following functions (1) to (3).

(1) The injecting function: the function of injecting holes from the anode or the hole injecting layer and injecting electrons from the cathode or the electron injecting layer when an electric field is applied.

(2) The transporting function: the function of transporting injected charges (i.e., electrons and holes) by the force of the electric field.

(3) The light emitting function: the function of providing the field for recombination of electrons and holes and leading to the emission of light.

However, the easiness of injection may be different between holes and electrons and the ability of transportation expressed by the mobility may be different between holes and electrons. It is preferable that either one of the charges be transferred.

A known process such as a vapor deposition process, a spin coating process, or an LB method is applicable to the formation of the light emitting layer. The light emitting layer is particularly preferably a molecular deposit film. The term "molecular deposit film" as used herein refers to a thin film formed by the deposition of a material compound in a vapor phase state, or a film formed by the solidification of a material compound in a solution state or a liquid phase state. The molecular deposit film can be typically distinguished from a thin film formed by the LB method (molecular accumulation film) on the basis of differences between the films in aggregation structure and higher order structure, and functional differences between the films caused by the foregoing differences.

In addition, as disclosed in JP-A-57-51781, the light emitting layer can also be formed by: dissolving a binder such as a resin and a material compound in a solvent to prepare a solution; and forming a thin film from the prepared solution by the spin coating method or the like.

In a case where the compound of the present invention is used for a light emitting layer, where desired, the light emitting layer may include other known light emitting materials other than the light emitting material composed of the aromatic amine derivative of the present invention, or a light emitting layer including other known light emitting material may be laminated to the light emitting layer including the light emitting material composed of the aromatic amine derivative of the present invention as long as the object of the present invention is not adversely affected.

A light emitting material to be used in combination with the compound of the present invention is mainly an organic compound, and examples of a doping material which can be used include, but not limited to, anthracene, naphthalene, phenanthrene, pyrene, tetracene, coronene, chrysene, fluoresceine, perylene, phthaloperylene, naphthaloperylene, perynone, phthaloperynone, naphthaloperynone, diphenylbutadiene, tetraphenylbutadiene, coumarin, oxadiazole, aldazine, bisbenzoxazoline, bisstyryl, pyrazine, cyclopentadiene, quinoline metal complexes, aminoquinoline metal complexes, benzoquinoline metal complexes, imine, diphenylethylene, vinylanthracene, diaminocarbazole, pyrane, thiopyrane, polymethine, merocyanine, imidazole-chelated oxynoid compounds, quinacridone, rubrene, and fluorescent dyes.

A host material that can be used together with the compound of the present invention is preferably a compound represented by any one of the following formulae (i) to (xi):

an asymmetric anthracene represented by the following general formula (i):

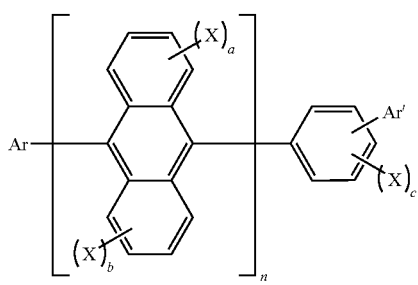

(i)

where: Ar represents a substituted or unsubstituted fused aromatic group having 10 to 50 ring carbon atoms;

Ar' represents a substituted or unsubstituted aromatic group having 6 to 50 ring carbon atoms;

X represents a substituted or unsubstituted aromatic group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a carboxyl group, a halogen atom, a cyano group, a nitro group, or a hydroxyl group;

a, b, and c each represent an integer of 0 to 4; and n represents an integer of 1 to 3, and when n represents 2 or more, anthracene nuclei in [ ] may be identical to or different from each other;

an asymmetric monoanthracene derivative represented by the following general formula (ii):

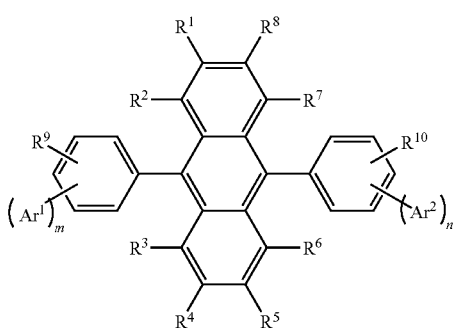

(ii)

where: $Ar^1$ and $Ar^2$ each independently represent a substituted or unsubstituted aromatic ring group having 6 to 50 ring carbon atoms; m and n each represent an integer of 1 to 4, provided that $Ar^1$ and $Ar^2$ are not identical to each other when m=n=1 and positions at which $Ar^1$ and $Ar^2$ are bonded to a benzene ring are bilaterally symmetric, and m and n represent different integers when m or n represents an integer of 2 to 4; and $R^1$ to $R^{10}$ each independently represent a hydrogen atom, a substituted or unsubstituted aromatic ring group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group, or a hydroxyl group;

an asymmetric pyrene derivative represented by the following general formula (iii):

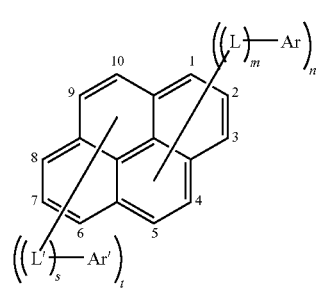

(iii)

where: Ar and Ar' each represent a substituted or unsubstituted aromatic group having 6 to 50 ring carbon atoms;

L and L' each represent a substituted or unsubstituted phenylene group, a substituted or unsubstituted naphthalenylene group, a substituted or unsubstituted fluorenylene group, or a substituted or unsubstituted dibenzosilolylene group;

m represents an integer of 0 to 2; n represents an integer of 1 to 4; s represents an integer of 0 to 2; t represents an integer of 0 to 4; and in addition, L or Ar binds to any one of 1- to 5-positions of pyrene, and L' or Ar' binds to any one of 6- to 10-positions of pyrene, provided that Ar, Ar', L, and L' satisfy the following item (1) or (2) when n+t represents an even number:

(1) Ar≠Ar' and/or L≠L' (where the symbol "≠" means that groups connected with the symbol have different structures); and (2) when Ar=Ar' and L=L', (2-1) m≠s and/or n≠t, or (2-2) when m=s and n=t, (2-2-1) in the case where L and L' (or pyrene) bind (or binds) to different binding positions on Ar and Ar', or (2-2-2) in the case where L and L' (or pyrene) bind (or binds) to the same binding positions on Ar and Ar', the case where the substitution positions of L and L', or of Ar and Ar' in pyrene are 1- and 6-positions, or 2- and 7-positions does not occur;

an asymmetric anthracene derivative represented by the following general formula (Iv):

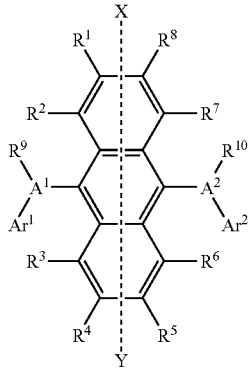

(iv)

where: $A^1$ and $A^2$ each independently represent a substituted or unsubstituted fused aromatic ring group having 10 to 20 ring carbon atoms;

$Ar^1$ and $Ar^2$ each independently represent a hydrogen atom, or a substituted or unsubstituted aromatic ring group having 6 to 50 ring carbon atoms;

$R^1$ to $R^{10}$ each independently represent a hydrogen atom, a substituted or unsubstituted aromatic ring group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group, or a hydroxyl group; and the number of each of $Ar^1$, $Ar^2$, $R^9$, and $R^{10}$ may be two or more, and adjacent groups may form a saturated or unsaturated cyclic structure, provided that the case where groups symmetric with respect to the X-Y axis shown on central anthracene in the general formula (1) bind to 9- and 10-positions of the anthracene does not occur;

an anthracene derivative represented by the following general formula (v):

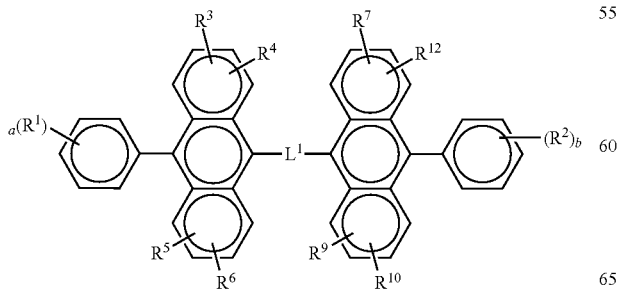

(v)

where: $R^1$ to $R^{10}$ each independently represent a hydrogen atom, an alkyl group, a cycloalkyl group, an aryl group which may be substituted, an alkoxyl group, an aryloxy group, an alkylamino group, an alkenyl group, an arylamino group, or a heterocyclic group which may be substituted; a and b each represent an integer of 1 to 5, and, when a or b represents 2 or more, $R^1$'s or $R^2$'s may be identical to or different from each other, or $R^1$'s or $R^2$'s may be bonded to each other to form a ring; $R^3$ and $R^4$, $R^5$ and $R^6$, $R^7$ and $R^8$, or $R^9$ and $R^{10}$ may be bonded to each other to form a ring; and $L^1$ represents a single bond, —O—, —S—, —N(R)— where R represents an alkyl group or an aryl group which may be substituted, an alkylene group, or an arylene group;

an anthracene derivative represented by the following general formula (vi):

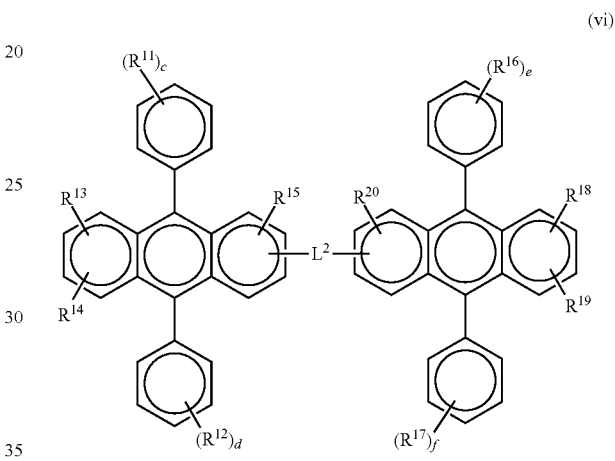

(vi)

where: $R^{11}$ to $R^{20}$ each independently represent a hydrogen atom, an alkyl group, a cycloalkyl group, an aryl group, an alkoxyl group, an aryloxy group, an alkylamino group, an arylamino group, or a heterocyclic group which may be substituted; c, d, e, and f each represent an integer of 1 to 5, and, when any one of c, d, e, and f represents 2 or more, $R^{11}$'s, $R^{12}$'s, $R^{16}$'s, or $R^{17}$'s may be identical to or different from each other, or $R^{11}$'s, $R^{12}$'s, $R^{16}$'s, or $R^{17}$'s may be bonded to each other to form a ring; $R^{13}$ and $R^{14}$, or $R^{18}$ and $R^{19}$ may be bonded to each other to form a ring; and $L^2$ represents a single bond, —O—, —S—, —N(R)— where R represents an alkyl group or an aryl group which may be substituted, an alkylene group, or an arylene group;

a spirofluorene derivative represented by the following general formula (vii):

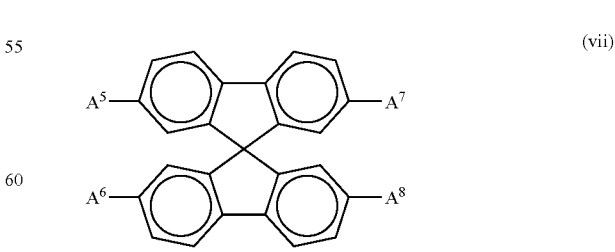

(vii)

where: $A^5$ to $A^8$ each independently represent a substituted or unsubstituted biphenyl group, or a substituted or unsubstituted naphthyl group;

a fused ring-containing compound represented by the following general formula (viii):

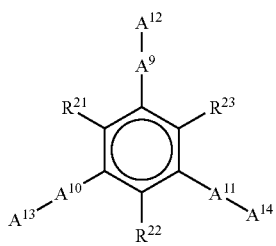

(viii)

where: $A^9$ to $A^{14}$ each have the same meaning as that described above; $R^{21}$ to $R^{23}$ each independently represent a hydrogen atom, an alkyl group having 1 to 6 carbon atoms, a cycloalkyl group having 3 to 6 carbon atoms, an alkoxyl group having 1 to 6 carbon atoms, an aryloxy group having 5 to 18 carbon atoms, an aralkyloxy group having 7 to 18 carbon atoms, an arylamino group having 5 to 16 carbon atoms, a nitro group, a cyano group, an ester group having 1 to 6 carbon atoms, or a halogen atom; and at least one of $A^9$ to $A^{14}$ represents a group having three or more fused aromatic rings;

a fluorene compound represented by the following general formula (ix):

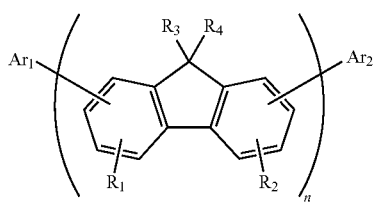

(ix)

where: $R_1$ and $R_2$ each represent a hydrogen atom, a substituted or unsubstituted alkyl group, a substituted or unsubstituted aralkyl group, a substituted or unsubstituted aryl group, a substituted or unsubstituted heterocyclic group, a substituted amino group, a cyano group, or a halogen atom; $R_1$'s or $R_2$'s bonded to different fluorene groups may be identical to or different from each other, and $R_1$ and $R_2$ bonded to the same fluorene group may be identical to or different from each other; $R_3$ and $R_4$ each represent a hydrogen atom, a substituted or unsubstituted alkyl group, a substituted or unsubstituted aralkyl group, a substituted or unsubstituted aryl group, or a substituted or unsubstituted heterocyclic group; $R_3$'s or $R_4$'s bonded to different fluorene groups may be identical to or different from each other, and $R_3$ and $R_4$ bonded to the same fluorene group may be identical to or different from each other; $Ar_1$ and $Ar_2$ each represent a substituted or unsubstituted fused polycyclic aromatic group having three or more benzene rings in total, or a substituted or unsubstituted fused polycyclic heterocyclic group that has three or more rings each of which is a benzene ring or a heterocyclic ring in total and that is bonded to a fluorene group by carbon, and $Ar_1$ and $Ar_2$ may be identical to or different from each other; and n represents an integer of 1 to 10;

a compound having an anthracene central skeleton represented by the following general formula (x):

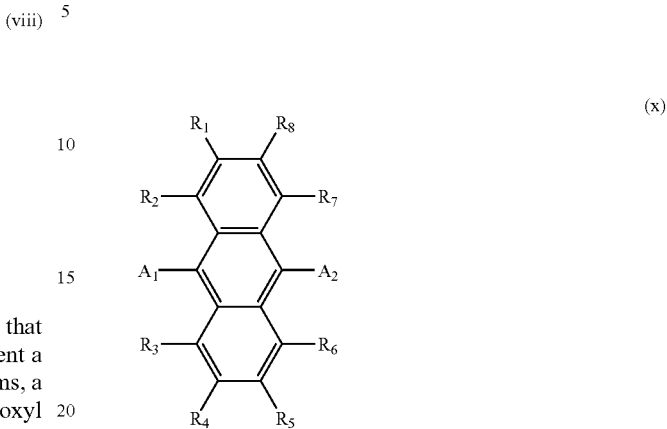

(x)

where: $A_1$ and $A_2$ are each independently a group derived from a substituted or unsubstituted aromatic ring having 6 to 20 ring carbon atoms; the aromatic ring may be substituted with one or two or more substituents;

the substituent is selected from a substituted or unsubstituted aryl group having 6 to 50 ring carbon atoms, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group, and a hydroxyl group;

in the case where the aromatic ring is substituted with two or more substituents, the substituents may be identical to or different from each other, and the adjacent substituents may be bonded with each other to form a saturated or unsaturated cyclic structure; and $R_1$ to $R_8$ are each independently selected from a hydrogen atom, a substituted or unsubstituted aryl group having 6 to 50 ring carbon atoms, a substituted or unsubstituted heteroaryl group having 5 to 50 ring atoms, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group, and a hydroxyl group; and a compound having a structure represented by the following general formula (xi) in which $A_1$ is different from $A_2$ in the general formula (x):

(xi)

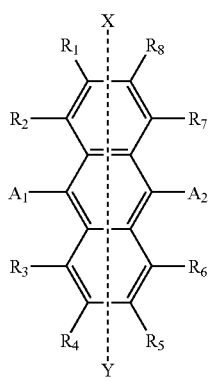

where $A_1$ and $A_2$ and $R_1$ to $R_8$ are each independently have the same meaning as those described in the general formula (x), provided that the case where groups symmetric with respect to the X-Y axis shown on central anthracene bind to 9- and 10-positions of the anthracene does not occur.

Of the above-mentioned host materials, an anthracene derivative is preferable, a monoanthracene derivative is more preferable, and an asymmetric anthracene is particularly preferable.

A host composed of a compound containing a carbazole ring and suitable for phosphorescence is a compound having a function of causing a phosphorescent compound to emit light as a result of the occurrence of energy transfer from the excited state of the host to the phosphorescent compound. The host compound is not particularly limited as long as it is a compound capable of transferring exciton energy to a phosphorescent compound, and can be appropriately selected in accordance with a purpose. The host compound may have, for example, an arbitrary heterocyclic ring in addition to a carbazole ring.

Specific examples of such a host compound include carbazole derivatives, triazole derivatives, oxazole derivatives, oxadiazole derivatives, imidazole derivatives, polyarylalkane derivatives, pyrazoline derivatives, pyrazolone derivatives, phenylene diamine derivatives, arylamine derivatives, amino substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidene-based compounds, porphyrin-based compounds, anthraquinodimethane derivatives, anthrone derivatives, diphenylquinone derivatives, thiopyranedioxide derivatives, carbodiimide derivatives, fluorenilidene methane derivatives, distyryl pyrazine derivatives, heterocyclic tetracarboxylic anhydrides such as naphthaleneperylene, phthalocyanine derivatives, various metal complex polysilane-based compounds typified by metal complexes of 8-quinolinol derivatives or metal complexes having metal phthalocyanine, benzooxazole, or benzothiazole as a ligand, poly(N-vinylcarbazole) derivatives, aniline-based copolymers, conductive high molecular weight oligomers such as thiophene oligomers or polythiophene, polymer compounds such as polythiophene derivatives, polyphenylene derivatives, polyphenylene vinylene derivatives, and polyfluorene derivatives. One of the host materials may be used alone, or two or more thereof may be used in combination.

Specific examples thereof include the compounds as described below.

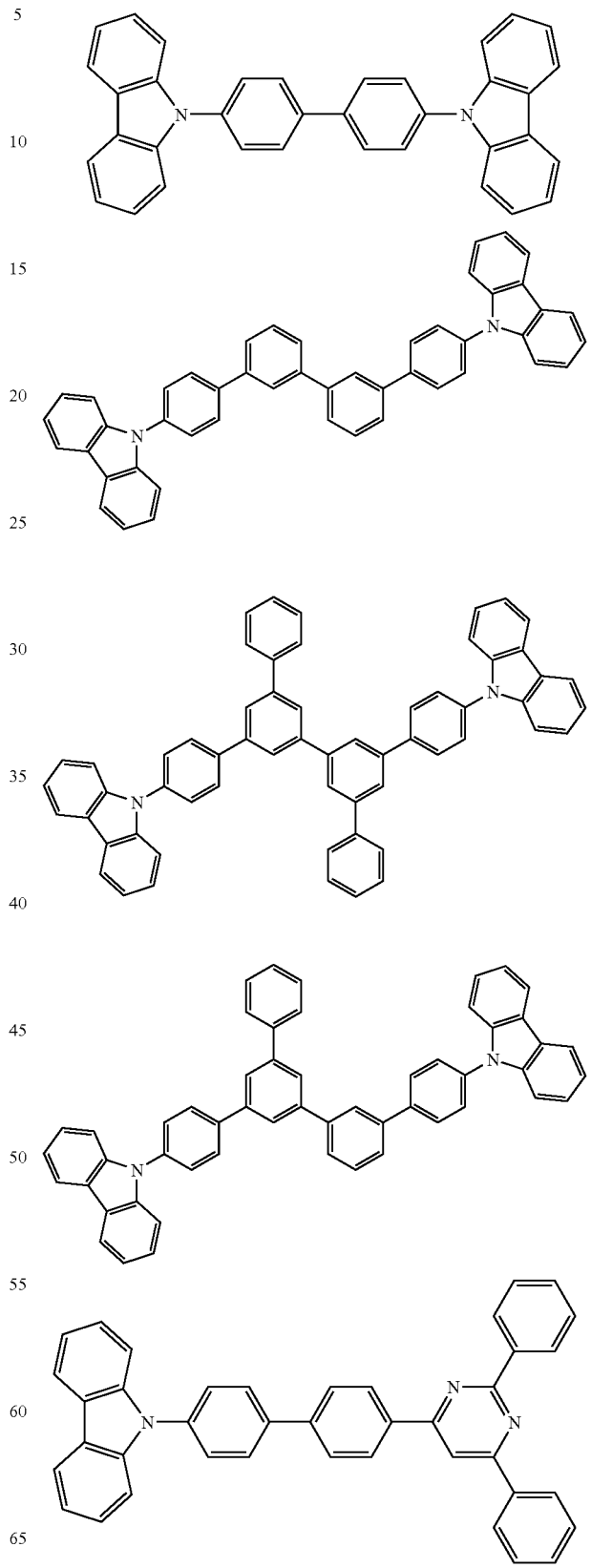

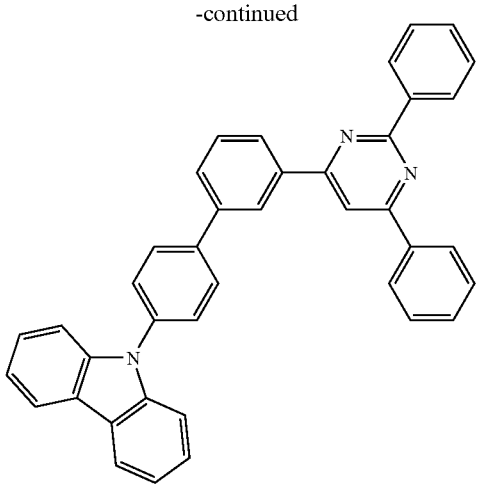

A phosphorescent dopant is a compound capable of emitting light from a triplet exciton. The dopant, which is not particularly limited as long as light is emitted from a triplet exciton, is preferably a metal complex containing at least one metal selected from the group consisting of Ir, Ru, Pd, Pt, Os, and Re, and is preferably a porphyrin metal complex or an orthometalated metal complex. A porphyrin platinum complex is preferable as the porphyrin metal complex. One kind of a phosphorescent compound may be used alone, or two or more kinds of phosphorescent compounds may be used in combination.

Any one of various ligands can be used for forming an orthometalated metal complex. Examples of a preferable ligand include 2-phenylpyridine derivatives, 7,8-benzoquinoline derivatives, 2-(2-thienyl)pyridine derivatives, 2-(1-naphthyl)pyridine derivatives, and 2-phenylquinoline derivatives. Each of those derivatives may have a substituent as required. A fluoride of any one of those derivatives, or one obtained by introducing a trifluoromethyl group into any one of those derivatives is a particularly preferable blue-based dopant. The metal complex may further include a ligand other than the above-mentioned ligands such as acetylacetonato or picric acid as an auxiliary ligand.

The content of the phosphorescent dopant in the light emitting layer is not particularly limited, and can be appropriately selected in accordance with a purpose. The content is, for example, 0.1 to 70 mass %, and is preferably 1 to 30 mass %. When the content of the phosphorescent compound is less than 0.1 mass %, the intensity of emitted light is weak, and an effect of the incorporation of the compound is not sufficiently exerted. When the content exceeds 70 mass %, a phenomenon referred to as concentration quenching becomes remarkable, and device performance reduces.

In addition, the light emitting layer may contain a hole transporting material, an electron transporting material, or a polymer binder as required.

Further, the thickness of the light emitting layer is preferably 5 to 50 nm, more preferably 7 to 50 nm, or most preferably 10 to 50 nm. When the thickness is less than 5 nm, it becomes difficult to form the light emitting layer, so the adjustment of chromaticity may be difficult. When the thickness exceeds 50 nm, the driving voltage may increase.

(5) Hole Injecting and Transporting Layer (Hole Transporting Zone)

The hole injecting and transporting layer is a layer which helps injection of holes into the light emitting layer and transports the holes to the light emitting region. The layer exhibits a great mobility of holes and, in general, has an ionization energy as small as 5.6 eV or smaller. For such the hole injecting and transporting layer, a material which transports holes to the light emitting layer under an electric field of a smaller strength is preferable. A material which exhibits, for example, a mobility of holes of at least $10^{-4}$ cm$^2$/V·sec under application of an electric field of $10^4$ to $10^6$ V/cm is preferable.

When the aromatic amine derivative of the present invention is used in the hole transporting zone, the aromatic amine derivative of the present invention may be used alone or as a mixture with other materials for forming the hole injecting and transporting layer.

The material which can be used for forming the hole injecting and transporting layer as a mixture with the aromatic amine derivative of the present invention is not particularly limited as long as the material has a preferable property described above. The material can be arbitrarily selected from materials which are conventionally used as the charge transporting material of holes in photo conductive materials and known materials which are used for the hole injecting and transporting layer in organic EL devices. In the present invention, the material having a hole transporting ability and is capable of being used in the hole transporting zone is referred to as hole transporting material.

Specific examples include: triazole derivatives (see, for example, U.S. Pat. No. 3,112,197); oxadiazole derivatives (see, for example, U.S. Pat. No. 3,189,447); imidazole derivatives (see, for example, JP-B-37-16096); polyarylalkane derivatives (see, for example, U.S. Pat. No. 3,615,402, U.S. Pat. No. 3,820,989, U.S. Pat. No. 3,542,544, JP-B-45-555, JP-B-51-10983, JP-A-51-93224, JP-A-55-17105, JP-A-56-4148, JP-A-55-108667, JP-A-55-156953, and JP-A-56-36656); pyrazoline derivatives and pyrazolone derivatives (see, for example, U.S. Pat. No. 3,180,729, U.S. Pat. No. 4,278,746, JP-A-55-88064, JP-A-55-88065, JP-A-49-105537, JP-A-55-51086, JP-A-56-80051, JP-A-56-88141, JP-A-57-45545, JP-A-54-112637, and JP-A-55-74546); phenylenediamine derivatives (see, for example, U.S. Pat. No. 3,615,404, JP-B-51-10105, JP-B-46-3712, JP-B-47-25336, and JP-A-54-119925); arylamine derivatives (see, for example, U.S. Pat. No. 3,567,450, U.S. Pat. No. 3,240,597, U.S. Pat. No. 3,658,520, U.S. Pat. No. 4,232,103, U.S. Pat. No. 4,175,961, U.S. Pat. No. 4,012,376, JP-B-49-35702, JP-B-39-27577, JP-A-55-144250, JP-A-56-119132, JP-A-56-22437, and DE 1,110,518); amino-substituted chalcone derivatives (see, for example, U.S. Pat. No. 3,526,501); oxazole derivatives (those disclosed in U.S. Pat. No. 3,257,203); styrylanthracene derivatives (see, for example, JP-A-56-46234); fluorenone derivatives (see, for example, JP-A-54-110837); hydrazone derivatives (see, for example, U.S. Pat. No. 3,717,462, JP-A-54-59143, JP-A-55-52063, JP-A-55-52064, JP-A-55-46760, JP-A-57-11350, JP-A-57-148749, and JP-A-2-311591); stilbene derivatives (see, for example, JP-A-61-210363, JP-A-61-228451, JP-A-61-14642, JP-A-61-72255, JP-A-62-47646, JP-A-62-36674, JP-A-62-10652, JP-A-62-30255, JP-A-60-93445, JP-A-60-94462, JP-A-60-174749, and JP-A-60-175052); silazane derivatives (U.S. Pat. No. 4,950,950); polysilane-based copolymers (JP-A-2-204996); and aniline-based copolymers (JP-A-2-282263).

In addition to the above-mentioned materials which can be used as the material for the hole injecting and transporting layer, a porphyrin compound (those disclosed in, for example, JP-A-63-2956965); an aromatic tertiary amine compound and a styrylamine compound (see, for example, U.S. Pat. No. 4,127,412, JP-A-53-27033, JP-A-54-58445, JP-A-55-79450, JP-A-55-144250, JP-A-56-119132, JP-A-61-295558, JP-A-61-98353, and JP-A-63-295695) are preferable, and aromatic tertiary amine compounds are particularly preferable.

Further, examples of aromatic tertiary amine compounds include compounds having two fused aromatic rings in the molecule such as 4,4'-bis(N-(1-naphthyl)-N-phenylamino)-biphenyl (herein after referred to as NPD) as disclosed in U.S. Pat. No. 5,061,569, and a compound in which three triphenylamine units are bonded together in a star-burst shape, such as 4,4',4"-tris(N-(3-methylphenyl)-N-phenylamino)triphenylamine (herein after referred to as MTDATA) as disclosed in JP-A-4-308688.

In addition, a nitrogen-containing heterocyclic ring derivative represented by the following formula which is disclosed in Japanese Patent No. 3571977 can also be used:

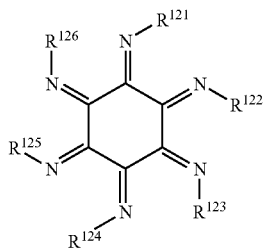

where: $R^{121}$ to $R^{126}$ each represent a substituted or unsubstituted alkyl group, a substituted or unsubstituted aryl group, a substituted or unsubstituted aralkyl group, or a substituted or unsubstituted heterocyclic group, provided that $R^{121}$ to $R^{126}$ may be identical to or different from each other; and $R^{121}$ and $R^{122}$, $R^{123}$ and $R^{124}$, $R^{125}$ and $R^{126}$, $R^{121}$ and $R^{126}$, $R^{122}$ and $R^{123}$, and $R^{124}$ and $R^{125}$ may each form a fused ring.

In addition, a compound represented by the following formula which is described in US 2004-0113547 A can also be used:

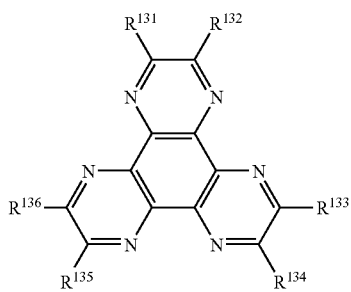

where $R^{131}$ to $R^{136}$ each represent a substituent, preferably an electrophilic group such as a cyano group, a nitro group, a sulfonyl group, a carbonyl group, a trifluoromethyl group, or a halogen.

As typified by those materials, acceptor materials can also be used as the hole injecting material. Specific examples thereof are as described above.

Further, in addition to the aromatic dimethylidine-based compounds described above as the material for the light emitting layer, inorganic compounds such as Si of the p-type and SiC of the p-type can also be used as the material for the hole injecting and transporting layer.

The hole injecting and transporting layer can be formed by forming a thin layer from the aromatic amine derivative of the present invention in accordance with a known process such as the vacuum vapor deposition process, the spin coating process, the casting process, and the LB process. The thickness of the hole injecting and transporting layer is not particularly limited. In general, the thickness is 5 nm to 5 μm. The hole injecting and transporting layer may be formed of a single layer containing one or two or more materials described above or may be a laminate formed of hole injecting and transporting layers containing materials different from the materials of the hole injecting and transporting layer described above as long as the aromatic amine derivative of the present invention is incorporated in the hole transporting zone.

Further, an organic semiconductor layer may be disposed as a layer for helping the injection of holes into the light emitting layer. As the organic semiconductor layer, a layer having a conductivity of $10^{-10}$ S/cm or higher is preferable. As the material for the organic semiconductor layer, the following can be used: oligomers containing thiophene; and conductive oligomers such as oligomers containing arylamine and conductive dendrimers such as dendrimers containing arylamine, which are disclosed in JP-A-8-193191.

(6) Electron Injecting and Transporting Layer

Next, the electron injecting and transporting layer is a layer which helps injection of electrons into the light emitting layer, transports the holes to the light emitting region, and exhibits a great mobility of electrons. The adhesion improving layer is an electron injecting layer including a material exhibiting particularly improved adhesion with the cathode.

In addition, it is known that, in an organic EL device, emitted light is reflected by an electrode (cathode in this case), so emitted light directly extracted from an anode and emitted light extracted via the reflection by the electrode interfere with each other. The thickness of an electron transporting layer is appropriately selected from the range of several nanometers to several micrometers in order that the interference effect may be effectively utilized. When the thickness is particularly large, an electron mobility is preferably at least $10^{-5}$ cm$^2$/Vs or more upon application of an electric field of $10^4$ to $10^6$ V/cm in order to avoid an increase in voltage.

A metal complex of 8-hydroxyquinoline or of a derivative of 8-hydroxyquinoline, or an oxadiazole derivative is suitable as a material to be used in an electron injecting layer. Specific examples of the metal complex of 8-hydroxyquinoline or of the derivative of 8-hydroxyquinoline that can be used as an electron injecting material include metal chelate oxynoid compounds each containing a chelate of oxine (generally 8-quinolinol or 8-hydroxyquinoline), such as tris(8-quinolinol)aluminum.

On the other hand, examples of the oxadiazole derivative include electron transfer compounds represented by the following general formula:

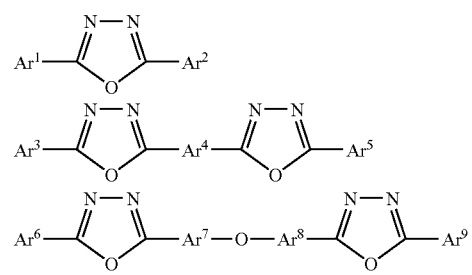

where: $Ar^1$, $Ar^2$, $Ar^3$, $Ar^5$, $Ar^6$ and $Ar^9$ each represent a substituted or unsubstituted aryl group and may represent the same group or different groups; and Ar⁴, Ar⁷ and Ar⁸ each represent a substituted or unsubstituted arylene group and may represent the same group or different groups.

Examples of the aryl group include a phenyl group, a biphenylyl group, an anthryl group, a perylenyl group, and a pyrenyl group. Examples of the arylene group include a phenylene group, a naphthylene group, a biphenylylene group, an anthrylene group, a perylenylene group, and a pyrenylene group. Examples of the substituent include alkyl groups each having 1 to 10 carbon atoms, alkoxyl groups each having 1 to 10 carbon atoms, and a cyano group. As the electron transfer compound, compounds which can form thin films are preferable.

Specific examples of the electron transfer compounds described above include the following.

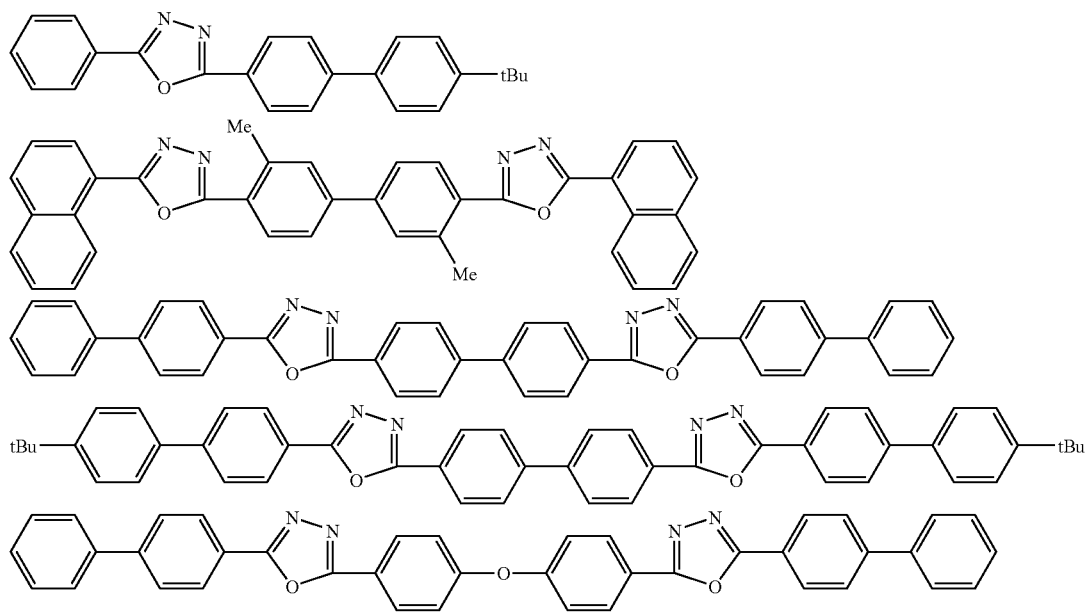

Further, materials represented by the following general formulae (A) to (F) can be used in an electron injecting layer and an electron transporting layer:

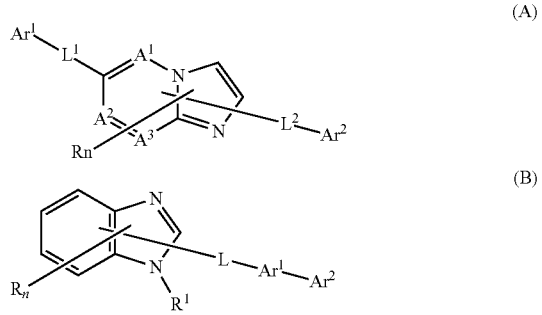

each representing a nitrogen-containing heterocyclic ring derivative, where: $A^1$ to $A^3$ each independently represent a nitrogen atom or a carbon atom;

$Ar^1$ represents, in the formula (A), a substituted or unsubstituted aryl group having 6 to 60 ring carbon atoms, or a substituted or unsubstituted heteroaryl group having 3 to 60 ring carbon atoms; $Ar^1$ represents, in the formula (B), a group in which $Ar^1$ in the formula (A) is made into a divalent arylene group; $Ar^2$ represents a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms, or a substituted or unsubstituted alkoxy group having 1 to 20 carbon atoms, or a divalent group of any one of them; provided that one of $Ar^1$ and $Ar^2$ represents a substituted or unsubstituted fused ring group having 10 to 60 ring carbon atoms, a substituted or unsubstituted monohetero fused ring group having 3 to 60 ring carbon atoms, or a divalent group of any one of them;

$L^1$, $L^2$, and L each independently represent a single bond, a substituted or unsubstituted arylene group having 6 to 60 ring carbon atoms, a substituted or unsubstituted heteroarylene group having 3 to 60 ring carbon atoms, or a substituted or unsubstituted fluorenylene group;

R represents a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms, or a substituted or unsubstituted alkoxy group having 1 to 20 carbon atoms, n represents an integer of 0 to 5, and, when n represents 2 or more, a plurality of R's may be identical to or different from each other, and a plurality of R groups adjacent to each other may be bonded to each other to form a carbocyclic aliphatic ring or a carbocyclic aromatic ring; and $R^1$ represents a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms, a substituted or unsubstituted alkoxy group having 1 to 20 carbon atoms, or -L-$Ar^1$—$Ar^2$;

$$HAr\text{-}L\text{-}Ar^1\text{—}Ar^2 \quad (C)$$

representing a nitrogen-containing heterocyclic ring derivative, where: HAr represents a nitrogen-containing heterocyclic ring which has 3 to 40 carbon atoms and may have a substituent; L represents a single bond, an arylene group which has 6 to 60 carbon atoms and may have a substituent, a heteroarylene group which has 3 to 60 carbon atoms and may have a substituent, or a fluorenylene group which may have a substituent; $Ar^1$ represents a divalent aromatic hydrocarbon group which has 6 to 60 carbon atoms and may have a substituent; and $Ar^2$ represents an aryl group which has 6 to 60 carbon atoms and may have a substituent, or a heteroaryl group which has 3 to 60 carbon atoms and may have a substituent;

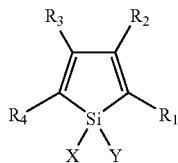

(D)

representing a silacyclopentadiene derivative, where: X and Y each independently represent a saturated or unsaturated hydrocarbon group having 1 to 6 carbon atoms, an alkoxy group, an alkenyloxy group, an alkynyloxy group, a hydroxyl group, a substituted or unsubstituted aryl group, or a substituted or unsubstituted heterocycle, or X and Y are bonded to each other to form a structure as a saturated or unsaturated ring; and $R_1$ to $R_4$ each independently represent hydrogen, a halogen atom, a substituted or unsubstituted alkyl group having 1 to 6 carbon atoms, an alkoxy group, an aryloxy group, a perfluoroalkyl group, a perfluoroalkoxy group, an amino group, an alkylcarbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, a sulfinyl group, a sulfonyl group, a sulfanyl group, a silyl group, carbamoyl group, an aryl group, a heterocyclic group, an alkenyl group, an alkynyl group, a nitro group, a formyl group, nitroso group, a formyloxy group, an isocyano group, a cyanate group, an isocyanate group, a thiocyanate group, an isothiocyanate group, or a cyano group, or, when two substituents are adjacent to each other, they are bonded to each other to form a substituted or unsubstituted and saturated or unsaturated ring;

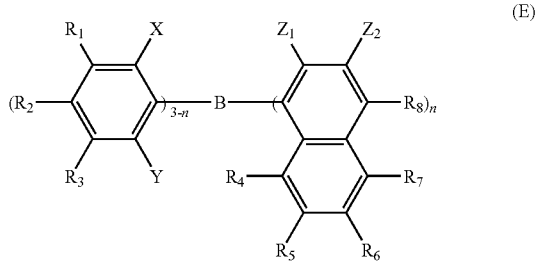

(E)

representing a borane derivative, where: $R_1$ to $R_8$ and $Z_2$ each independently represent a hydrogen atom, a saturated or unsaturated hydrocarbon group, an aromatic group, a heterocyclic group, a substituted amino group, a substituted boryl group, an alkoxy group, or an aryloxy group; X, Y, and $Z_1$ each independently represent a saturated or unsaturated hydrocarbon group, an aromatic group, a heterocyclic group, a substituted amino group, an alkoxy group, or an aryloxy group; substituents of $Z_1$ and $Z_2$ may be bonded to each other to form a fused ring; and n represents an integer of 1 to 3, and, when n represents 2 or more, $Z_1$'s may be different from each other provided that the case where n represents 1, X, Y, and $R_2$ each represent a methyl group, $R_8$ represents a hydrogen atom or a substituted boryl group and the case where n represents 3 and $Z_1$'s each represent a methyl group are excluded; and

(F)

representing a ligand, where: $Q^1$ and $Q^2$ each independently represent a ligand represented by the following general formula (G); and L represents a ligand represented by a halogen atom, a substituted or unsubstituted alkyl group, a substituted or unsubstituted cycloalkyl group, a substituted or unsubstituted aryl group, a substituted or unsubstituted heterocyclic ring group, $-OR^1$ where $R^1$ represents a hydrogen atom, a substituted or unsubstituted alkyl group, a substituted or unsubstituted cycloalkyl group, a substituted or unsubstituted aryl group, or a substituted or unsubstituted heterocyclic ring group, or a ligand represented by $-O-Ga-Q^3(Q^4)$ where $Q^3$ and $Q^4$ have the same meaning as $Q^1$ and $Q^2$, respectively:

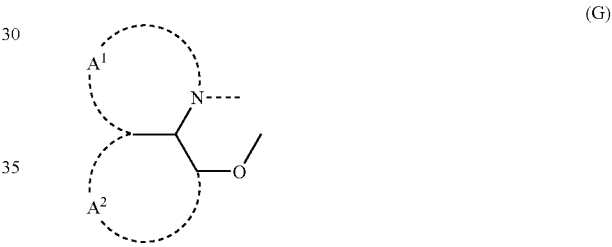

(G)

where rings $A^1$ and $A^2$ are six-membered aryl ring structures which are fused with each other and each of which may have a substituent.

The metal complex behaves strongly as an n-type semiconductor, and has a large electron injecting ability. Further, generation energy upon formation of the complex is low. As a result, the metal and the ligand of the formed metal complex are bonded to each other so strongly that the fluorescent quantum efficiency of the complex as a light emitting material improves.

Specific examples of a substituent in the rings $A^1$ and $A^2$ which each form a ligand of the general formula (G) include: halogen atoms such as chlorine, bromine, iodine, or fluorine; substituted or unsubstituted alkyl groups such as a methyl group, an ethyl group, a propyl group, a butyl group, an s-butyl group, a t-butyl group, a pentyl group, a hexyl group, a heptyl group, an octyl group, a stearyl group, or a trichloromethyl group; substituted or unsubstituted aryl groups such as a phenyl group, a naphthyl group, a 3-methylphenyl group, a 3-methoxyphenyl group, a 3-fluorophenyl group, a 3-trichloromethylphenyl group, a 3-trifluoromethylphenyl group, or a 3-nitrophenyl group; substituted or unsubstituted alkoxy groups such as a methoxy group, an n-butoxy group, a t-butoxy group, a trichloromethoxy group, a trifluoroethoxy group, a pentafluoropropoxy group, a 2,2,3,3-tetra fluoropropoxy group, a 1,1,1,3,3,3-hexa fluoro-2-propoxy group, or a 6-(perfluoroethyl)hexyloxy group; substituted or unsubstituted aryloxy groups such as a phenoxy group, a p-nitrophenoxy group, a p-t-butylphenoxy group, a 3-fluorophenoxy group, a pentafluorophenyl group, or a 3-trifluoromethylphenoxy group; substituted or unsubstituted alkylthio groups such as a methylthio group, an ethylthio group, a t-butylthio group, a hexylthio group, an octylthio group, or a trifluoromethylthio group; substituted or unsubstituted arylthio groups such as a phenylthio group, a p-nitrophenylthio group, a p-t-butylphenylthio group, a 3-fluorophenylthio group, a pentafluorophenylthio group, or a 3-trifluoromethylphenylthio group; mono-substituted or di-substituted amino groups such as a cyano group, a nitro group, an amino group, a methylamino group, a diethylamino group, an ethylamino group, a diethylamino group, a dipropylamino group, a dibutylamino group, or a diphenylamino group; acylamino groups such as a bis(acetoxymethyl)amino group, a bis(acetoxyethyl)amino group, a bis(acetoxypropyl)amino group, or a bis(acetoxybutyl)amino group; carbamoyl groups such as a hydroxyl group, a siloxy group, an acyl group, a methylcarbamoyl group, a dimethylcarbamoyl group, an ethylcarbamoyl group, a diethylcarbamoyl group, a propylcarbamoyl group, a butylcarbamoyl group, or a phenylcarbamoyl group; cycloalkyl groups such as a carboxylic acid group, a sulfonic acid group, an imide group, a cyclopentane group, or a cyclohexyl group; aryl groups such as a phenyl group, a naphthyl group, a biphenylyl group, an anthryl group, a phenanthryl group, a fluorenyl group, or a pyrenyl group; and heterocyclic groups such as a pyridinyl group, a pyrazinyl group, a pyrimidinyl group, a pyridazinyl group, a triazinyl group, an indolinyl group, a quinolinyl group, an acridinyl group, a pyrrolidinyl group, a dioxanyl group, a piperidinyl group, a morpholidinyl group, a piperazinyl group, a carbazolyl group, a furanyl group, a thiophenyl group, an oxazolyl group, an oxadiazolyl group, a benzoxazolyl group, a thiazolyl group, a thiadiazolyl group, a benzothiazolyl group, a triazolyl group, an imidazolyl group, a benzoimidazolyl group, or a puranyl group. In addition, the above-mentioned substituents may be bonded to each other to further form a six-membered aryl ring or a heterocycle.

A preferable embodiment of the organic EL device of the present invention includes an element including a reducing dopant in the region of electron transport or in the interfacial region of the cathode and the organic layer. The reducing dopant is defined as a substance which can reduce a compound having the electron transporting property. Various compounds can be used as the reducing dopant as long as the compounds have a uniform reductive property. For example, at least one substance selected from the group consisting of alkali metals, alkaline earth metals, rare earth metals, alkali metal oxides, alkali metal halides, alkaline earth metal oxides, alkaline earth metal halides, rare earth metal oxides, rare earth metal halides, organic complexes of alkali metals, organic complexes of alkaline earth metals, and organic complexes of rare earth metals can be preferably used.

More specifically, preferable examples of the reducing dopant include substances having a work function of 2.9 eV or smaller, and specific examples of which include at least one alkali metal selected from the group consisting of Li (the work function: 2.9 eV), Na (the work function: 2.36 eV), K (the work function: 2.28 eV), Rb (the work function: 2.16 eV), and Cs (the work function: 1.95 eV) and at least one alkaline earth metal selected from the group consisting of Ca (the work function: 2.9 eV), Sr (the work function: 2.0 to 2.5 eV), and Ba (the work function: 2.52 eV). Of those, at least one alkali metal selected from the group consisting of K, Rb, and Cs is more preferable, Rb and Cs are still more preferable, and Cs is most preferable as the reducing dopant. In particular, those alkali metals have great reducing ability, and the luminance of the emitted light and the lifetime of the organic EL device can be increased by addition of a relatively small amount of the alkali metal into the electron injecting zone. As the reducing dopant having a work function of 2.9 eV or smaller, combinations of two or more alkali metals thereof are also preferable. Combinations having Cs such as the combinations of Cs and Na, Cs and K, Cs and Rb, and Cs, Na, and K are particularly preferable. The reducing ability can be efficiently exhibited by the combination having Cs. The luminance of emitted light and the lifetime of the organic EL device can be increased by adding the combination having Cs into the electron injecting zone.

The present invention may further include an electron injecting layer which is composed of an insulating material or a semiconductor and disposed between the cathode and the organic layer. At this time, the electron injecting property can be improved by preventing a leak of electric current effectively. As the insulating material, at least one metal compound selected from the group consisting of alkali metal chalcogenides, alkaline earth metal chalcogenides, alkali metal halides, and alkaline earth metal halides is preferable. It is preferable that the electron injecting layer be composed of the above-mentioned substance such as the alkali metal chalcogenide since the electron injecting property can be further improved. Preferable examples of the alkali metal chalcogenide include $Li_2O$, $K_2O$, $Na_2S$, $Na_2Se$, and $Na_2O$. To be specific, preferable examples of the alkaline earth metal chalcogenide include CaO, BaO, SrO, BeO, BaS, and CaSe. Preferable examples of the alkali metal halide include LiF, NaF, KF, LiCl, KCl, and NaCl. Preferable examples of the alkaline earth metal halide include fluorides such as $CaF_2$, $BaF_2$, $SrF_2$, $MgF_2$, and $BeF_2$ and halides other than the fluorides.

Examples of the semiconductor composing the electron transporting layer include oxides, nitrides, and oxide nitrides of at least one element selected from Ba, Ca, Sr, Yb, Al, Ga, In, Li, Na, Cd, Mg, Si, Ta, Sb, and Zn used alone or in combination of two or more. It is preferable that the inorganic compound composing the electron transporting layer form a crystallite or amorphous insulating thin film. When the electron transporting layer is composed of the insulating thin film described above, a more uniform thin film can be formed, and defects of pixels such as dark spots can be decreased. Examples of the inorganic compound include alkali metal chalcogenides, alkaline earth metal chalcogenides, alkali metal halides, and alkaline earth metal halides which are described above.

(7) Cathode

As the cathode, a material such as a metal, an alloy, an electroconductive compound, or a mixture of those materials which has a small work function (4 eV or smaller) is used because the cathode is used for injecting electrons to the electron injecting and transporting layer or the light emitting layer. Specific examples of the electrode material include sodium, sodium-potassium alloys, magnesium, lithium, magnesium-silver alloys, aluminum/aluminum oxide, aluminum-lithium alloys, indium, and rare earth metals.

The cathode can be prepared by forming a thin film of the electrode material described above in accordance with a process such as the vapor deposition process or the sputtering process.

When the light emitted from the light emitting layer is obtained through the cathode, it is preferable that the cathode have a transmittance of higher than 10% with respect to the emitted light.

It is also preferable that the sheet resistivity of the cathode be several hundred Ω per square or smaller. The thickness of the cathode is, in general, selected in the range of 10 nm to 1 µm and preferably in the range of 50 to 200 nm.

(8) Insulating Layer

Defects in pixels tend to be formed in organic EL device due to leak and short circuit since an electric field is applied to ultra-thin films. In order to prevent the formation of the defects, a layer of a thin film having an insulating property is preferably inserted between the pair of electrodes.

Examples of the material used for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. Mixtures and laminates of the above-mentioned compounds may also be used.

(9) Method of Producing the Organic EL Device

In order to prepare the organic EL device of the present invention, the anode and the light emitting layer, and, where necessary, the hole injecting and transporting layer and the electron injecting and transporting layer are formed in accordance with the illustrated process using the illustrated materials, and the cathode is formed in the last step. The organic EL device may also be prepared by forming the above-mentioned layers in the order reverse to the order described above, i.e., the cathode being formed in the first step and the anode in the last step.

Hereinafter, an embodiment of the process for preparing an organic EL device having a construction in which an anode, a hole injecting layer, a light emitting layer, an electron injecting layer, and a cathode are disposed successively on a light-transmissive substrate will be described.

On a suitable light-transmissive substrate, a thin film made of a material for the anode is formed in accordance with the vapor deposition process or the sputtering process so that the thickness of the formed thin film is 1 µm or smaller and preferably in the range of 10 to 200 nm. The formed thin film is used as the anode. Then, a hole injecting layer is formed on the anode. The hole injecting layer can be formed in accordance with the vacuum vapor deposition process, the spin coating process, the casting process, or the LB process, as described above. The vacuum vapor deposition process is preferable since a uniform film can be easily obtained and the possibility of formation of pin holes is small. When the hole injecting layer is formed in accordance with the vacuum vapor deposition process, in general, it is preferable that the conditions be suitably selected in the following ranges: the temperature of the source of the deposition: 50 to 450° C.; the vacuum: $10^{-7}$ to $10^{-3}$ Torr; the rate of deposition: 0.01 to 50 nm/second; the temperature of the substrate: −50 to 300° C.; and the thickness of the film: 5 nm to 5 µm although the conditions of the vacuum vapor deposition are different depending on the compound to be used (i.e., material for the hole injecting layer) and the crystal structure and the recombination structure of the target hole injecting layer.

Then, the light emitting layer is formed on the hole injecting layer. A thin film of the organic light emitting material can be formed by using a desired organic light emitting material in accordance with a process such as the vacuum vapor deposition process, the sputtering process, the spin coating process, or the casting process, and the formed thin film is used as the light emitting layer. The vacuum vapor deposition process is preferable since a uniform film can be easily obtained and the possibility of formation of pin holes is small. When the light emitting layer is formed in accordance with the vacuum vapor deposition process, in general, the conditions of the vacuum vapor deposition process can be selected in the same ranges as the conditions described for the vacuum vapor deposition of the hole injecting layer, although the conditions are different depending on the compound to be used.

Next, an electron injecting layer is formed on the light emitting layer. Similarly to the hole injecting layer and the light emitting layer, it is preferable that the electron injecting layer be formed in accordance with the vacuum vapor deposition process since a uniform film must be obtained. The conditions of the vacuum vapor deposition can be selected in the same ranges as the condition described for the vacuum vapor deposition of the hole injecting layer and the light emitting layer.

When the vapor deposition process is used, the aromatic amine derivative of the present invention can be deposited by vapor in combination with other materials, although the situation may be different depending on which layer in the light emitting zone or in the hole transporting zone includes the compound. When the spin coating process is used, the compound can be incorporated into the formed layer by using a mixture of the compound with other materials.

A cathode is laminated in the last step, and an organic EL device can be obtained.

The cathode is formed of a metal and can be formed in accordance with the vacuum vapor deposition process or the sputtering process. It is preferable that the vacuum vapor deposition process be used in order to prevent formation of damages on the lower organic layers during the formation of the film.

In the above-mentioned preparation of the organic EL device, it is preferable that the above-mentioned layers from the anode to the cathode be formed successively while the preparation system is kept in a vacuum after being evacuated once.

The method of forming the layers in the organic EL device of the present invention is not particularly limited. A conventionally known process such as the vacuum vapor deposition process or the spin coating process can be used. The organic thin film layer which is used in the organic EL device of the present invention and includes the compound represented by general formula (1) described above can be formed in accordance with a known process such as the vacuum vapor deposition process or the molecular beam epitaxy process (MBE process) or, using a solution prepared by dissolving the compounds into a solvent, in accordance with a coating process such as the dipping process, the spin coating process, the casting process, the bar coating process, or the roll coating process.

The thickness of each layer in the organic thin film layer in the organic EL device of the present invention is not particularly limited. In general, an excessively thin layer tends to have defects such as pin holes, where as an excessively thick layer requires a high applied voltage to decrease the efficiency. Therefore, a thickness in the range of several nanometers to 1 µm is preferable.

The organic EL device which can be prepared as described above emits light when a direct voltage of 5 to 40 V is applied in the condition that the polarity of the anode is positive (+) and the polarity of the cathode is negative (−). When the polarity is reversed, no electric current is observed and no light is emitted at all. When an alternating voltage is applied to the organic EL device, the uniform light emission is observed only in the condition that the polarity of the anode is positive and the polarity of the cathode is negative. When an alternating voltage is applied to the organic EL device, any type of wave shape can be used.

EXAMPLES
Hereinafter, the present invention is described in more detail on the basis of Synthesis Examples and Examples.
Structural formulae representing Intermediates 1 to 22 produced in Synthesis Examples 1 to 22 are as follows.
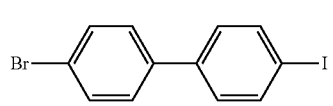
Intermediate1
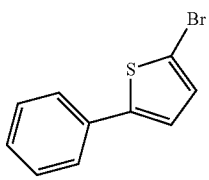
Intermediate2
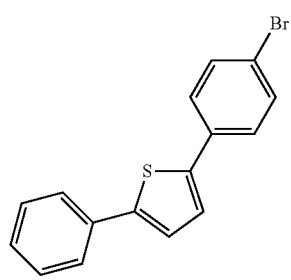
Intermediate3
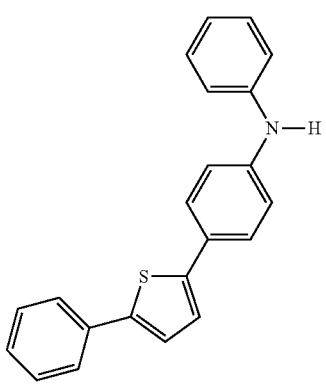
Intermediate4
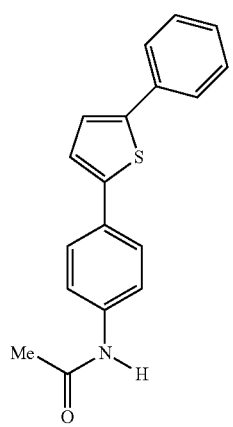
Intermediate5
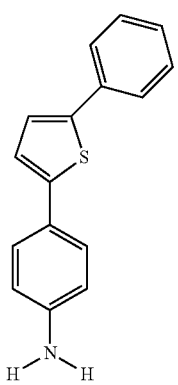
Intermediate6
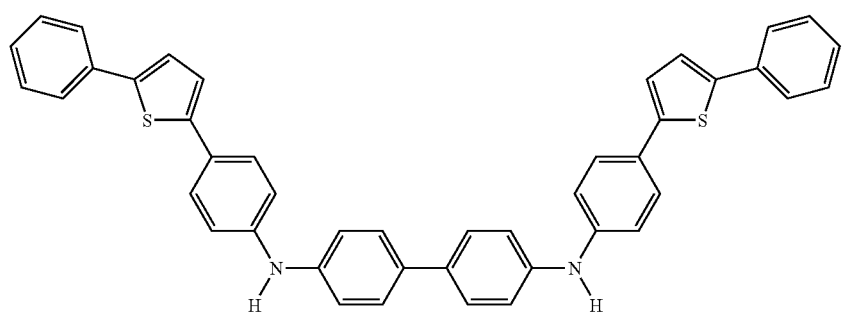
Intermediate7

-continued
Intermediate8
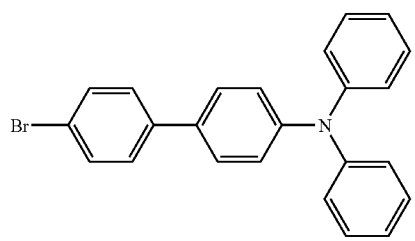
Intermediate9
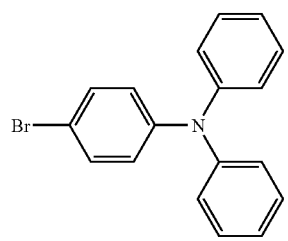
Intermediate10
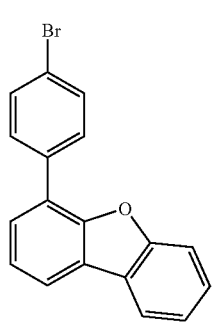
Intermediate11
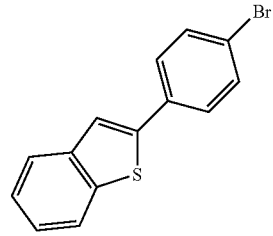
Intermediate12
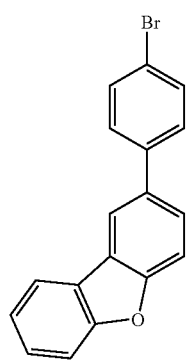
Intermediate13
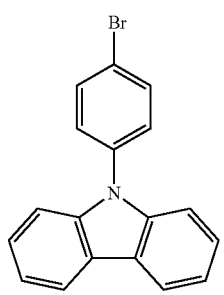
Intermediate14
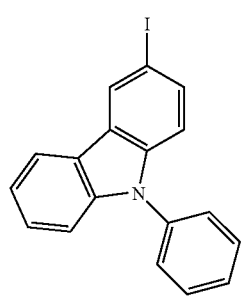
Intermediate15
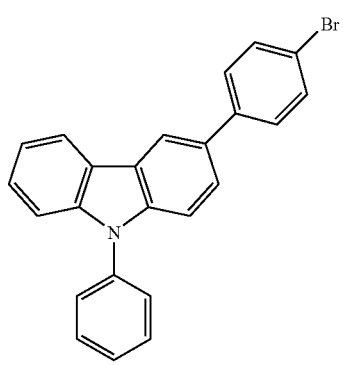

-continued
Intermediate16
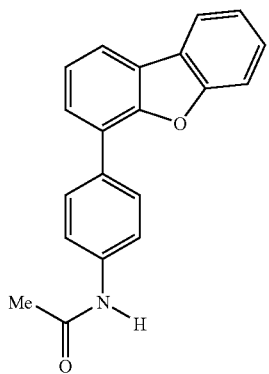
Intermediate17
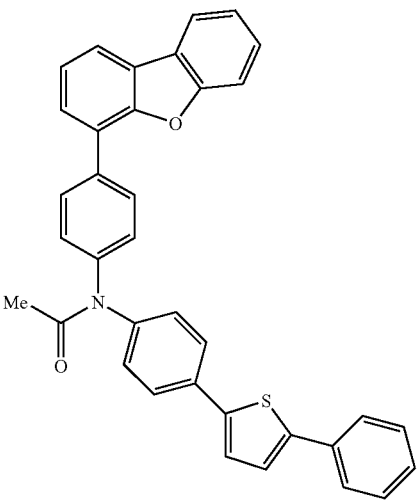
Intermediate18
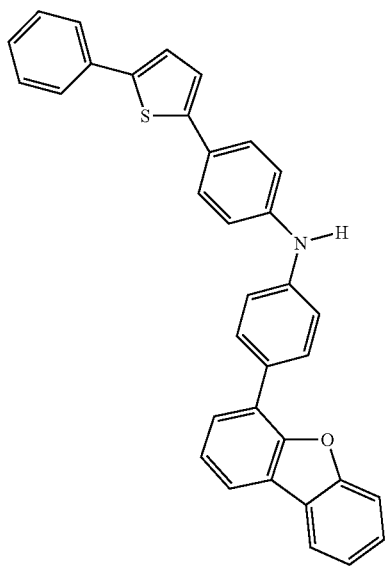
Intermediate19
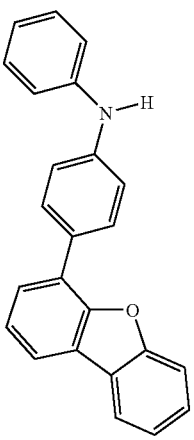
Intermediate20
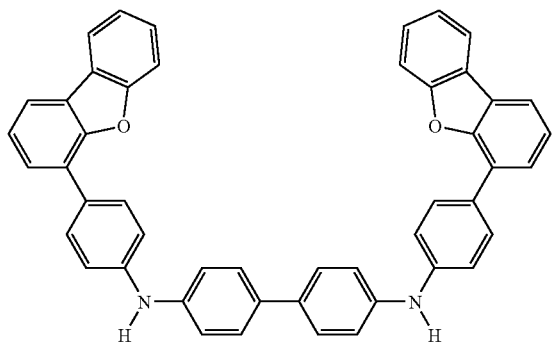
Intermediate21
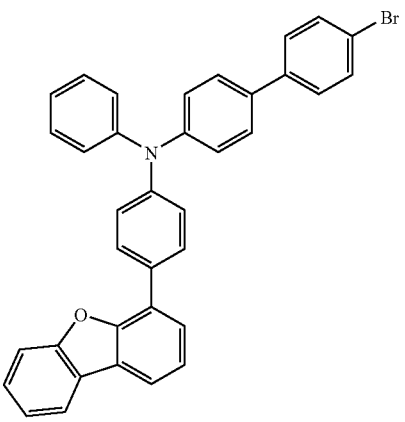

Intermediate 22

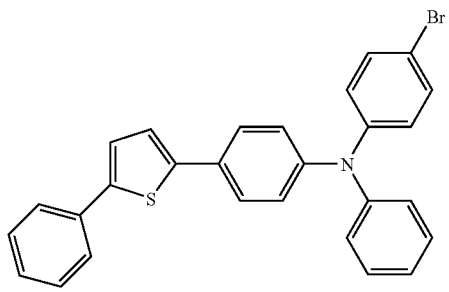

Synthesis Example 1

Synthesis of Intermediate 1

Under an argon stream, to a 1,000-mL three-necked flask, 47 g of 4-bromobiphenyl, 23 g of iodine, 9.4 g of periodic acid dihydrate, 42 mL of water, 360 mL of acetic acid, and 11 mL of sulfuric acid were charged, and the mixture was stirred at 65° C. for 30 minutes and then reacted at 90° C. for 6 hours. The reactant was poured into ice water, followed by filtering. The resultant was washed with water, and then washed with methanol, whereby 67 g of white powder was obtained. By a field desorption mass spectrometry (FD-MS) analysis, main peaks of m/z=358 and m/z=360 with respect to $C_{12}H_{15}BrI=359$ were obtained, so the white powder was identified as Intermediate 1.

Synthesis Example 2

Synthesis of Intermediate 2

Under an argon stream, to a 50-L reaction container, 750 g of phenylboronic acid, 1,000 g of 2-bromothiophene, 142 g of tetrakis(triphenylphosphine)palladium $(Pd(PPh_3)_4)$, 9 L of 2 M sodium carbonate $(Na_2CO_3)$ solution, and 15 L of dimethoxyethane were charged, and the mixture was reacted at 80° C. for 8 hours. The reactant was extracted with toluene and water, followed by drying with anhydrous sodium sulfate. The resultant was concentrated under reduced pressure, and the obtained crude product was subjected to column purification, whereby 786 g of white powder was obtained.

Under an argon stream, to a 20-L reaction container, 786 g of the compound obtained above and 8 L of dimethylformamide (DMF) were charged, followed by adding slowly 960 g of N-bromosuccinimide (NBS), and the mixture was reacted at room temperature for 12 hours. The reactant was extracted with hexane and water, followed by drying with anhydrous sodium sulfate. The resultant was concentrated under reduced pressure, and the obtained crude product was subjected to column purification, whereby 703 g of white powder was obtained. By an FD-MS analysis, the white powder was identified as Intermediate 2.

Synthesis Example 3

Synthesis of Intermediate 3

Under an argon stream, to a 20-L reaction container, 703 g of Intermediate 2 and 7 L of dehydrated tetra hydrofuran (THF) were charged, and the mixture was cooled to −30° C. 2.3 L of n-BuLi (1.6 M hexane solution) was added thereto, and the mixture was reacted for 1 hour. After the resultant was cooled to −70° C., 1,658 g of Boric Acid Triisopropyl Ester (manufactured by Tokyo Chemical Industry Co., Ltd.) was added thereto. The temperature of the mixture was raised slowly, and the mixture was stirred at room temperature for 1 hour. 1.7 L of 10%-hydrochloric acid solution was added thereto and the mixture was stirred. The mixture was extracted with ethyl acetate and water, and an organic layer was washed with water. The resultant was dried with anhydrous sodium sulfate to thereby distill off the solvent. The resultant was washed with hexane, whereby 359 g of white powder was obtained.

Under an argon stream, to a 20-L reaction container, 506 g of 5-phenyl-2-thiopheneboronic acid obtained above, 600 g of 4-iodobromobenzene, 41 g of tetrakis(triphenylphosphine) palladium $(Pd(PPh_3)_4)$, 2.6 L of 2 M sodium carbonate $(Na_2CO_3)$ solution, and 10 L of dimethoxyethane were charged, and the mixture was reacted at 80° C. for 8 hours. The reactant was extracted with toluene and water, followed by drying with anhydrous sodium sulfate. The resultant was concentrated under reduced pressure, and the obtained crude product was subjected to column purification, whereby 277 g of white powder was obtained. By an FD-MS analysis, the white powder was identified as Intermediate 3.

Synthesis Example 4

Synthesis of Intermediate 4

Under an argon stream, 5.5 g of aniline, 15.7 g of Intermediate 3, 6.8 g of sodium t-butoxide (manufactured by Hiroshima Wako Co., Ltd.), 0.46 g of tris(dibenzylideneacetone)dipalladium(0) (manufactured by Aldrich Chemical Company, Inc.), and 300 mL of dehydrated toluene were charged, and the mixture was reacted at 80° C. for 8 hours.

After the reactant was cooled, 500 mL of water was added thereto, and the mixture was filtered with celite. The filtrate was extracted with toluene and dried with anhydrous magnesium sulfate. The resultant was concentrated under reduced pressure, and the obtained crude product was subjected to column purification. The purified product was recrystallized with toluene, followed by filtration and drying, whereby 10.8 g of pale yellow powder was obtained. By an FD-MS analysis, the pale yellow powder was identified as Intermediate 4.

Synthesis Example 5

Synthesis of Intermediate 5

Under an argon stream, 185 g of 1-acetamide (manufactured by Tokyo Chemical Industry Co., Ltd.), 315 g of Intermediate 3 (manufactured by Wako Pure Chemical Industries, Ltd.), 544 g of potassium carbonate (manufactured by Wako Pure Chemical Industries, Ltd.), 12.5 g of copper powder (manufactured by Wako Pure Chemical Industries, Ltd.), and 2 L of decalin, and the mixture was reacted at 190° C. for 4 days. The reactant was cooled after the reaction and added with 2 L of toluene, followed by filtration of the insolubles. The filtered product was dissolved in 4.5 L of chloroform and the insolubles were removed. After that, the resultant was subjected to activated carbon treatment and then concentrated. 3 L of acetone was added thereto, and 175 g of precipitated crystal was obtained by filtration. By an FD-MS analysis, the precipitated crystal was identified as Intermediate 5.

Synthesis Example 6

Synthesis of Intermediate 6

Under an argon stream, Intermediate 5 was suspended in 5 L of ethylene glycol (manufactured by Wako Pure Chemical Industries, Ltd.) and 50 mL of water, and 210 g of 85%-potassium hydroxide aqueous solution was added thereto, followed by reaction at 120° C. for 8 hours. After the reaction, the reaction solution was poured into 10 L of water, precipitated crystal was obtained by filtration, and the precipitated crystal was washed with water and methanol. The obtained crystal was dissolved in 3 L of tetra hydrofuran while heating, and the resultant was subjected to activated carbon treatment followed by concentration. Subsequently, the crystal was precipitated by adding acetone therein. The precipitated crystal was obtained by filtration, whereby 145 g of white powder was obtained. By an FD-MS analysis, the white powder was identified as Intermediate 6.

Synthesis Example 7

Synthesis of Intermediate 7

Under an argon stream, 185 g of 1-acetamide (manufactured by Tokyo Chemical Industry Co., Ltd.), 315 g of Intermediate 3 (manufactured by Wako Pure Chemical Industries, Ltd.), 544 g of potassium carbonate (manufactured by Wako Pure Chemical Industries, Ltd.), 12.5 g of copper powder (manufactured by Wako Pure Chemical Industries, Ltd.), and 2 L of decalin, and the mixture was reacted at 190° C. for 4 days. The reactant was cooled after the reaction and added with 2 L of toluene, followed by filtration of the insolubles. The filtered product was dissolved in 4.5 L of chloroform and the insolubles were removed. After that, the resultant was subjected to activated carbon treatment and then concentrated. 3 L of acetone was added thereto, and 175 g of precipitated crystal was obtained by filtration.

To the precipitated crystal, 120 g of 4-4'-diiodobiphenyl (manufactured by Wako Pure Chemical Industries, Ltd.), 163 g of potassium carbonate (manufactured by Wako Pure Chemical Industries, Ltd.), 3.8 g of copper powder (manufactured by Wako Pure Chemical Industries, Ltd.), and 600 mL of decalin was charged, and the mixture was reacted at 190° C. for 4 days.

The reactant was cooled after the reaction and added with 600 mL of toluene, followed by filtration of the insolubles. The filtered product was dissolved in 1.4 L of chloroform and the insolubles thereof were removed. After that, the resultant was subjected to activated carbon treatment and then concentrated. 1 L of acetone was added thereto, and 382 g of precipitated crystal was obtained by filtration.

The precipitated crystal was suspended in 1.5 L of ethylene glycol (manufactured by Wako Pure Chemical Industries, Ltd.) and 15 mL of water, and 44 g of 85% potassium hydroxide aqueous solution was added thereto, followed by reaction at 12° C. for 8 hours. After the reaction, the reaction solution was poured into 10 L of water, precipitated crystal was obtained by filtration, and the precipitated crystal was washed with water and methanol. The obtained crystal was dissolved in 1 L of tetra hydrofuran while heating, and the resultant was subjected to activated carbon treatment followed by concentration. Subsequently, the crystal was precipitated by adding acetone therein. The precipitated crystal was obtained by filtration, where by 130 g of white powder was obtained. By an FD-MS analysis, the white powder was identified as Intermediate 7.

Synthesis Example 8

Synthesis of Intermediate 8

Under an argon stream, 5.1 g of diphenylamine, 10.8 g of Intermediate 1, 3 g of sodium t-butoxide (manufactured by Hiroshima Wako Co., Ltd.), 0.5 g of bis(triphenylphosphine) palladium(II) chloride (manufactured by Tokyo Chemical Industry Co., Ltd.), and 500 mL of xylene were charged, and the mixture was reacted at 130° C. for 24 hours.

After the reactant was cooled, 1,000 mL of water was added thereto, and the mixture was filtered with celite. The filtrate was extracted with toluene and dried with anhydrous magnesium sulfate. The resultant was concentrated under reduced pressure, and the obtained crude product was subjected to column purification. The purified product was recrystallized with toluene, followed by filtration and drying, whereby 3.4 g of pale yellow powder was obtained. By an FD-MS analysis, the pale yellow powder was identified as Intermediate 8.

Synthesis Example 9

Synthesis of Intermediate 9

The same reaction as in Synthesis Example 8 was carried out except that 4-iodobromobenzene was used instead of Intermediate 1, whereby 2.8 g of white powder was obtained. By an FD-MS analysis, the white powder was identified as Intermediate 9.

Synthesis Example 10

Synthesis of Intermediate 10

Under an argon stream, 536 g of commercially-available 4-dibenzofuranboronic acid, 600 g of 4-iodobromobenzene, 41 g of tetrakis(triphenylphosphine)palladium ($Pd(PPh_3)_4$), 2.6 L of 2 M sodium carbonate ($Na_2CO_3$) solution, and 10 L of dimethoxyethane were charged, and the mixture was reacted at 80° C. for 8 hours. The reactant was extracted with toluene and water, followed by drying with anhydrous sodium sulfate. The resultant was concentrated under reduced pressure, and the obtained crude product was subjected to column purification, whereby 257 g of white powder was obtained. By an FD-MS analysis, the white powder was identified as Intermediate 10.

Synthesis Example 11

Synthesis of Intermediate 11

The same reaction as in Synthesis Example 10 was carried out except that thianaphthene-2-boronic acid was used instead of 4-dibenzofuranboronic acid, whereby 241 g of white powder was obtained. By an FD-MS analysis, the white powder was identified as Intermediate 11.

Synthesis Example 12

Synthesis of Intermediate 12

Under an argon stream, 150 g of dibenzofuran and 1 L of acetic acid were charged, dibenzofuran was dissolved in acetic acid while heating, and 188 g of bromine was dropped thereinto. The crystal was filtered and washed with acetic acid and water, followed by recrystallization with methanol, whereby 97 g of a bromo compound was obtained. The same reaction as in Synthesis Example 3 was carried out except that the bromo compound was used instead of Intermediate 2, whereby 46 g of white powder was obtained. By an FD-MS analysis, the white powder was identified as Intermediate 12.

Synthesis Example 13

Synthesis of Intermediate 13

The same reaction as in Synthesis Example 9 was carried out except that carbazole was used instead of diphenylamine, whereby 28 g of white powder was obtained. By an FD-MS analysis, the white powder was identified as Intermediate 13.

Synthesis Example 14

Synthesis of Intermediate 14

Under an argon stream, 670 g of carbazole, 850 kg of iodobenzene, 20 L of xylene, 460 g of t-BuONa, and palladium acetate (Pd (OAc)) were charged, and the mixture was refluxed for 8 hours. Impurities were filtered and the filtrate was concentrated under reduced pressure, followed by washing with hexane and drying, whereby phenylcarbazole was obtained as 820 g of white powder. The same reaction as in the synthesis of Intermediate 1 was carried out except that phenylcarbazole was used instead of 4-bromobiphenyl, whereby 650 g of white powder was obtained. By an FD-MS analysis, the white powder was identified as Intermediate 14.

Synthesis Example 15

Synthesis of Intermediate 15

The same reaction as in Synthesis Example 3 was carried out except that Intermediate 14 was used instead of Intermediate 2, whereby 250 g of white powder was obtained. By an FD-MS analysis, the white powder was identified as Intermediate 15.

Synthesis Example 16

Synthesis of Intermediate 16

The same reaction as in Synthesis Example 5 was carried out except that Intermediate 10 was used instead of Intermediate 3, whereby 210 g of white powder was obtained. By an FD-MS analysis, the white powder was identified as Intermediate 16.

Synthesis Example 17

Synthesis of Intermediate 17

The same reaction as in Synthesis Example 5 was carried out except that Intermediate 16 was used instead of acetamide, whereby 250 g of white powder was obtained. By an FD-MS analysis, the white powder was identified as Intermediate 17.

Synthesis Example 18

Synthesis of Intermediate 18

The same reaction as in Synthesis Example 6 was carried out except that Intermediate 17 was used instead of Intermediate 5, whereby 163 g of white powder was obtained. By an FD-MS analysis, the white powder was identified as Intermediate 18.

Synthesis Example 19

Synthesis of Intermediate 19

The same reaction as in Synthesis Example 4 was carried out except that Intermediate 10 was used instead of Intermediate 3, whereby 9.2 g of white powder was obtained. By an FD-MS analysis, the white powder was identified as Intermediate 19.

Synthesis Example 20

Synthesis of Intermediate 20

The same reaction as in Synthesis Example 7 was carried out except that Intermediate 10 was used instead of Intermediate 3, whereby 116 g of white powder was obtained. By an FD-MS analysis, the white powder was identified as Intermediate 20.

Synthesis Example 21

Synthesis of Intermediate 21

The same reaction as in Synthesis Example 8 was carried out except that Intermediate 19 was used instead of diphenylamine and 4-iodobromobenzene was used instead of Intermediate 1, whereby 3.5 g of white powder was obtained. By an FD-MS analysis, the white powder was identified as Intermediate 21.

Synthesis Example 22

Synthesis of Intermediate 22

The same reaction as in Synthesis Example 8 was carried out except that Intermediate 4 was used instead of diphenylamine, whereby 2.9 g of white powder was obtained. By an FD-MS analysis, the white powder was identified as Intermediate 22.

Structural formulae representing Compounds H1 to H18, which are aromatic amine derivatives of the present invention produced in Synthesis Embodiments 1 to 18, are as follows.

133    134
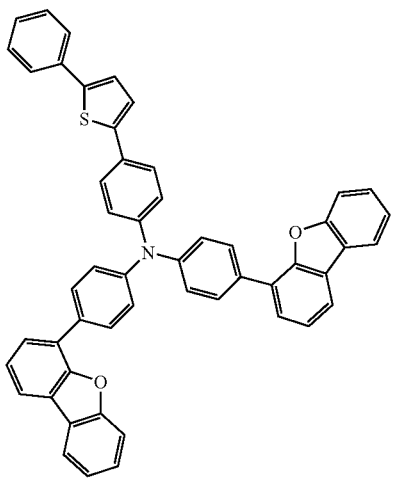
H1
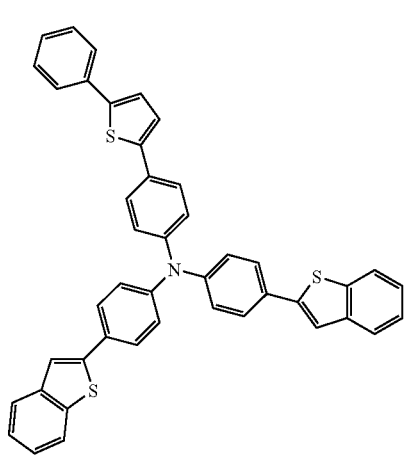
H2
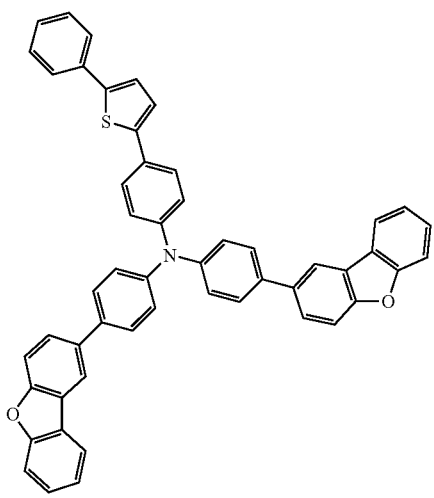
H3
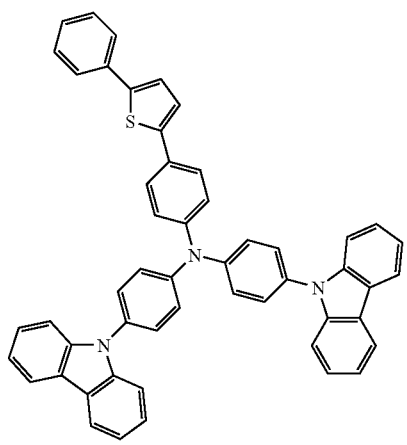
H4
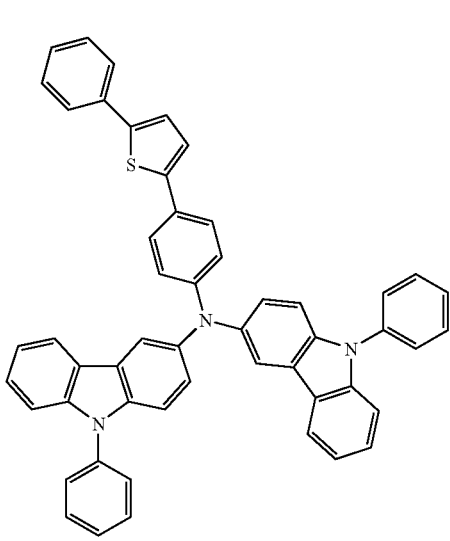
H5
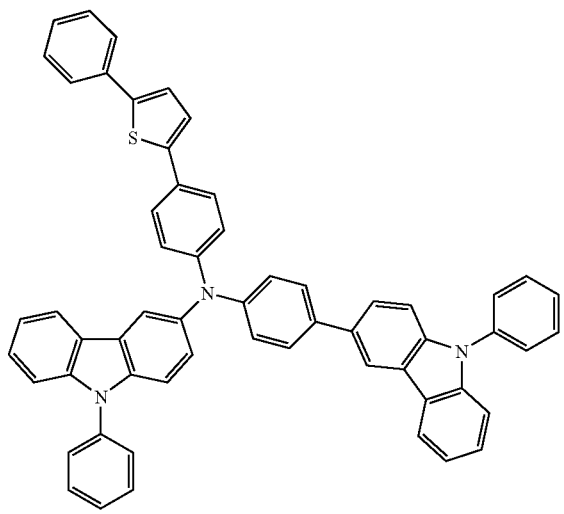
H6

H7
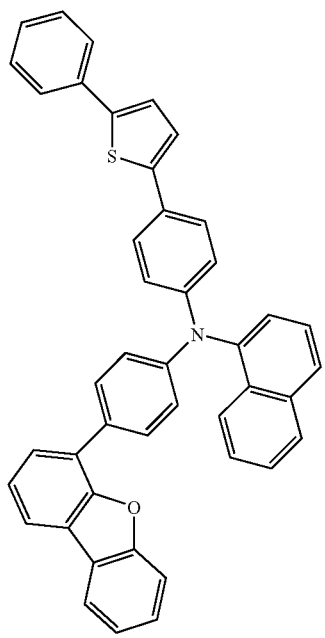
H8
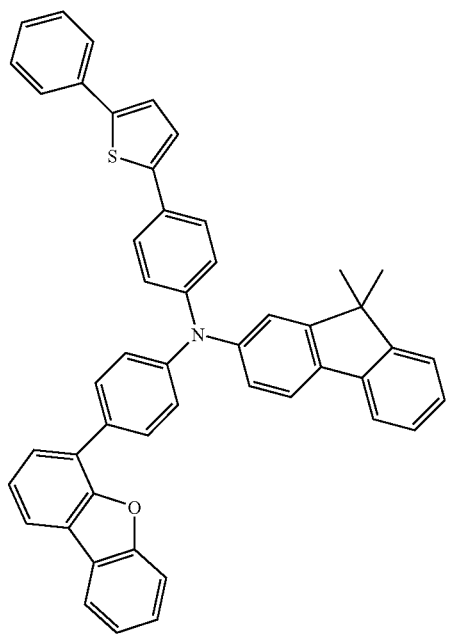
H9
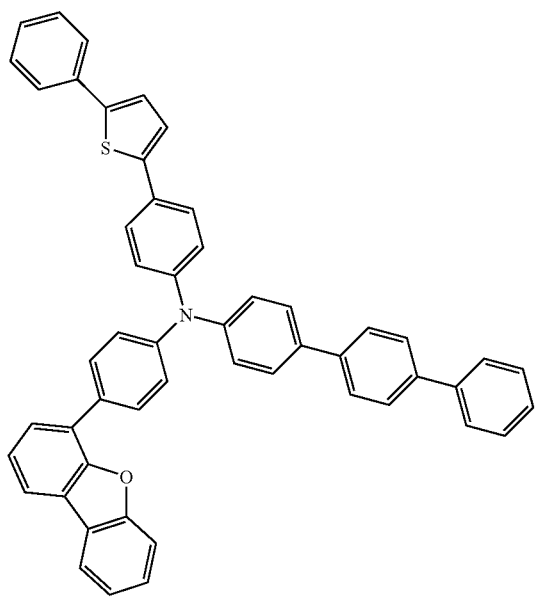
H10
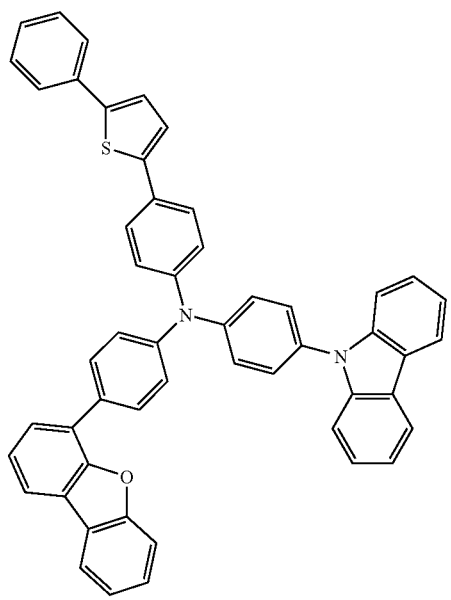

-continued
H11
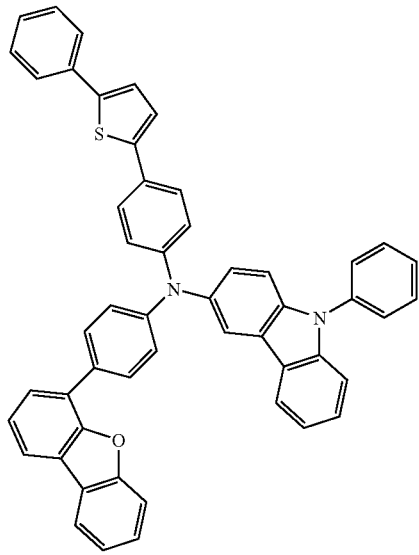
H12
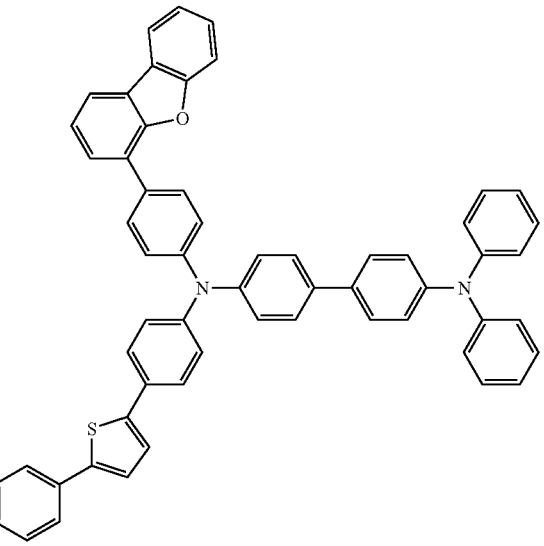
H13
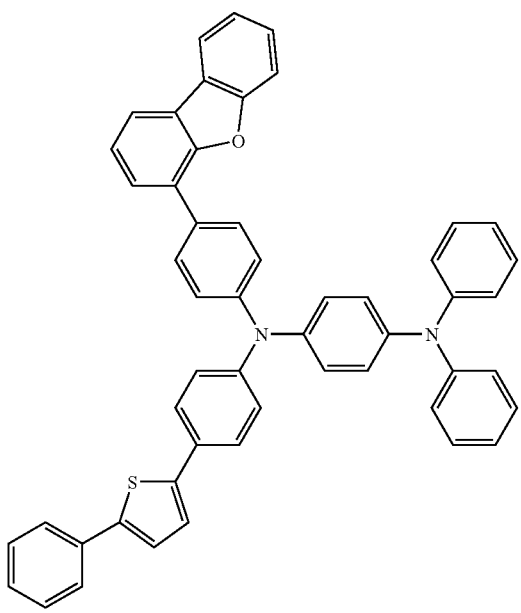

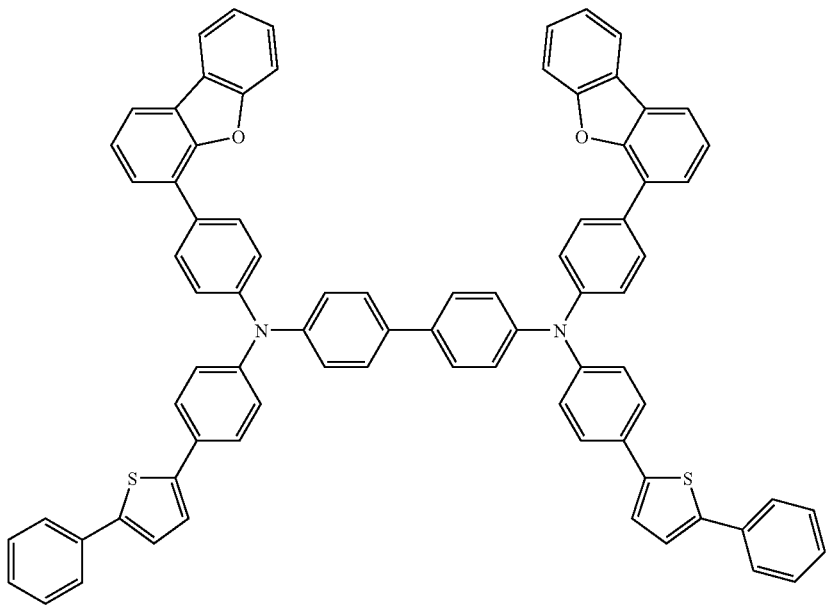
H14
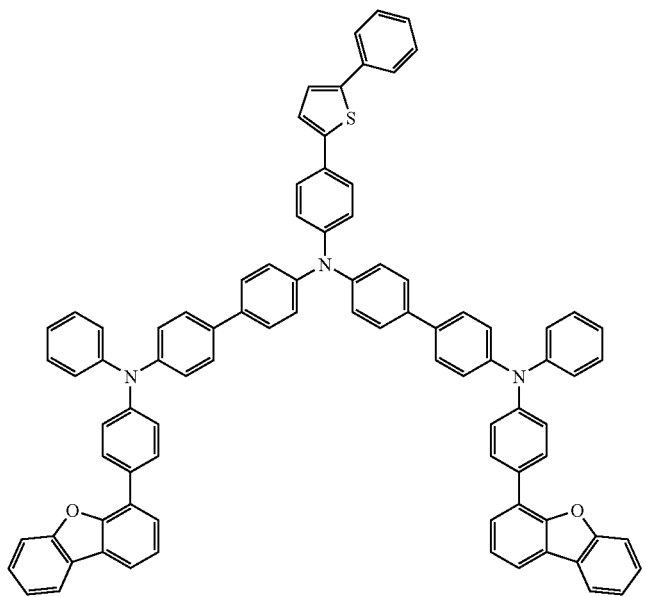
H15

H16
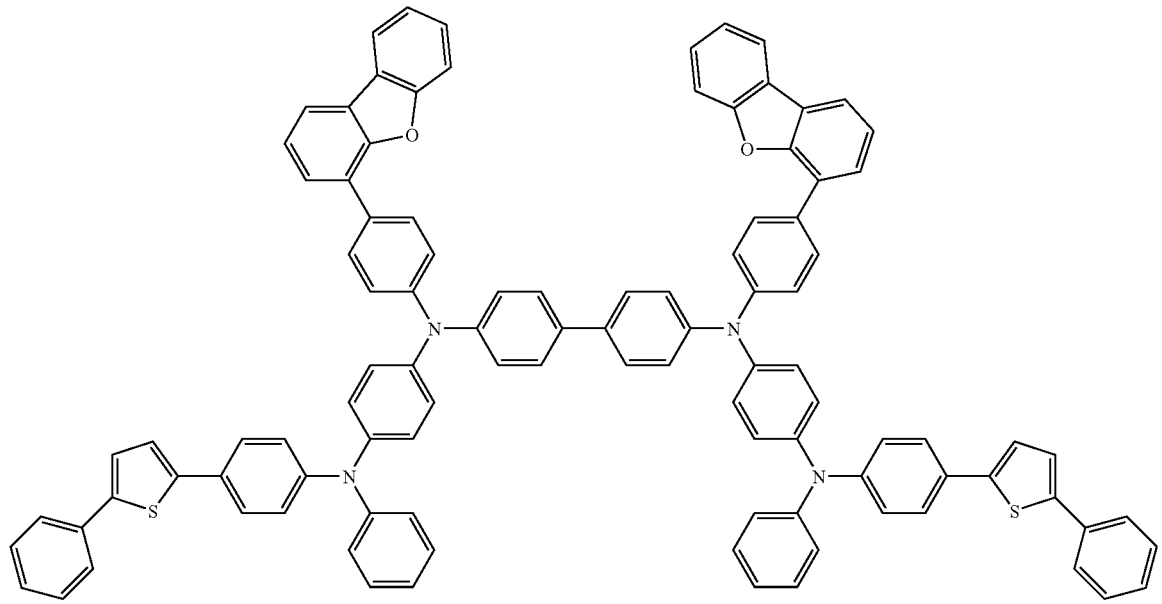
H17
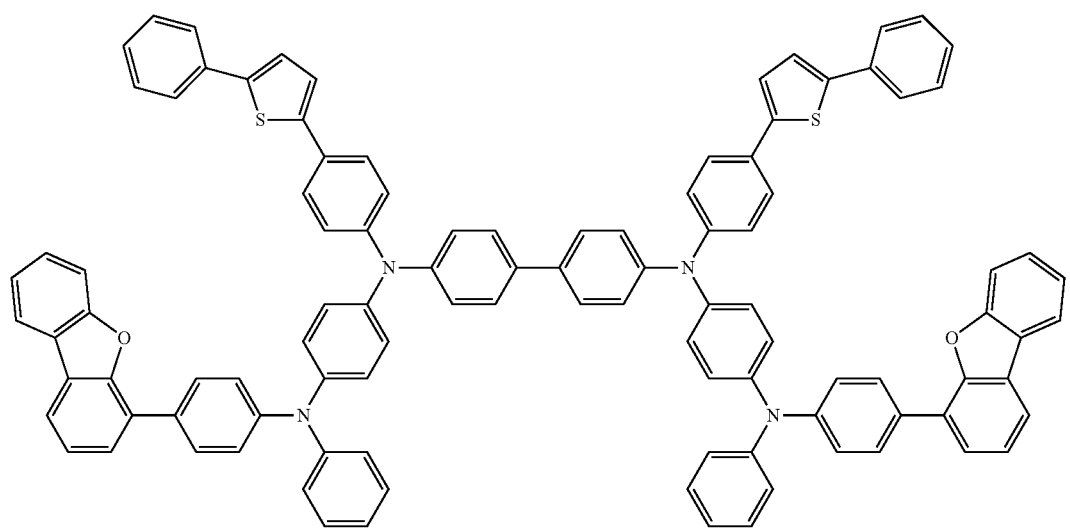

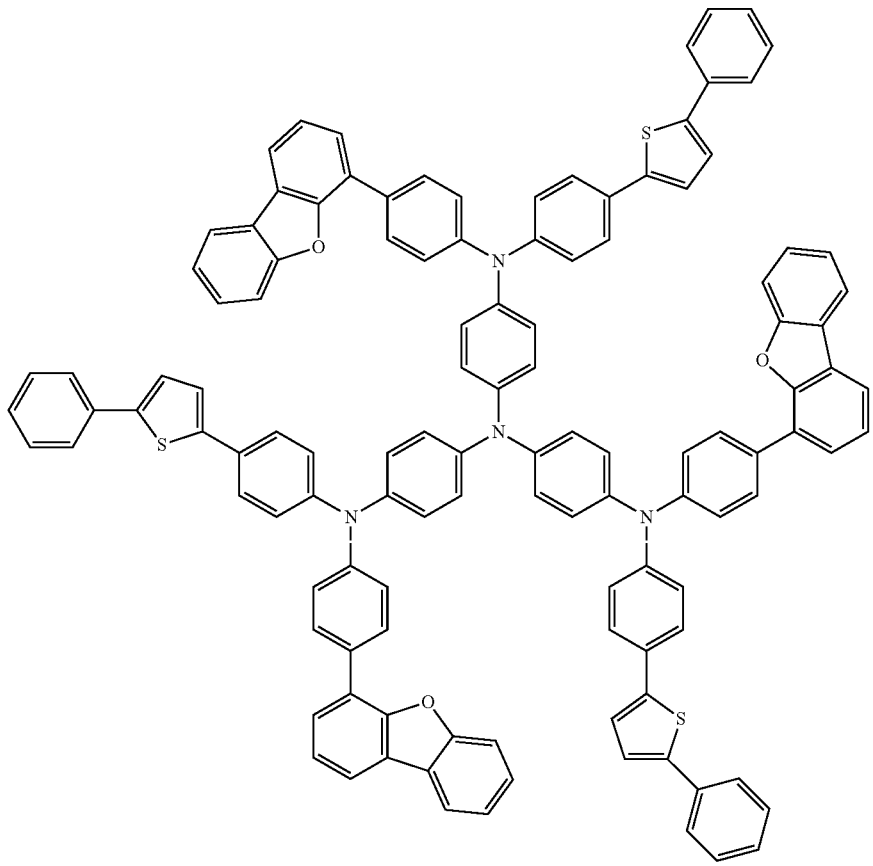

H18

Synthesis Embodiment 1

Synthesis of Compound H1

Under an argon stream, 2.5 g of Intermediate 6, 6.8 g of Intermediate 10, 2.6 g of sodium t-butoxide (manufactured by Hiroshima Wako Co., Ltd.), 92 mg of tris(dibenzylideneacetone)dipalladium(0) (manufactured by Aldrich Chemical Company, Inc.), 42 mg of tri-t-butylphosphine, and 100 mL of dehydrated toluene were charged, and the mixture was reacted at 80° C. for 8 hours.

After the reactant was cooled, 500 mL of water was added thereto, and the mixture was filtered with celite. The filtrate was extracted with toluene and dried with anhydrous magnesium sulfate. The resultant was concentrated under reduced pressure, and the obtained crude product was subjected to column purification. The purified product was recrystallized with toluene, followed by filtration and drying, whereby 5.1 g of pale yellow powder was obtained. By an FD-MS analysis, the pale yellow powder was identified as Compound H1.

Synthesis Embodiment 2

Synthesis of Compound H2

The same reaction as in Synthesis Embodiment 1 was carried out except that 6.1 g of Intermediate 11 was used instead of Intermediate 10, whereby 4.3 g of pale yellow powder was obtained. By an FD-MS analysis, the pale yellow powder was identified as Compound H2.

Synthesis Embodiment 3

Synthesis of Compound H3

The same reaction as in Synthesis Embodiment 1 was carried out except that 6.8 g of Intermediate 12 was used instead of Intermediate 10, whereby 4.1 g of pale yellow powder was obtained. By an FD-MS analysis, the pale yellow powder was identified as Compound H3.

Synthesis Embodiment 4

Synthesis of Compound H4

The same reaction as in Synthesis Embodiment 1 was carried out except that 6.8 g of Intermediate 13 was used instead of Intermediate 10, whereby 5.3 g of pale yellow powder was obtained. By an FD-MS analysis, the pale yellow powder was identified as Compound H4.

Synthesis Embodiment 5

Synthesis of Compound H5

The same reaction as in Synthesis Embodiment 1 was carried out except that 7.7 g of Intermediate 14 was used instead of Intermediate 10, whereby 3.2 g of pale yellow powder was obtained. By an FD-MS analysis, the pale yellow powder was identified as Compound H5.

Synthesis Embodiment 6

Synthesis of Compound H6

The same reaction as in Synthesis Embodiment 1 was carried out except that 8.4 g of Intermediate 15 was used instead of Intermediate 10, whereby 4.4 g of pale yellow powder was obtained. By an FD-MS analysis, the pale yellow powder was identified as Compound H6.

Synthesis Embodiment 7

Synthesis of Compound H7

The same reaction as in Synthesis Embodiment 1 was carried out except that 9.9 g of Intermediate 18 was used instead of Intermediate 6 and 4.3 g of 1-bromonaphthalene was used instead of Intermediate 10, whereby 7.9 g of pale yellow powder was obtained. By an FD-MS analysis, the pale yellow powder was identified as Compound H7.

Synthesis Embodiment 8

Synthesis of Compound H8

The same reaction as in Synthesis Embodiment 7 was carried out except that 5.5 g of 4-bromo-(9,9-dimethyl)fluorene was used instead of 1-bromonaphthalene, whereby 6.9 g of pale yellow powder was obtained. By an FD-MS analysis, the pale yellow powder was identified as Compound H8.

Synthesis Embodiment 9

Synthesis of Compound H9

The same reaction as in Synthesis Embodiment 7 was carried out except that 6.5 g of 4-bromoterphenyl was used instead of 1-bromonaphthalene, whereby 7.5 g of pale yellow powder was obtained. By an FD-MS analysis, the pale yellow powder was identified as Compound H9.

Synthesis Embodiment 10

Synthesis of Compound H10

The same reaction as in Synthesis Embodiment 7 was carried out except that 6.8 g of Intermediate 13 was used instead of 1-bromonaphthalene, whereby 7.8 g of pale yellow powder was obtained. By an FD-MS analysis, the pale yellow powder was identified as Compound H10.

Synthesis Embodiment 11

Synthesis of Compound H11

The same reaction as in Synthesis Embodiment 7 was carried out except that 7.7 g of Intermediate 14 was used instead of 1-bromonaphthalene, whereby 4.6 g of pale yellow powder was obtained. By an FD-MS analysis, the pale yellow powder was identified as Compound H11.

Synthesis Embodiment 12

Synthesis of Compound H12

The same reaction as in Synthesis Embodiment 7 was carried out except that 8.2 g of Intermediate 8 was used instead of 1-bromonaphthalene, whereby 9.8 g of pale yellow powder was obtained. By an FD-MS analysis, the pale yellow powder was identified as Compound H12.

Synthesis Embodiment 13

Synthesis of Compound H13

The same reaction as in Synthesis Embodiment 7 was carried out except that 6.8 g of Intermediate 9 was used instead of 1-bromonaphthalene, whereby 7.3 g of pale yellow powder was obtained. By an FD-MS analysis, the pale yellow powder was identified as Compound H13.

Synthesis Embodiment 14

Synthesis of Compound H14

The same reaction as in Synthesis Embodiment 1 was carried out except that Intermediate 20 was used instead of Intermediate 6 and Intermediate 3 was used instead of Intermediate 10, whereby 5.2 g of pale yellow powder was obtained. By an FD-MS analysis, the pale yellow powder was identified as Compound H14.

Synthesis Embodiment 15

Synthesis of Compound H15

The same reaction as in Synthesis Embodiment 1 was carried out except that Intermediate 22 was used instead of Intermediate 10, whereby 10.1 g of pale yellow powder was obtained. By an FD-MS analysis, the pale yellow powder was identified as Compound H15.

Synthesis Embodiment 16

Synthesis of Compound H16

The same reaction as in Synthesis Embodiment 1 was carried out except that Intermediate 20 was used instead of Intermediate 6 and Intermediate 23 was used instead of Intermediate 10, whereby 9.8 g of pale yellow powder was obtained. By an FD-MS analysis, the pale yellow powder was identified as Compound H16.

Synthesis Embodiment 17

Synthesis of Compound H17

The same reaction as in Synthesis Embodiment 1 was carried out except that Intermediate 7 was used instead of Intermediate 6 and Intermediate 18 was used instead of Intermediate 10, whereby 10.4 g of pale yellow powder was obtained. By an FD-MS analysis, the pale yellow powder was identified as Compound H17.

Synthesis Embodiment 18

Synthesis of Compound H18

The same reaction as in Synthesis Embodiment 1 was carried out except that 4.8 g of tris(4-bromophenyl)amine was used instead of Intermediate 6 and 15.3 g of Intermediate 18 was used instead of Intermediate 10, whereby 10.1 g of pale yellow powder was obtained. By an FD-MS analysis, the pale yellow powder was identified as Compound H18.

Example 1

Production of Organic EL Device

A glass substrate with an ITO transparent electrode measuring 25 mm wide by 75 mm long by 1.1 mm thick (manufactured by GEOMATEC Co., Ltd.) was subjected to ultrasonic cleaning in isopropyl alcohol for 5 minutes. After that, the substrate was subjected to UV ozone cleaning for 30 minutes.

The glass substrate with the transparent electrode line after the washing was mounted on a substrate holder of a vacuum deposition device. First, Compound H1 was formed into a film having a thickness of 60 nm, using Compound H1 film as the hole transporting material, on the surface on the side where the transparent electrode line was formed to cover the transparent electrode. The H1 film functions as a hole injecting layer. The following Compound layer TBDB was formed into a film having a thickness of 20 nm on the H1 film. The film functions as a hole transporting layer. Further, Compound EM1 to be described below was deposited from the vapor and formed into a film having a thickness of 40 nm. Simultaneously with this formation, Amine Compound D1 having a styryl group to be described below, as a light emitting molecule, was deposited from the vapor in such a manner that a weight ratio between Compound EM1 and Amine Compound D1 would be 40:2. The film functions as a light emitting layer.

Alq to be described below was formed into a film having a thickness of 10 nm on the resultant film. The film functions as an electron injecting layer. After that, Li serving as a reducing dopant (Li source: manufactured by SAES Getters) and Alq were subjected to co-deposition. Thus, an Alq:Li film (having a thickness of 10 nm) was formed as an electron injecting layer (cathode). Metal Al was deposited from the vapor onto the Alq:Li film to form a metal cathode. Thus, an organic EL device was formed.

In addition, the current efficiency of the resultant organic EL device was measured, and the luminescent color of the device was observed. A current efficiency at 10 mA/cm$^2$ was calculated by measuring a luminance by using CS1000 (trade name) manufactured by Minolta. Further, the half lifetime of light emission in DC constant current driving at an initial luminance of 5,000 cd/m$^2$ and room temperature was measured. Table 1 shows the results thereof.

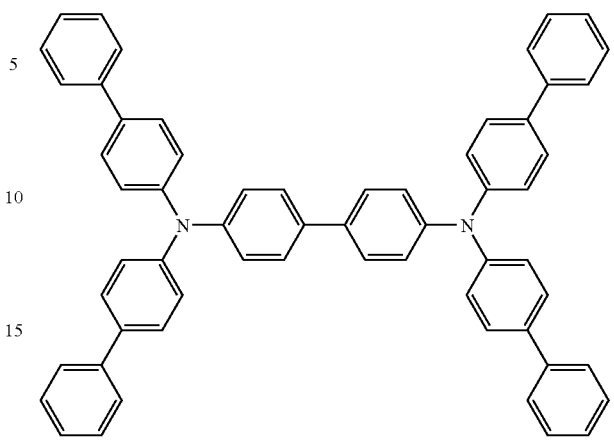
TBDB

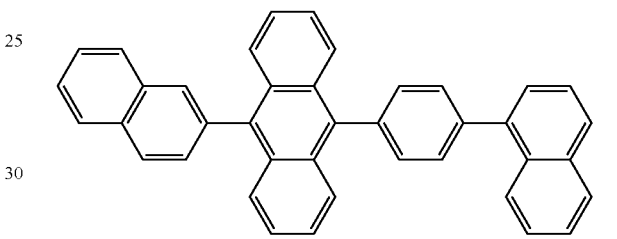
EM1

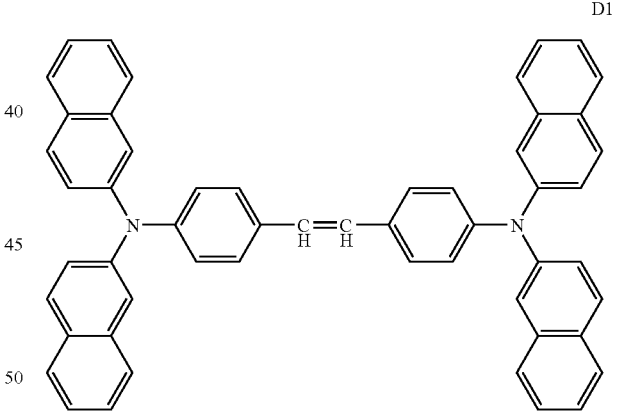
D1

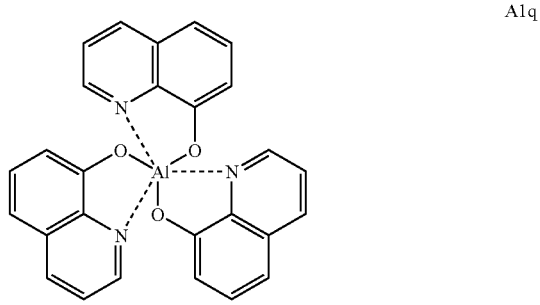
Alq

Examples 2 to 7

Production of Organic EL Device

Each organic EL device was produced in the same manner as in Example 1 except that the compound shown in Table 1 was used as a hole transporting material instead of Compound H1.

The current efficiency of the resultant organic EL device was measured, and the luminescent color of the device was observed in the same manner as in Example 1. Further, the half lifetime of light emission in DC constant current driving at an initial luminance of 5,000 cd/m$^2$ and room temperature was measured. Table 1 shows the results thereof.

Comparative Examples 1 to 11

An organic EL device was produced in the same manner as in Example 1 except that the following Comparative Compounds 1 to 11 were each used as a hole transporting material instead of Compound H1.

In addition, the current efficiency of the resultant organic EL device was measured, and the luminescent color of the device was observed in the same manner as in Example 1. Further, the half lifetime of light emission in DC constant current driving at an initial luminance of 5,000 cd/m$^2$ and room temperature was measured. Table 1 shows the results thereof.

TABLE 1

Comparative Compound 1

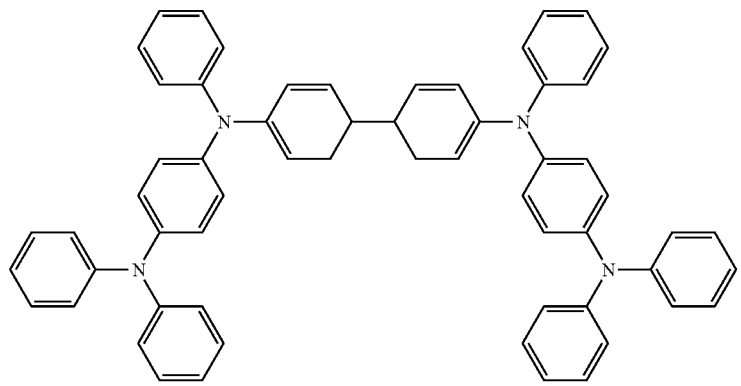

Comparative Compound 2

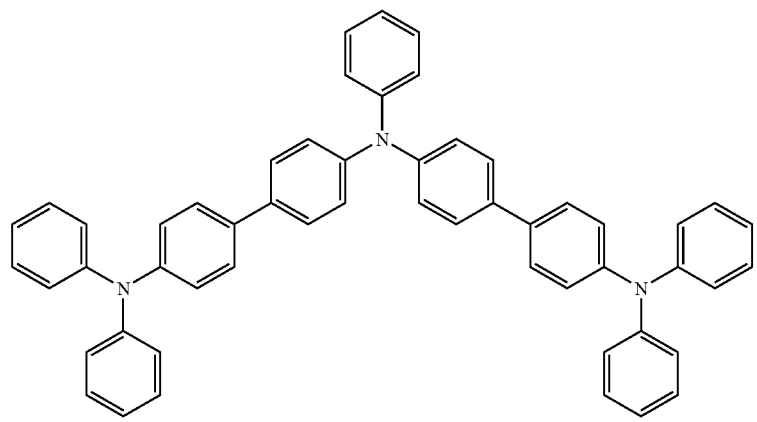

TABLE 1-continued
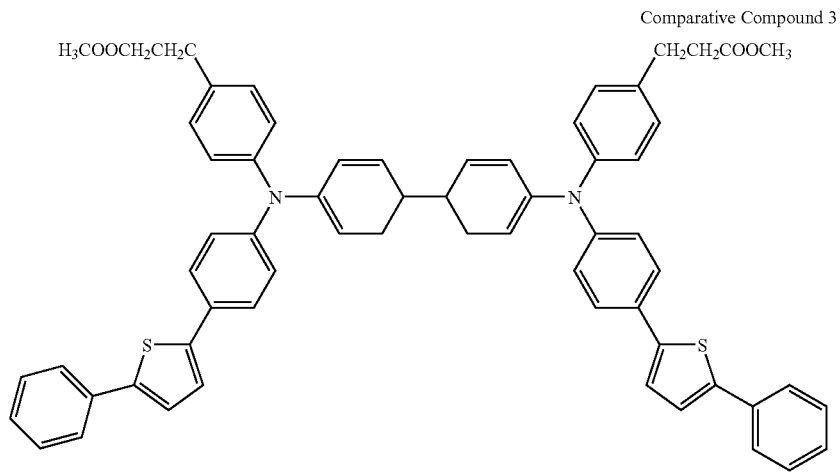
Comparative Compound 3
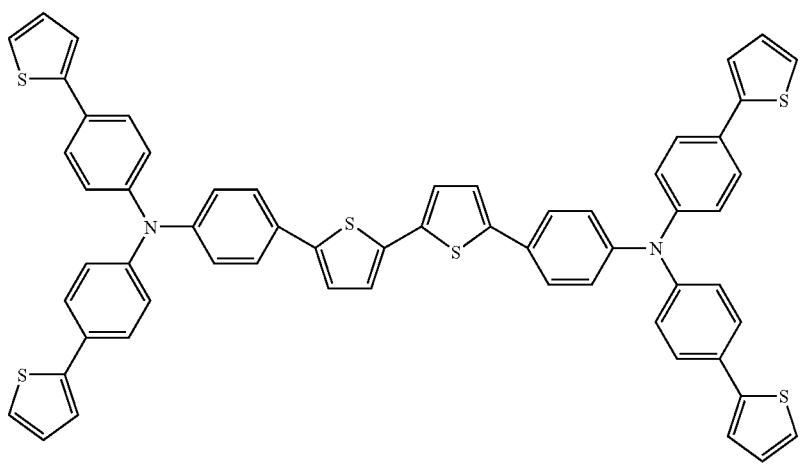
Comparative Compound 4
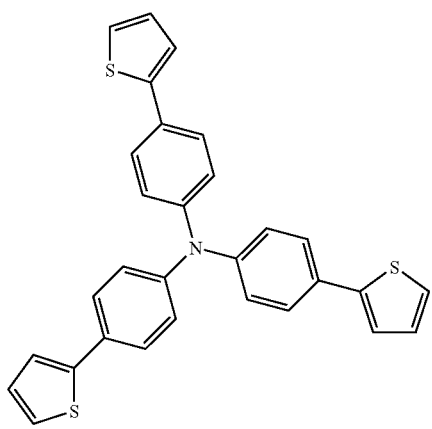
Comparative Compound 5

TABLE 1-continued
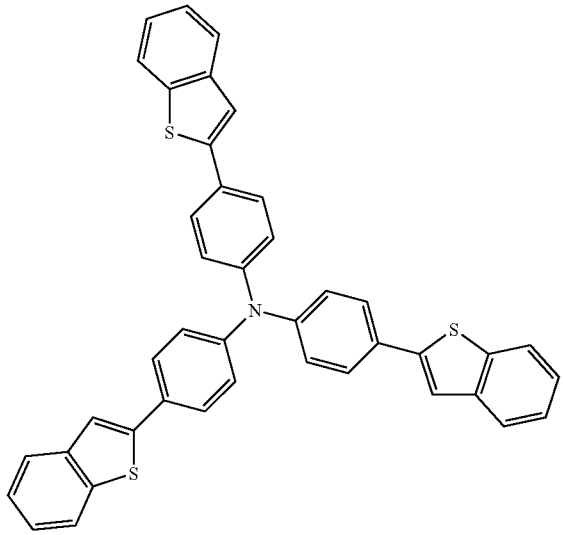
Comparative Compound 6
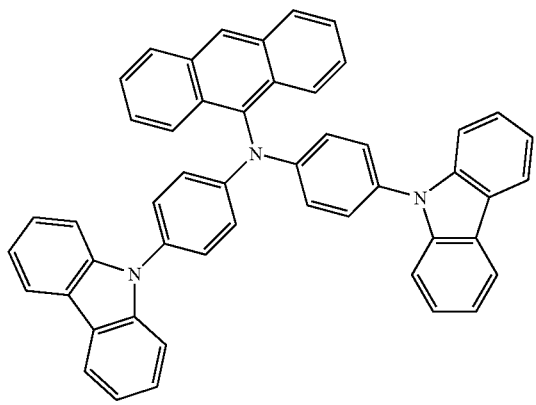
Comparative Compound 7
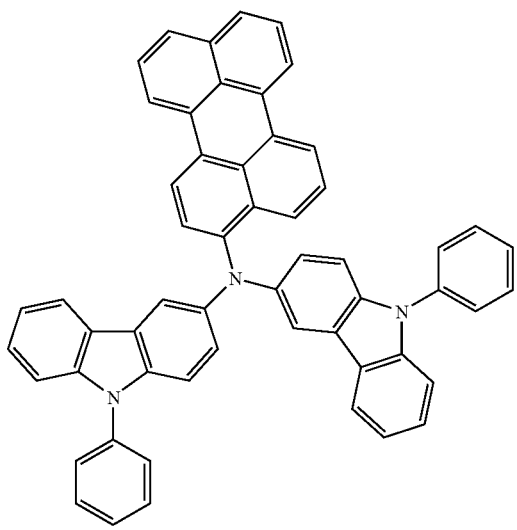
Comparative Compound 8

Comparative Compound 9
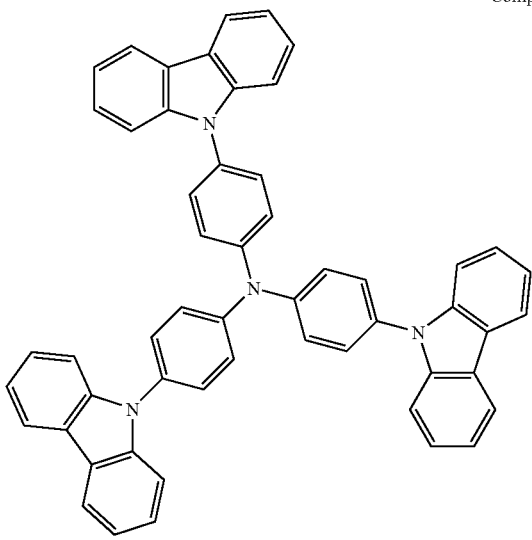
Comparative Compound 10
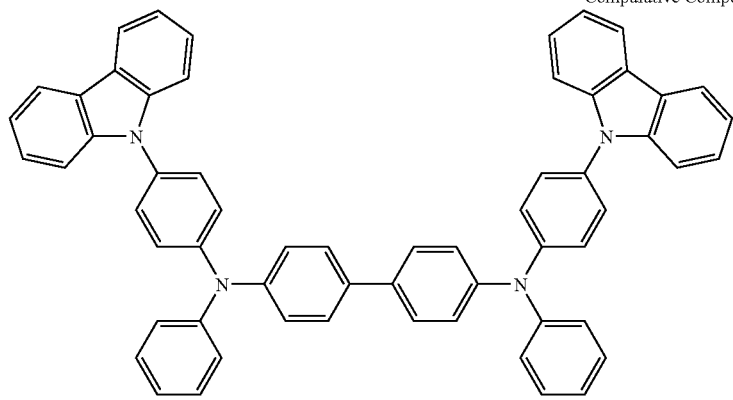
Comparative Compound 11
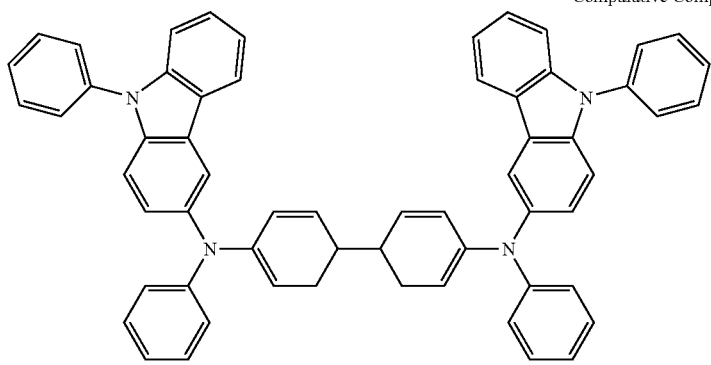
| Example | Hole transporting material | Votage (V) | Luminescent color | Half lifetime (hours) |
|---|---|---|---|---|
| 1 | H1 | 6.2 | Blue | 440 |
| 2 | H2 | 6.4 | Blue | 400 |
| 3 | H3 | 6.5 | Blue | 370 |
| 4 | H4 | 6.4 | Blue | 400 |
| 5 | H5 | 6.1 | Blue | 360 |
| 6 | H6 | 6.0 | Blue | 380 |
| 7 | H12 | 6.4 | Blue | 410 |
| 8 | H1 | 6.2 | Blue | 430 |

TABLE 1-continued

| | | | | |
|---|---|---|---|---|
| Comparative Example 1 | Comparative Compound 1 | 7.1 | Blue | 280 |
| Comparative Example 2 | Comparative Compound 2 | 6.9 | Blue | 240 |
| Comparative Example 3 | Comparative Compound 3 | 6.2 | Blue | 120 |
| Comparative Example 4 | Comparative Compound 4 | 6.6 | Blue | 150 |
| Comparative Example 5 | Comparative Compound 5 | 6.5 | Blue | 80 |
| Comparative Example 6 | Comparative Compound 6 | 6.9 | Blue | 180 |
| Comparative Example 7 | Comparative Compound 7 | 8.2 | Blue | 130 |
| Comparative Example 8 | Comparative Compound 8 | 7.4 | Blue | 110 |
| Comparative Example 9 | Comparative Compound 9 | 8.4 | Blue | 150 |
| Comparative Example 10 | Comparative Compound 10 | 7.9 | Blue | 200 |
| Comparative Example 11 | Comparative Compound 11 | 7.2 | Blue | 220 |
| Comparative Example 12 | Comparative Compound 1 | 7.0 | Blue | 270 |

Example 8

Production of Organic EL Device

An organic EL device was produced in the same manner as in Example 1 except that the following Arylamine Compound D2 was used instead of Amine Compound D1 having a styryl group. Me represents a methyl group.

The current efficiency of the resultant organic EL device was measured, and the luminescent color of the device was observed in the same manner as in Example 1. Further, the half lifetime of light emission in DC constant current driving at an initial luminance of 5,000 cd/m² and room temperature was measured. Table 1 shows the results thereof.

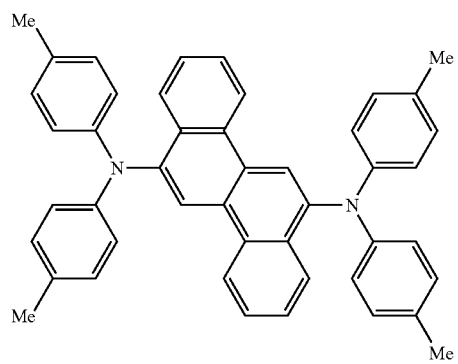

D2

Comparative Example 12

An organic EL device was produced in the same manner as in Example 8 except that the above Comparative Compound 1 was used instead of Compound H1.

The current efficiency of the resultant organic EL device was measured, and the luminescent color of the device was observed in the same manner as in Example 1. Further, the half lifetime of light emission in DC constant current driving at an initial luminance of 5,000 cd/m² and room temperature was measured. Table 1 shows the results thereof.

INDUSTRIAL APPLICABILITY

As described above in detail, the aromatic amine derivative of the present invention provides an organic EL device in which molecules hardly crystallize, and which decreases a driving voltage when used as a material for the organic EL device, has a long lifetime, and can be produced with improved yields upon the production of the organic EL device. Therefore, the aromatic amine derivative of the present invention is extremely useful as a highly practical organic EL device.

The invention claimed is:

1. An aromatic amine derivative represented by the following general formula (1):

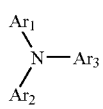

(1)

where: at least one of $Ar_1$ to $Ar_3$ is represented by formula (2); and at least one of $Ar_1$ to $Ar_3$ is represented by any one of formulae (3) to (7):

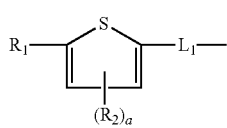

(2)

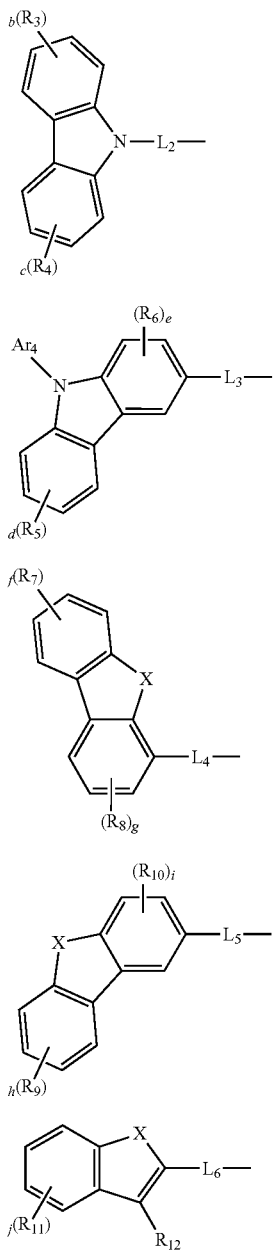

where: $R_2$ to $R_{11}$ each independently represent a substituted or unsubstituted aryl group having 6 to 50 ring atoms, a substituted or unsubstituted and linear or branched alkyl group having 1 to 50 carbon atoms, a halogen atom, or a cyano group; and $R_1$ and $R_{12}$ each independently represent a hydrogen atom, a substituted or unsubstituted aryl group having 6 to 50 ring atoms, a substituted or unsubstituted and linear or branched alkyl group having 1 to 50 carbon atoms, a halogen atom, or a cyano group;
a represents an integer of 0 to 2;
b, c, d, f, h, and j each represent an integer of 0 to 4; and
e, g, and i each represent an integer of 0 to 3;
X represents sulfur or oxygen; and
$L_1$ and $L_4$ to $L_6$ each independently represent a substituted or unsubstituted arylene group having 6 to 50 ring atoms; and $L_2$ and $L_3$ each independently represent a single bond or a substituted or unsubstituted arylene group having 6 to 50 ring atoms; and where, in formula (1), $Ar_1$ to $Ar_3$ which are the groups other than the groups represented by formulae (2) to (7) each independently represent a substituted or unsubstituted aryl group having 6 to 50 ring atoms, wherein a substituent of the aryl group comprises an aryl group having 6 to 50 ring atoms, a linear or branched alkyl group having 1 to 50 carbon atoms, a halogen atom, a cyano group, or a group represented by formula (8):

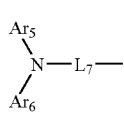

where: $L_7$ represents a substituted or unsubstituted arylene group having 6 to 50 ring atoms; and $Ar_5$ and $Ar_6$ each independently represent a substituted or unsubstituted aryl group having 6 to 50 ring atoms or a substituted or unsubstituted heteroaryl group having 6 to 50 ring atoms, with the proviso that at least one of the following conditions (i) to (iii) is satisfied:

condition (i): in formula (1), $Ar_1$ is represented by formula (2) and $Ar_2$ and $Ar_3$ are each represented by any one of formulae (2) to (7);

condition (ii): in formula (1), $Ar_1$ and $Ar_2$ are each represented by formula (2) and $Ar_3$ is represented by any one of formulae (2) to (7); and condition (iii): in formula (2), $L_1$ represents a phenylene group, a biphenylene group, or a fluorenylene group; $R_1$ represents a phenyl group, a naphthyl group, or a phenanthrenyl group; and a represents 0.

2. The aromatic amine derivative according to claim 1, wherein said condition (i) is satisfied.

3. The aromatic amine derivative according to claim 1, wherein said condition (ii) is satisfied.

4. The aromatic amine derivative according to claim 1, wherein said condition (iii) is satisfied.

5. An aromatic amine derivative represented by one of formulae (9) to (12):

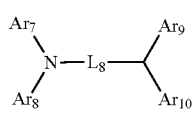

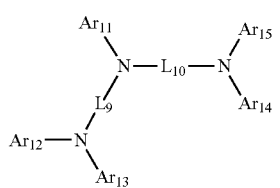

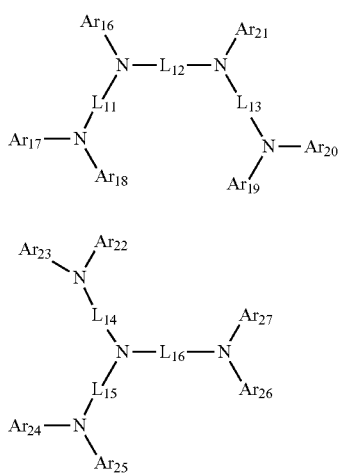

(11)

(12)

where, in formula (9): at least one of $Ar_7$ to $Ar_{10}$ is represented by formula (13); and at least one of $Ar_7$ to $Ar_{10}$ is represented by any one of formulae (14) to (18), where, in formula (10): at least one of $Ar_{11}$ to $Ar_{15}$ is represented by formula (13); and at least one of $Ar_{11}$ to $Ar_{15}$ is represented by any one of formulae (14) to (18), where, in formula (11): at least one of $Ar_{16}$ to $Ar_{21}$ is represented by formula (13); and at least one of $Ar_{16}$ to $Ar_{21}$ is represented by any one of formulae (14) to (18), where, in formula (12): at least one of $Ar_{22}$ to $Ar_{27}$ is represented by formula (13); and at least one of $Ar_{22}$ to $Ar_{27}$ is represented by any one of formulae (14) to (18):

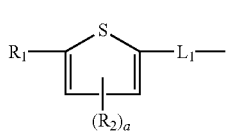

(13)

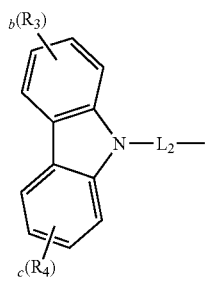

(14)

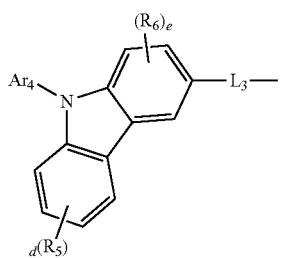

(15)

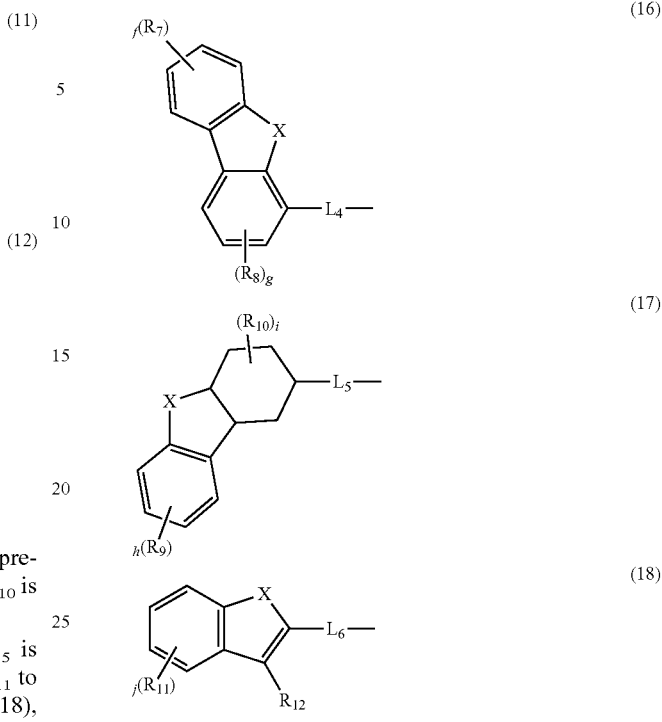

where: $R_2$ to $R_{11}$ each independently represent a substituted or unsubstituted aryl group having 6 to 50 ring atoms, a substituted or unsubstituted and linear or branched alkyl group having 1 to 50 carbon atoms, a halogen atom, or a cyano group; and $R_1$ and $R_{12}$ each independently represent a hydrogen atom, a substituted or unsubstituted aryl group having 6 to 50 ring atoms, a substituted or unsubstituted and linear or branched alkyl group having 1 to 50 carbon atoms, a halogen atom, or a cyano group;

a represents an integer of 0 to 2;

b, c, d, f, h, and j each represent an integer of 0 to 4; and e, g, and i each represent an integer of 0 to 3;

X represents sulfur or oxygen; and $L_1$ and $L_4$ to $L_6$ each independently represent a substituted or unsubstituted arylene group having 6 to 50 ring atoms; and $L_2$ and $L_3$ each independently represent a single bond or a substituted or unsubstituted arylene group having 6 to 50 ring atoms; and where, in formulae (9) to (12): $Ar_7$ to $Ar_{27}$ which are the groups other than the groups represented by formulae (13) to (18) each independently represent a substituted or unsubstituted aryl group having 6 to 50 ring atoms; and $L_8$ to $L_{16}$ each independently represent a substituted or unsubstituted arylene group having 6 to 50 ring carbon atoms.

6. The aromatic amine derivative according to claim 5, wherein, in formula (9), $Ar_7$ and $Ar_8$ are each represented by formula (13) and $Ar_9$ and $Ar_{10}$ are each represented by any one of formulae (14) to (18).

7. The aromatic amine derivative according to claim 5, wherein, in formula (9), $Ar_7$ and $Ar_9$ are each represented by formula (13) and $Ar_8$ and $Ar_{10}$ are each represented by any one of formulae (14) to (18).

8. The aromatic amine derivative according to claim 5, wherein, in formula (10), $Ar_{11}$ is represented by formula (13) and $Ar_{13}$ and $Ar_{14}$ are each represented by any one of formulae (14) to (18).

9. The aromatic amine derivative according to claim 5, wherein, in formula (10), $Ar_{13}$ and $Ar_{14}$ are each represented by formula (13) and $Ar_{11}$ is represented by any one of formulae (14) to (18).

10. The aromatic amine derivative according to claim 5, wherein, in formula (11), $Ar_{16}$ and $Ar_{21}$ are each represented by formula (13) and $Ar_{18}$ and $Ar_{19}$ are each represented by any one of formulae (14) to (18).

11. The aromatic amine derivative according to claim 5, wherein, in formula (11), $Ar_{18}$ and $Ar_{19}$ are each represented by formula (13) and $Ar_{16}$ and $Ar_{21}$ are each represented by any one of formulae (14) to (18).

12. The aromatic amine derivative according to claim 5, wherein, in formula (12), $Ar_{22}$, $Ar_{24}$, and $Ar_{26}$ are each represented by formula (13) and $Ar_{23}$, $Ar_{25}$, and $Ar_{27}$ are each represented by any one of formulae (14) to (18).

13. The aromatic amine derivative according to claim 5, wherein, in formula (13):
   $L_1$ represents a phenylene group, a biphenylene group, or a fluorenylene group;
   $R_1$ represents a phenyl group, a naphthyl group, or a phenanthrenyl group; and
   a represents 0.

14. The aromatic amine derivative according to claim 5, wherein, in formulae (9) to (12), $Ar_7$ to $Ar_{27}$ each independently represent a phenyl group, a naphthyl group, a biphenyl group, a terphenyl group, or a fluorenyl group.

15. The aromatic amine derivative according to claim 5, wherein, in formulae (9) to (12), $L_8$ to $L_{16}$ each independently represent a phenylene group, a naphthylene group, a biphenylene group, a terphenylene group, or a fluorenylene group.

16. The aromatic amine derivative according to claim 1, which is a material for an organic electroluminescent device.

17. The aromatic amine derivative according to claim 1, which is a hole transporting material for an organic electroluminescent device.

18. An organic electroluminescent device, comprising an organic thin film layer interposed between a cathode and an anode and formed of one layer or a plurality of layers including at least a light emitting layer,
   wherein at least one layer of the organic thin film layer contains the aromatic amine derivative according to claim 1 alone or as a component of a mixture.

19. The organic electroluminescent device according to claim 18, wherein:
   the organic thin film layer comprises a hole transporting layer and/or a hole injecting layer; and
   the aromatic amine derivative is contained in the hole transporting layer and/or the hole injecting layer.

20. The organic electroluminescent device according to claim 18, wherein:
   the organic thin film layer comprises a hole transporting zone comprising at least a hole transporting layer and a hole injecting layer; and
   the aromatic amine derivative is contained in a layer which is in the hole transporting zone and is other than a layer directly attached to a light emitting layer.

21. The organic electroluminescent device according to claim 18, wherein the aromatic amine derivative is contained in a hole transporting layer and/or a hole injecting layer as a main component.

22. The organic electroluminescent device according to claim 18, comprising a styrylamine compound and/or an arylamine compound in a light emitting layer.

23. The organic electroluminescent device according to claim 21, wherein a layer which is one of respective layers constituting the hole injecting layer and/or the hole transporting layer and is in contact with an anode is a layer containing an acceptor material.

24. The organic electroluminescent device according to claim 18, which emits blue light.

25. An organic electroluminescent device, comprising an organic thin film layer interposed between a cathode and an anode and formed of one layer or a plurality of layers including at least a light emitting layer,
   wherein at least one layer of the organic thin film layer contains the aromatic amine derivative according to claim 5 alone or as a component of a mixture.

26. The organic electroluminescent device according to claim 25, wherein:
   the organic thin film layer comprises a hole transporting layer and/or a hole injecting layer; and
   the aromatic amine derivative is contained in the hole transporting layer and/or the hole injecting layer.

27. The organic electroluminescent device according to claim 25, wherein:
   the organic thin film layer comprises a hole transporting zone comprising at least a hole transporting layer and a hole injecting layer; and
   the aromatic amine derivative is contained in a layer which is in the hole transporting zone and is other than a layer directly attached to a light emitting layer.

28. The organic electroluminescent device according to claim 25, wherein the aromatic amine derivative is contained in a hole transporting layer and/or a hole injecting layer as a main component.

29. The organic electroluminescent device according to claim 25, comprising a styrylamine compound and/or an arylamine compound in a light emitting layer.

30. The organic electroluminescent device according to claim 28, wherein a layer which is one of respective layers constituting the hole injecting layer and/or the hole transporting layer and is in contact with an anode is a layer containing an acceptor material.

31. The organic electroluminescent device according to claim 25, which emits blue light.

32. The aromatic amine derivative according to claim 5, which is a material for an organic electroluminescent device.

33. The aromatic amine derivative according to claim 5, which is a hole transporting material for an organic electroluminescent device.

* * * * *